US009045683B2

(12) United States Patent
Taugerbeck et al.

(10) Patent No.: US 9,045,683 B2
(45) Date of Patent: Jun. 2, 2015

(54) POLYMERIZABLE COMPOUNDS AND USE THEREOF IN LIQUID CRYSTAL DISPLAYS

(75) Inventors: Andreas Taugerbeck, Darmstadt (DE); Achim Goetz, Alsbach-Hahnlein (DE); Stephan Derow, Griesheim (DE)

(73) Assignee: Merck Patent GmbH, Darmstadt (DE)

( * ) Notice: Subject to any disclaimer, the term of this patent is extended or adjusted under 35 U.S.C. 154(b) by 105 days.

(21) Appl. No.: 13/805,481

(22) PCT Filed: Jun. 1, 2011

(86) PCT No.: PCT/EP2011/002726
§ 371 (c)(1),
(2), (4) Date: Dec. 19, 2012

(87) PCT Pub. No.: WO2011/106765
PCT Pub. Date: Dec. 29, 2011

(65) Prior Publication Data
US 2013/0093975 A1    Apr. 18, 2013

(30) Foreign Application Priority Data

Jun. 25, 2010 (DE) .......................... 10 2010 025 091

(51) Int. Cl.
| | |
|---|---|
| C09K 19/12 | (2006.01) |
| C09K 19/32 | (2006.01) |
| C09K 19/54 | (2006.01) |
| C09K 19/18 | (2006.01) |
| C09K 19/20 | (2006.01) |
| C07C 69/602 | (2006.01) |
| C09K 19/30 | (2006.01) |
| G02F 1/1333 | (2006.01) |
| C09K 19/04 | (2006.01) |

(52) U.S. Cl.
CPC ............... *C09K 19/322* (2013.01); *C09K 19/18* (2013.01); *C09K 19/2014* (2013.01); *C09K 19/32* (2013.01); *C09K 2019/0448* (2013.01); *C09K 2019/548* (2013.01); *C07C 69/602* (2013.01); *C09K 19/3003* (2013.01); *G02F 1/1333* (2013.01)

(58) Field of Classification Search
CPC ................. C09K 19/18; C09K 19/322; C09K 2019/0411; C09K 2019/0448; C09K 2019/0466; C09K 2019/122; C09K 2019/181; C09K 2019/188; C09K 2019/2014; C09K 2019/2092; C09K 2019/3004; C09K 2019/3009; C09K 2019/301; C09K 2019/3016; C09K 2019/3036; C09K 2019/304; C09K 2019/3048; C09K 2019/305; C09K 2019/548; G02F 1/1333
USPC ........... 252/299.62, 299.63; 428/1.1; 560/194
See application file for complete search history.

(56) References Cited

U.S. PATENT DOCUMENTS

| | | | |
|---|---|---|---|
| 5,769,393 A * | 6/1998 | Kobayashi et al. ...... | 252/299.01 |
| 6,673,267 B2 | 1/2004 | Sekine et al. | |
| 7,597,942 B2 | 10/2009 | May et al. | |
| 7,820,072 B2 | 10/2010 | Hsieh et al. | |
| 7,993,710 B2 | 8/2011 | Hsieh et al. | |
| 8,021,571 B2 | 9/2011 | May et al. | |
| 8,075,959 B2 | 12/2011 | Hsieh et al. | |
| 8,304,035 B2 | 11/2012 | Bernatz et al. | |
| 2002/0006479 A1 | 1/2002 | Sekine et al. | |
| 2008/0143943 A1 | 6/2008 | May et al. | |
| 2008/0236727 A1 | 10/2008 | Hsieh et al. | |
| 2009/0109392 A1 | 4/2009 | Hsieh et al. | |
| 2009/0324855 A1 | 12/2009 | Hsieh et al. | |
| 2010/0208191 A1 | 8/2010 | May et al. | |
| 2010/0309423 A1 | 12/2010 | Bernatz et al. | |
| 2011/0001919 A1 | 1/2011 | Hsieh et al. | |
| 2011/0051049 A1 | 3/2011 | Goetz et al. | |
| 2011/0178200 A1 | 7/2011 | Parri et al. | |

FOREIGN PATENT DOCUMENTS

| | | |
|---|---|---|
| CN | 101671252 A | 3/2010 |
| DE | 100 64 291 A1 | 7/2001 |
| DE | 10 2008 036 248 A1 | 3/2009 |
| DE | 10 2009 011 652 A1 | 10/2009 |
| EP | 2 218 764 A1 | 8/2010 |
| JP | 2002-012579 A | 1/2002 |
| WO | 2009086911 A1 | 7/2009 |

OTHER PUBLICATIONS

Yao, Y-H, et al., "Synthesis of UV-curable liquid crystalline diacrylates for the application of polarized electroluminescence," Liquid Crystals: An International Journal of Science and Technology, Jan. 1, 2006, vol. No. 33, No. 1, pp. 33-39, Taylor & Frances, GB; Cited in International Search Report, dated Oct. 7, 2011, issued in corresponding PCT/EP2011/002726.

Sekine, C., et al., "High birefringence photopolymerizable phenylacetylene liquid crystals," Liquid Crystals: An International Journal of Science and Technology, Oct. 1, 2001, vol. No. 28, No. 10, pp. 1505-1512, Taylor & Frances, GB; Cited in International Search Report, dated Oct. 7, 2011, issued in corresponding PCT/EP2011/002726.

International Search Report, dated Oct. 7, 2011, issued in corresponding PCT/EP2011/002726.

English-language Abstract corresponding to Chinese publication No. 101671252 (5 pages).

* cited by examiner

*Primary Examiner* — Shean C Wu

(74) *Attorney, Agent, or Firm* — Millen, White, Zelano, Branigan, P.C.

(57) ABSTRACT

The present invention relates to polymerizable compounds, to processes and intermediates for the preparation thereof, and to the use thereof for optical, electro-optical and electronic purposes, in particular in liquid-crystal (LC) media and LC displays, especially in LC displays of the PS ("polymer sustained") or PSA ("polymer sustained alignment") type.

22 Claims, No Drawings

POLYMERIZABLE COMPOUNDS AND USE THEREOF IN LIQUID CRYSTAL DISPLAYS

The present invention relates to polymerisable compounds, to processes and intermediates for the preparation thereof, and to the use thereof for optical, electro-optical and electronic purposes, in particular in liquid-crystal (LC) media and LC displays, especially in LC displays of the PS ("polymer sustained") or PSA ("polymer sustained alignment") type.

The liquid-crystal displays (LC displays) used at present are usually those of the TN ("twisted nematic") type. However, these have the disadvantage of a strong viewing-angle dependence of the contrast. In addition, so-called VA ("vertically aligned") displays are known which have a broader viewing angle. The LC cell of a VA display contains a layer of an LC medium between two transparent electrodes, where the LC medium usually has a negative value of the dielectric (DC) anisotropy. In the switched-off state, the molecules of the LC layer are aligned perpendicular to the electrode surfaces (homeotropically) or have a tilted homeotropic alignment. On application of an electrical voltage to the two electrodes, a realignment of the LC molecules parallel to the electrode surfaces takes place.

Furthermore, OCB ("optically compensated bend") displays are known which are based on a birefringence effect and have an LC layer with a so-called "bend" alignment and usually positive (DC) anisotropy. On application of an electrical voltage, a realignment of the LC molecules perpendicular to the electrode surfaces takes place. In addition, OCB displays normally contain one or more birefringent optical retardation films in order to prevent undesired transparency to light of the bend cell in the dark state. OCB displays have a broader viewing angle and shorter response times compared with TN displays.

Also known are so-called IPS ("in-plane switching") displays, which contain an LC layer between two substrates, where the two electrodes are arranged on only one of the two substrates and preferably have intermeshed, comb-shaped structures. On application of a voltage to the electrodes, an electric field which has a significant component parallel to the LC layer is thereby generated between them. This causes a realignment of the LC molecules in the layer plane.

Furthermore, so-called FFS ("fringe-field switching") displays have been proposed (see, inter alia, S. H. Jung et al., Jpn. J. Appl. Phys., Volume 43, No. 3, 2004, 1028), which likewise contain two electrodes on the same substrate, but, in contrast to IPS displays, only one of these is in the form of an electrode which is structured in a comb-shaped manner, and the other electrode is unstructured. A strong, so-called "fringe field" is thereby generated, i.e. a strong electric field close to the edge of the electrodes, and, throughout the cell, an electric field which has both a strong vertical component and also a strong horizontal component. Both IPS displays and also FFS displays have a low viewing-angle dependence of the contrast.

In VA displays of the more recent type, uniform alignment of the LC molecules is restricted to a plurality of relatively small domains within the LC cell. Disclinations may exist between these domains, also known as tilt domains. VA displays having tilt domains have, compared with conventional VA displays, a greater viewing-angle independence of the contrast and the grey shades. In addition, displays of this type are simpler to produce since additional treatment of the electrode surface for uniform alignment of the molecules in the switched-on state, such as, for example, by rubbing, is no longer necessary. Instead, the preferential direction of the tilt or pretilt angle is controlled by a special design of the electrodes.

In so-called MVA ("multidomain vertical alignment") displays, this is usually achieved by the electrodes having protrusions which cause a local pretilt. As a consequence, the LC molecules are aligned parallel to the electrode surfaces in different directions in different, defined regions of the cell on application of a voltage. "Controlled" switching is thereby achieved, and the formation of interfering disclination lines is prevented. Although this arrangement improves the viewing angle of the display, it results, however, in a reduction in its transparency to light.

A further development of MVA uses protrusions on only one electrode side, while the opposite electrode has slits, which improves the transparency to light. The slotted electrodes generate an inhomogeneous electric field in the LC cell on application of a voltage, meaning that controlled switching is still achieved. For further improvement of the transparency to light, the separations between the slits and protrusions can be increased, but this in turn results in a lengthening of the response times.

In so-called PVA (patterned VA), protrusions are rendered completely superfluous in that both electrodes are structured by means of slits on the opposite sides, which results in increased contrast and improved transparency to light, but is technologically difficult and makes the display more sensitive to mechanical influences ("tapping", etc.). For many applications, such as, for example, monitors and especially TV screens, however, a shortening of the response times and an improvement in the contrast and luminance (transmission) of the display are demanded.

A further development are the so-called PS (polymer sustained) or PSA (polymer sustained alignment) displays, for which the term "polymer stabilised" is also occasionally used. In these displays, a small amount (for example 0.3% by weight, typically <1% by weight) of one or more polymerisable compound(s) is added to the LC medium and, after introduction into the LC cell, is polymerised or crosslinked in situ, usually by UV photopolymerisation, between the electrodes with or without an applied electrical voltage. The addition of polymerisable mesogenic or liquid-crystalline compounds, also known as reactive mesogens or "RMs", to the LC mixture has proven particularly suitable.

Unless indicated otherwise, the term "PSA" is used below as representative of PS displays and PSA displays.

In the meantime, the PS(A) principle is being used in diverse classical LC displays. Thus, for example, PSA-VA, PSA-OCB, PSA-IPS, PSA-FFS and PSA-TN displays are known. The polymerisation of the polymerisable compound(s) preferably takes place with an applied electrical voltage in the case of PSA-VA and PSA-OCB displays, and with or without an applied electrical voltage in the case of PSA-IPS displays. As can be demonstrated in test cells, the PS(A) method results in a pretilt in the cell. In the case of PSA-OCB displays, for example, it is possible for the bend structure to be stabilised so that an offset voltage is unnecessary or can be reduced. In the case of PSA-VA displays, the pretilt has a positive effect on response times. For PSA-VA displays, a standard MVA or PVA pixel and electrode layout can be used. In addition, however, it is also possible, for example, to manage with only one structured electrode side and no protrusions, which significantly simplifies production and at the same time results in very good contrast at the same time as very good transparency to light.

In addition, so-called positive-VA displays have proven to be a particularly favourable embodiment. The initial alignment of the liquid crystals in the voltage-free starting state here, just as in the case of classical VA displays, is homeotropic, i.e. essentially perpendicular to the substrates. In contrast to classical VA displays, however, positive-VA displays use dielectrically positive LC media. By application of an electrical voltage to interdigital electrodes, which generate a field essentially parallel to the layer of the LC medium, the LC molecules are converted into an alignment which is essentially parallel to the substrates. Interdigital electrodes of this type are also usually used in IPS displays. Corresponding polymer stabilisation (PSA) has also proven to be advantageous in the case of positive VA displays, enabling a considerable reduction to be achieved in the response times.

PSA-VA displays are described, for example, in JP 10-036847 A, EP 1 170 626 A2, U.S. Pat. No. 6,861,107, U.S. Pat. No. 7,169,449, US 2004/0191428 A1, US 2006/0066793 A1 and US 2006/0103804 A1. PSA-OCB displays are described, for example, in T.-J- Chen et al., Jpn. J. Appl. Phys. 45, 2006, 2702-2704 and S. H. Kim, L.-C- Chien, Jpn. J. Appl. Phys. 43, 2004, 7643-7647. PSA-IPS displays are described, for example, in U.S. Pat. No. 6,177,972 and Appl. Phys. Lett. 1999, 75(21), 3264. PSA-TN displays are described, for example, in Optics Express 2004, 12(7), 1221.

Like the conventional LC displays described above, PSA displays can be operated as active-matrix or passive-matrix displays. In the case of active-matrix displays, individual pixels are usually addressed by integrated, non-linear active elements, such as, for example, transistors (for example thin-film transistors ("TFTs")), while in the case of passive-matrix displays, individual pixels are usually addressed by the multiplex method, where both methods are known from the prior art.

In particular for monitor and especially TV applications, optimisation of the response times, but also of the contrast and luminance (thus also transmission) of the LC display continues to be demanded. The PSA method can provide crucial advantages here. In particular in the case of PSA-VA, PSA-IPS, PSA-FFS and PSA-positive-VA displays, a shortening of the response times, which correlate with a measurable pretilt in test cells, can be achieved without significant adverse effects on other parameters.

In the prior art, use is made, for example, of polymerisable compounds of the following formula:

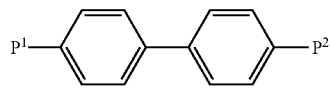

in which P denotes a polymerisable group, usually an acrylate or methacrylate group, as described, for example, in U.S. Pat. No. 7,169,449.

However, the problem arises that not all combinations consisting of LC mixture (also referred to as "LC host mixture" below)+polymerisable component (typically RMs) are suitable for PSA displays since, for example, an inadequate tilt or none at all becomes established or since, for example, the so-called "voltage holding ratio" (VHR or HR) is inadequate for TFT display applications. In addition, it has been found that, on use in PSA displays, the LC mixtures and RMs known from the prior art still have some disadvantages. Thus, not every known RM which is soluble in LC mixtures is suitable for use in PSA displays. In addition, it is often difficult to find a suitable selection criterion for the RM besides direct measurement of the pretilt in the PSA display. The choice of suitable RMs becomes even smaller if polymerisation by means of UV light without the addition of photoinitiators is desired, which may be advantageous for certain applications.

In addition, the selected combination of LC host mixture/RM should have the lowest possible rotational viscosity and the best possible electrical properties. In particular, it should have the highest possible VHR. In PSA displays, a high VHR after irradiation with UV light is particularly necessary since UV exposure is a requisite part of the display production process, but also occurs as normal exposure during operation of the finished display.

In particular, it would be desirable to have available novel materials for PSA displays which produce a particularly small pretilt angle. Preferred materials here are those which produce a lower pretilt angle during polymerisation for the same exposure time than the materials known to date, and/or through the use of which the (higher) pretilt angle that can be achieved with known materials can already be achieved after a shorter exposure time. The production time ("tact time") of the display could thus be shortened and the costs of the production process reduced.

A further problem in the production of PSA displays is the presence or removal of residual amounts of unpolymerised RMs, in particular after the polymerisation step for production of the pretilt angle in the display. For example, unreacted RMs of this type may adversely affect the properties of the display by, for example, polymerising in an uncontrolled manner during operation after finishing of the display.

Thus, the PSA displays known from the prior art often exhibit the undesired effect of so-called "image sticking" or "image burn", i.e. the image produced in the LC display by temporary addressing of individual pixels still remains visible even after the electric field in these pixels has been switched off or after other pixels have been addressed.

This "image sticking" can occur on the one hand if LC host mixtures having a low VHR are used. The UV component of daylight or the backlighting can cause undesired decomposition reactions of the LC molecules therein and thus initiate the production of ionic or free-radical impurities. These may accumulate, in particular, at the electrodes or the alignment layers, where they may reduce the effective applied voltage. This effect can also be observed in conventional LC displays without a polymer component.

In addition, an additional "image sticking" effect caused by the presence of unpolymerised RMs is often observed in PSA displays. Uncontrolled polymerisation of the residual RMs is initiated here by UV light from the environment or by the backlighting. In the switched display areas, this changes the tilt angle after a number of addressing cycles. As a result, a change in transmission in the switched areas may occur, while it remains unchanged in the unswitched areas.

It is therefore desirable for the polymerisation of the RMs to proceed as completely as possible during production of the PSA display and for the presence of unpolymerised RMs in the display to be excluded as far as possible or reduced to a minimum. To this end, materials are required which enable highly effective and complete polymerisation. In addition, controlled reaction of these residual amounts would be desirable. This would be simpler if the RM polymerised more rapidly and effectively than the materials known to date.

There is thus still a great demand for PSA displays, in particular of the VA and OCB type, and LC media and polymerisable compounds for use in such displays, which do not exhibit the disadvantages described above or only do so to a small extent and have improved properties. In addition, there is a great demand for PSA displays, and materials for use in PSA displays, which have advantageous properties, in particular enable a high specific resistance at the same time as a large working-temperature range, short response times, even at low temperatures, and a low threshold voltage, a low pretilt angle, a multiplicity of grey shades, high contrast and a broad viewing angle, and have high values for the "voltage holding ratio" (VHR) after UV exposure and for the low-temperature stability, also known as "LTS", i.e. the stability of the LC mixture to spontaneous crystallisation-out of individual components.

The invention is based on the object of providing novel suitable materials, in particular RMs and LC media comprising same, for use in PSA displays, which do not have the disadvantages indicated above or do so to a reduced extent, polymerise as rapidly and completely as possible, enable a low pretilt angle to be established as quickly as possible, reduce or prevent the occurrence of "image sticking" in the display, and preferably at the same time enable very high specific resistance values, low threshold voltages and short response times. In addition, the LC media should have favourable LC phase properties and high VHR and LTS values.

A further object of the invention is the provision of novel RMs, in particular for optical, electro-optical and electronic applications, and of suitable processes and intermediates for the preparation thereof.

In particular, the invention is based on the object of providing polymerisable compounds which produce a greater maximum pretilt after photopolymerisation, which results in the desired pretilt being achieved more quickly and thus in significantly shortened times for production of the LC display.

This object has been achieved in accordance with the invention by the provision of materials, processes and LC displays as described in the present application. In particular, it has been found, surprisingly, that some or all of the objects described above can be achieved by providing PSA displays which contain one or more polymerised compounds according to the invention or by using LC media which comprise one or more polymerisable compounds according to the invention for the production of PSA displays of this type.

The use of polymerisable compounds of this type in LC media and PSA displays according to the invention results in the desired pretilt being achieved particularly quickly and in significantly shortened times for production of the display. This has been demonstrated in connection with an LC medium by means of exposure time-dependent pretilt measurements in VA tilt measurement cells. In particular, it was possible to achieve a pretilt without the addition of photoinitiator.

Since the polymerisable compounds according to the invention exhibit a significantly faster polymerisation rate in the PSA displays, fewer unreacted residual amounts also remain in the LC cell, improving the electro-optical properties thereof and simplifying controlled reaction of these residual amounts.

The use of polymerisable compounds according to the invention in PSA displays for rapid establishment of a tilt angle by in-situ polymerisation in an electric field has neither been described in nor is obvious from the prior art.

In addition, it has been found, entirely surprisingly, that polymerisable compounds according to the invention exhibit, on use in PSA displays, significantly faster tilt angle generation and faster and more complete polymerisation than polymerisable compounds known from the prior art. This has been confirmed by direct comparative experiments. This result was neither described in nor obvious from the prior art.

The invention thus relates to the use of compounds of the formula I (also referred to below as "polymerisable compounds according to the invention")

$$P\text{-}(Sp)_{s1}\text{-}A^1\text{-}Z^1\text{-}A^2(\text{-}Z^2\text{-}A^3)_m\text{-}(Sp)_{s2}\text{-}P \qquad I$$

in which the individual radicals have the following meanings:
P on each occurrence, identically or differently, denotes a polymerisable group,
Sp on each occurrence, identically or differently, denotes a spacer group,
s1, s2 each, independently of one another, denote 0 or 1,
$A^1$, $A^2$, $A^3$ each, independently of one another, denote 1,4-phenylene, naphthalene-1,4-diyl or naphthalene-2,6-diyl, where, in addition, one or more CH groups in these groups may be replaced by N, phenanthrene-2,7-diyl, anthracene-2,7-diyl, 9,10-dihydrophenanthrene-2,7-diyl, 9H-fluorene-2,7-diyl, 9,9-dimethylfluorene-2,7-diyl or dibenzofuran-3,7-diyl, where all these groups may be unsubstituted or mono- or polysubstituted by L,
m denotes 0, 1 or 2,
L on each occurrence, identically or differently, denotes P—, P-Sp-, OH, CH$_2$OH, halogen, —CN, —NO$_2$, —NCO, —NCS, —OCN, —SCN, —C(=O)N($R^x$)$_2$, —C(=O)$Y^1$, —C(=O)$R^x$, —N($R^x$)$_2$, optionally substituted silyl or an optionally substituted carbon group or hydrocarbon group,
$R^x$ denotes P—, P-Sp-, H, halogen, straight-chain, branched or cyclic alkyl having 1 to 25, preferably 1 to 12, C atoms, in which, in addition, one or more non-adjacent CH$_2$ groups may be replaced by —O—, —S—, —CO—, —CO—O—, —O—CO—, —O—CO—O— in such a way that O and/or S atoms are not linked directly to one another, and in which, in addition, one or more H atoms may be replaced by F, Cl, P— or P-Sp-,
$Y^1$ denotes halogen,
$Z^1$, $Z^2$ each, independently of one another, denote —CO—O—, —OCO—, —CY=CY—, —C≡C— or a single bond,
Y on each occurrence, identically or differently, denotes H or F,
where at least one of the radicals $Z^1$ and $Z^2$ denotes —C≡C—,
in liquid-crystal (LC) media and LC displays of the PS or PSA (polymer sustained alignment) type.

The invention furthermore relates to an LC medium comprising one or more compounds of the formula I and one or more additional compounds, which may also be mesogenic, liquid-crystalline and/or polymerisable.

The invention furthermore relates to an LC medium comprising a polymer obtainable by polymerisation of one or more compounds of the formula I and one or more additional compounds, which may also be mesogenic, liquid-crystalline and/or polymerisable.

The invention furthermore relates to an LC medium comprising
a polymerisable component A) comprising one or more compounds of the formula I, and
a liquid-crystalline component B), also referred to below as "LC host mixture", comprising one or more, preferably two or more, low-molecular-weight (monomeric and unpolymerisable) compounds as described above and below.

The invention furthermore relates to a process for the preparation of an LC medium as described above and below in which one or more low-molecular-weight liquid-crystalline compounds, or an LC host mixture as described above and below, are mixed with one or more compounds of the formula I and optionally with further liquid-crystalline compounds and/or additives.

The invention furthermore relates to the use of compounds of the formula I and LC media according to the invention in PS and PSA displays, in particular the use in PS and PSA displays containing an LC medium, for the production of a tilt angle in the LC medium by in-situ polymerisation of the compound(s) of the formula I in the PSA display, preferably with application of an electric or magnetic field.

The invention furthermore relates to an LC display containing one or more compounds of the formula I or an LC medium according to the invention, in particular a PS or PSA display, particularly preferably a PSA-VA, PSA-OCB, PSA-IPS, PSA-FFS, PSA-positive-VA or PSA-TN display.

The invention furthermore relates to an LC display of the PS or PSA type containing an LC cell having two substrates and two electrodes, where at least one substrate is transparent to light and at least one substrate has one or two electrodes, and a layer, located between the substrates, of an LC medium comprising a polymerised component and a low-molecular-weight component, where the polymerised component is obtainable by polymerisation of one or more polymerisable compounds between the substrates of the LC cell in the LC medium, preferably with application of an electrical voltage to the electrodes, where at least one of the polymerisable compounds is a compound of the formula I.

The invention furthermore relates to a process for the production of an LC display as described above and below in which an LC medium comprising one or more low-molecular-weight liquid-crystalline compounds or an LC host mixture as described above and below and one or more compounds of the formula I is introduced into an LC cell having two substrates and two electrodes as described above and below, and the polymerisable compounds are polymerised, preferably with application of an electrical voltage to the electrodes.

The PS and PSA displays according to the invention have two electrodes, preferably in the form of transparent layers, which are applied to one or both of the substrates which form the LC cell. Either in each case one electrode is applied to each of the two substrates, as, for example, in PSA-VA, PSA-OCB or PSA-TN displays according to the invention, or both electrodes are applied to only one of the two substrates, while the other substrate has no electrode, as, for example, in PSA-positive-VA, PSA-IPS or PSA-FFS displays according to the invention.

The invention furthermore relates to novel compounds of the formula I, to processes for the preparation thereof, and to novel intermediates used or obtained in these processes.

The following meanings apply above and below:

The terms "tilt" and "tilt angle" relate to a tilted alignment of the LC molecules of an LC medium relative to the surfaces of the cell in an LC display (here preferably a PS or PSA display). The tilt angle here denotes the average angle (<90°) between the longitudinal molecular axes of the LC molecules (LC director) and the surface of the plane-parallel outer plates which form the LC cell. A low value for the tilt angle (i.e. a large deviation from the 90° angle) corresponds to a large tilt here. A suitable method for measurement of the tilt angle is given in the examples. Unless indicated otherwise, tilt angle values disclosed above and below relate to this measurement method.

The term "mesogenic group" is known to the person skilled in the art and is described in the literature, and denotes a group which, due to the anisotropy of its attracting and repelling interactions, essentially contributes to causing a liquid-crystal (LC) phase in low-molecular-weight or polymeric substances. Compounds containing mesogenic groups (mesogenic compounds) do not necessarily have to have an LC phase themselves. It is also possible for mesogenic compounds to exhibit LC phase behaviour only after mixing with other compounds and/or after polymerisation. Typical mesogenic groups are, for example, rigid rod- or disc-shaped units. An overview of the terms and definitions used in connection with mesogenic or LC compounds is given in Pure Appl. Chem. 73(5), 888 (2001) and C. Tschierske, G. Pelzl, S. Diele, Angew. Chem. 2004, 116, 6340-6368.

The term "spacer group", also referred to as "Sp" above and below, is known to the person skilled in the art and is described in the literature, see, for example, Pure Appl. Chem. 73(5), 888 (2001) and C. Tschierske, G. Pelzl, S. Diele, Angew. Chem. 2004, 116, 6340-6368. Unless indicated otherwise, the term "spacer group" or "spacer" above and below denotes a flexible group which connects the mesogenic group and the polymerisable group(s) to one another in a polymerisable mesogenic compound.

The term "reactive mesogen" or "RM" denotes a compound containing one mesogenic group and one or more functional groups which are suitable for polymerisation (also referred to as polymerisable group or group P).

The terms "low-molecular-weight compound" and "unpolymerisable compound" denote compounds, usually monomeric, which contain no functional group which is suitable for polymerisation under the usual conditions known to the person skilled in the art, in particular under the conditions used for the polymerisation of RMs.

The term "organic group" denotes a carbon or hydrocarbon group.

The term "carbon group" denotes a mono- or polyvalent organic group containing at least one carbon atom, preferably 1 to 40 C atoms, where this either contains no further atoms (such as, for example, —C≡C—) or optionally contains one or more further atoms, such as, for example, N, O, S, P, Si, Se, As, Te or Ge (for example carbonyl, etc.). The term "hydrocarbon group" denotes a carbon group which additionally contains one or more H atoms and optionally one or more heteroatoms, such as, for example, N, O, S, P, Si, Se, As, Te or Ge.

"Halogen" denotes F, Cl, Br or I.

A carbon or hydrocarbon group can be a saturated or unsaturated group. Unsaturated groups are, for example, aryl, alkenyl or alkynyl groups. A carbon or hydrocarbon radical having more than 3 C atoms can be straight-chain, branched and/or cyclic and may also have spiro links or condensed rings.

The terms "alkyl", "aryl", "heteroaryl", etc., also include polyvalent groups, for example alkylene, arylene, heteroarylene, etc.

The term "aryl" denotes an aromatic carbon group or a group derived therefrom. The term "heteroaryl" denotes "aryl" in accordance with the above definition containing one or more heteroatoms.

Preferred carbon and hydrocarbon groups are optionally substituted alkyl, alkenyl, alkynyl, alkoxy, alkylcarbonyl, alkoxycarbonyl, alkylcarbonyloxy and alkoxycarbonyloxy having 1 to 40, preferably 1 to 25, particularly preferably 1 to 18, C atoms, optionally substituted aryl, heteroaryl, aryloxy and heteroaryloxy having 1 to 40, preferably 1 to 25, C atoms, and optionally substituted alkylaryl, arylalkyl, alkylaryloxy, arylalkyloxy, arylcarbonyl, aryloxycarbonyl, arylcarbonyloxy and aryloxycarbonyloxy having 6 to 40, preferably 6 to 25, C atoms.

Further preferred carbon and hydrocarbon groups are $C_1$-$C_{40}$ alkyl, $C_2$-$C_{40}$ alkenyl, $C_2$-$C_{40}$ alkynyl, $C_3$-$C_{40}$ alkyl, $C_4$-$C_{40}$ alkyldienyl, $C_4$-$C_{40}$ polyenyl, $C_6$-$C_{40}$ aryl, $C_6$-$C_{40}$ alkylaryl, $C_6$-$C_{40}$ arylalkyl, $C_6$-$C_{40}$ alkylaryloxy, $C_6$-$C_{40}$ arylalkyloxy, $C_2$-$C_{40}$ heteroaryl, $C_4$-$C_{40}$ cycloalkyl, $C_4$-$C_{40}$ cycloalkenyl, etc. Particular preference is given to $C_1$-$C_{22}$ alkyl, $C_2$-$C_{22}$ alkenyl, $C_2$-$C_{22}$ alkynyl, $C_3$-$C_{22}$ alkyl, $C_4$-$C_{22}$ alkyldienyl, $C_6$-$C_{12}$ aryl, $C_6$-$C_{20}$ arylalkyl and $C_2$-$C_{20}$ heteroaryl.

Further preferred carbon and hydrocarbon groups are straight-chain, branched or cyclic alkyl radicals having 1 to 40, preferably 1 to 25, C atoms, which are unsubstituted or mono- or polysubstituted by F, Cl, Br, I or CN, and in which one or more non-adjacent $CH_2$ groups may each be replaced, independently of one another, by —C($R^x$)=C($R^x$)—, —C≡C—, —N($R^x$)—, —O—, —S—, —CO—, —CO—O—, —O—CO—, —O—CO—O— in such a way that O and/or S atoms are not linked directly to one another.

$R^x$ preferably denotes H, halogen, a straight-chain, branched or cyclic alkyl chain having 1 to 25 C atoms, in which, in addition, one or more non-adjacent C atoms may be replaced by —O—, —S—, —CO—, —CO—O—, —O—CO—, —O—CO—O—, where, in addition, one or more H atoms may be replaced by fluorine, or denotes an optionally substituted aryl or aryloxy group having 6 to 40 C atoms or an optionally substituted heteroaryl or heteroaryloxy group having 2 to 40 C atoms.

Preferred alkoxy groups are, for example, methoxy, ethoxy, 2-methoxyethoxy, n-propoxy, i-propoxy, n-butoxy, i-butoxy, s-butoxy, t-butoxy, 2-methylbutoxy, n-pentoxy, n-hexoxy, n-heptoxy, n-octoxy, n-nonoxy, n-decoxy, n-undecoxy, n-dodecoxy, etc.

Preferred alkyl groups are, for example, methyl, ethyl, n-propyl, isopropyl, n-butyl, isobutyl, s-butyl, t-butyl, 2-methylbutyl, n-pentyl, s-pentyl, cyclopentyl, n-hexyl, cyclohexyl, 2-ethylhexyl, n-heptyl, cycloheptyl, n-octyl, cyclooctyl, n-nonyl, n-decyl, n-undecyl, n-dodecyl, dodecanyl, trifluoromethyl, perfluoro-n-butyl, 2,2,2-trifluoroethyl, perfluorooctyl, perfluorohexyl, etc.

Preferred alkenyl groups are, for example, ethenyl, propenyl, butenyl, pentenyl, cyclopentenyl, hexenyl, cyclohexenyl, heptenyl, cycloheptenyl, octenyl, cyclooctenyl, etc.

Preferred alkynyl groups are, for example, ethynyl, propynyl, butynyl, pentynyl, hexynyl, octynyl, etc.

Preferred alkoxy groups are, for example, methoxy, ethoxy, 2-methoxyethoxy, n-propoxy, i-propoxy, n-butoxy, i-butoxy, s-butoxy, t-butoxy, 2-methylbutoxy, n-pentoxy, n-hexoxy, n-heptoxy, n-octoxy, n-nonoxy, n-decoxy, n-undecoxy, n-dodecoxy, etc.

Preferred amino groups are, for example, dimethylamino, methylamino, methylphenylamino, phenylamino, etc.

Aryl and heteroaryl groups can be monocyclic or polycyclic, i.e. they can contain one ring (such as, for example, phenyl) or two or more rings, which may also be fused (such as, for example, naphthyl) or covalently bonded (such as, for example, biphenyl), or contain a combination of fused and linked rings. Heteroaryl groups contain one or more heteroatoms, preferably selected from O, N, S and Se.

Particular preference is given to mono-, bi- or tricyclic aryl groups having 6 to 25 C atoms and mono-, bi- or tricyclic heteroaryl groups having 2 to 25 C atoms, which optionally contain fused rings and are optionally substituted. Preference is furthermore given to 5-, 6- or 7-membered aryl and heteroaryl groups, in which, in addition, one or more CH groups may be replaced by N, S or O in such a way that O atoms and/or S atoms are not linked directly to one another.

Preferred aryl groups are, for example, phenyl, biphenyl, terphenyl, [1,1':3',1"]terphenyl-2'-yl, naphthyl, anthracene, binaphthyl, phenanthrene, pyrene, dihydropyrene, chrysene, perylene, tetracene, pentacene, benzopyrene, fluorene, indene, indenofluorene, spirobifluorene, etc.

Preferred heteroaryl groups are, for example, 5-membered rings, such as pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 6-membered rings, such as pyridine, pyridazine, pyrimidine, pyrazine, 1,3,5-triazine, 1,2,4-triazine, 1,2,3-triazine, 1,2,4,5-tetrazine, 1,2,3,4-tetrazine, 1,2,3,5-tetrazine, or condensed groups, such as indole, isoindole, indolizine, indazole, benzimidazole, benzotriazole, purine, naphthimidazole, phenanthrimidazole, pyridimidazole, pyrazinimidazole, quinoxalinimidazole, benzoxazole, naphthoxazole, anthroxazole, phenanthroxazole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquinoline, acridine, phenothiazine, phenoxazine, benzopyridazine, benzopyrimidine, quinoxaline, phenazine, naphthyridine, azacarbazole, benzocarboline, phenanthridine, phenanthroline, thieno[2,3b]-thiophene, thieno[3,2b]thiophene, dithienothiophene, isobenzothiophene, dibenzothiophene, benzothiadiazothiophene, or combinations of these groups. The heteroaryl groups may also be substituted by alkyl, alkoxy, thioalkyl, fluorine, fluoroalkyl or further aryl or heteroaryl groups.

The (non-aromatic) alicyclic and heterocyclic groups include both saturated rings, i.e. those containing exclusively single bonds, and also partially unsaturated rings, i.e. those which may also contain multiple bonds. Heterocyclic rings contain one or more heteroatoms, preferably selected from Si, O, N, S and Se.

The (non-aromatic) alicyclic and heterocyclic groups can be monocyclic, i.e. contain only one ring (such as, for example, cyclohexane), or polycyclic, i.e. contain a plurality of rings (such as, for example, decahydronaphthalene or bicyclooctane). Particular preference is given to saturated groups. Preference is furthermore given to mono-, bi- or tricyclic groups having 3 to 25 C atoms, which optionally contain fused rings and are optionally substituted. Preference is furthermore given to 5-, 6-, 7- or 8-membered carbocyclic groups, in which, in addition, one or more C atoms may be replaced by Si and/or one or more CH groups may be replaced by N and/or one or more non-adjacent $CH_2$ groups may be replaced by —O— and/or —S—.

Preferred alicyclic and heterocyclic groups are, for example, 5-membered groups, such as cyclopentane, tetrahydrofuran, tetrahydrothiofuran, pyrrolidine, 6-membered groups, such as cyclohexane, silinane, cyclohexene, tetrahydropyran, tetrahydrothiopyran, 1,3-dioxane, 1,3-dithiane, piperidine, 7-membered groups, such as cycloheptane, and fused groups, such as tetrahydronaphthalene, decahydronaphthalene, indane, bicyclo[1.1.1]-pentane-1,3-diyl, bicyclo[2.2.2]octane-1,4-diyl, spiro[3.3]heptane-2,6-diyl, octahydro-4,7-methanoindane-2,5-diyl.

Preferred substituents are, for example, solubility-promoting groups, such as alkyl or alkoxy, electron-withdrawing groups, such as fluorine, nitro or nitrile, or substituents for increasing the glass transition temperature (Tg) in the polymer, in particular bulky groups, such as, for example, t-butyl or optionally substituted aryl groups.

Preferred substituents, also referred to as "L" above and below, are, for example, F, Cl, Br, I, OH, —CN, —NO$_2$, —NCO, —NCS, —OCN, —SCN, —C(=O)N(R$^x$)$_2$, —C(=O)Y$^1$, —C(=O)R$^x$, —C(=O)OR$^x$, —N(R$^x$)$_2$, in which R$^x$ has the meaning indicated above, and Y$^1$ denotes halogen, and optionally substituted silyl, optionally substituted aryl or heteroaryl having 4 to 40, preferably 4 to 20, C atoms, and straight-chain or branched alkyl, alkenyl, alkynyl, alkoxy, alkylcarbonyl, alkoxycarbonyl, alkylcarbonyloxy or alkoxycarbonyloxy having 1 to 25 C atoms, in which one or more H atoms may optionally be replaced by F or Cl.

"Substituted silyl or aryl" preferably means substituted by halogen, —CN, R$^0$, —OR$^0$, —CO—R$^0$, —CO—O—R$^0$, —O—CO—R$^0$ or —O—CO—O—R$^0$, in which R$^0$ has the meaning indicated above.

Particularly preferred substituents L are, for example, F, Cl, CN, NO$_2$, CH$_3$, C$_2$H$_5$, OCH$_3$, OC$_2$H$_5$, COCH$_3$, COC$_2$H$_5$, COOCH$_3$, COOC$_2$H$_5$, CF$_3$, OCF$_3$, OCHF$_2$, OC$_2$F$_5$, furthermore phenyl.

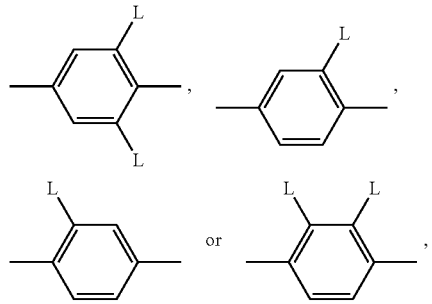

is preferably

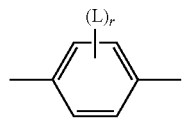

in which L has one of the meanings indicated above.

The polymerisable group P is a group which is suitable for a polymerisation reaction, such as, for example, free-radical or ionic chain polymerisation, polyaddition or polycondensation, or for a polymer-analogous reaction, for example addition or condensation onto a main polymer chain. Particular preference is given to groups for chain polymerisation, in particular those containing a C=C double bond or —C≡C— triple bond, and groups which are suitable for polymerisation with ring opening, such as, for example, oxetane or epoxide groups.

Preferred groups P are selected from the group consisting of CH$_2$=CW$^1$—CO—O—, CH$_2$=CW$^1$—CO—,

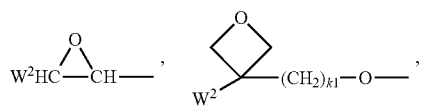

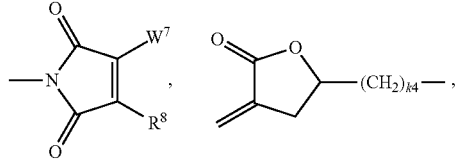

CH$_2$=CW$^2$—(O)$_{k3}$—, CW$^1$=CH—CO—(O)$_{k3}$—, CW$^1$=CH—CO—NH—, CH$_2$=CW$^1$—CO—NH—, CH$_3$—CH=CH—O—, (CH$_2$=CH)$_2$CH—OCO—, (CH$_2$=CH—CH$_2$)$_2$CH—OCO—, (CH$_2$=CH)$_2$CH—O—, (CH$_2$=CH—CH$_2$)$_2$N—, (CH$_2$=CH—CH$_2$)$_2$N—CO—, HO—CW$^2$W$^3$—, HS—CW$^2$W$^3$—, HW$^2$N—, HO—CW$^2$W$^3$—NH—, CH$_2$=CW$^1$—CO—NH—, CH$_2$=CH—(COO)$_{k1}$-Phe-(O)$_{k2}$—, CH$_2$=CH—(CO)$_{k1}$-Phe-(O)$_{k2}$—, Phe-CH=CH—, HOOC—, OCN— and W$^4$W$^5$W$^6$Si—, in which W$^1$ denotes H, F, Cl, CN, CF$_3$, phenyl or alkyl having 1 to 5 C atoms, in particular H, F, Cl or CH$_3$, W$^2$ and W$^3$ each, independently of one another, denote H or alkyl having 1 to 5 C atoms, in particular H, methyl, ethyl or n-propyl, W$^4$, W$^5$ and W$^6$ each, independently of one another, denote Cl, oxaalkyl or oxacarbonylalkyl having 1 to 5 C atoms, W$^7$ and W$^8$ each, independently of one another, denote H, Cl or alkyl having 1 to 5 C atoms, Phe denotes 1,4-phenylene, which is optionally substituted by one or more radicals L as defined above which are other than P-Sp-, k$_1$, k$_2$ and k$_3$ each, independently of one another, denote 0 or 1, k$_3$ preferably denotes 1, and k$_4$ denotes an integer from 1 to 10.

Particularly preferred groups P are selected from the group consisting of CH$_2$=CW$^1$—CO—O—, CH$_2$=CW$^1$—CO—,

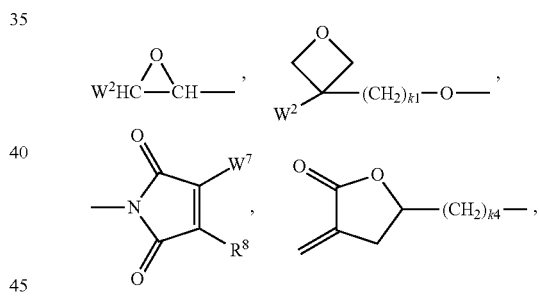

CH$_2$=CW$^2$—O—, CW$^1$=CH—CO—(O)$_{k3}$—, CW$^1$=CH—CO—NH—, CH$_2$=CW$^1$—CO—NH—, (CH$_2$=CH)$_2$CH—OCO—, (CH$_2$=CH—CH$_2$)$_2$CH—OCO—, (CH$_2$=CH)$_2$CH—O—, (CH$_2$=CH—CH$_2$)$_2$N—, (CH$_2$=CH—CH$_2$)$_2$N—CO—, CH$_2$=CW$^1$—CO—NH—, CH$_2$=CH—(COO)$_{k1}$-Phe-(O)$_{k2}$—, CH$_2$=CH—(CO)$_{k1}$-Phe-(O)$_{k2}$—, Phe-CH=CH— and W$^4$W$^5$W$^6$Si—, in which W$^1$ denotes H, F, Cl, CN, CF$_3$, phenyl or alkyl having 1 to 5 C atoms, in particular H, F, Cl or CH$_3$, W$^2$ and W$^3$ each, independently of one another, denote H or alkyl having 1, 2, 3, 4 or 5 C atoms, in particular H, methyl, ethyl or n-propyl, W$^4$, W$^5$ and W$^6$ each, independently of one another, denote Cl, oxaalkyl or oxacarbonylalkyl having 1 to 5 C atoms, W$^7$ and W$^8$ each, independently of one another, denote H, Cl or alkyl having 1 to 5 C atoms, Phe denotes 1,4-phenylene, k$_1$, k$_2$ and k$_3$ each, independently of one another, denote 0 or 1, k$_3$ preferably denotes 1, and k$_4$ denotes an integer from 1 to 10.

Very particularly preferred groups P are selected from the group consisting of $CH_2=CW^1-CO-O-$, in particular $CH_2=CH-CO-O-$, $CH_2=C(CH_3)-CO-O-$ and $CH_2=CF-CO-O-$, furthermore $CH_2=CH-O-$, $(CH_2=CH)_2CH-O-CO-$, $(CH_2=CH)_2CH-O-$,

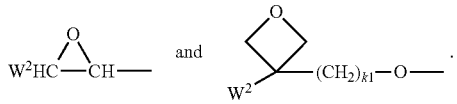

Further very particularly preferred groups P are selected from the group consisting of vinyloxy, acrylate, methacrylate, fluoroacrylate, chloroacrylate, oxetane, 3-ethyloxetane and epoxide groups, and particularly preferably denote an acrylate or methacrylate group.

Preferred spacer groups Sp are selected from the formula Sp"—X", so that the radical "P-Sp-" conforms to the formula "P-Sp"-X"—", where Sp" denotes alkylene having 1 to 20, preferably 1 to 12, C atoms, which is optionally mono- or polysubstituted by F, Cl, Br, I or CN and in which, in addition, one or more non-adjacent $CH_2$ groups may each be replaced, independently of one another, by —O—, —S—, —NH—, —N(R$^o$)—, —Si(R$^{oo}$R$^{ooo}$)—, —CO—, —CO—O—, —O—CO—, —O—CO—O—, —S—CO—, —CO—S—, —N(R$^{oo}$)—CO—O—, —O—CO—N(R$^{oo}$)—, —N(R$^{oo}$)—CO—N(R$^{oo}$)—, —CH=CH— or —C≡C— in such a way that O and/or S atoms are not linked directly to one another, X" denotes —O—, —S—, —CO—, —CO—O—, —O—CO—, —O—CO—O—, —CO—N(R$^{oo}$)—, —N(R$^{oo}$)—CO—, —N(R$^{oo}$)—CO—N(R$^{oo}$)—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=CR$^o$—, —CY$^2$=CY$^3$—, —C≡C—, —CH=CH—CO—O—, —O—CO—CH=CH— or a single bond, R$^{oo}$ and R$^{ooo}$ each, independently of one another, denote H or alkyl having 1 to 12 C atoms, and Y$^2$ and Y$^3$ each, independently of one another, denote H, F, Cl or CN.

X' is preferably —O—, —S—, —CO—, —COO—, —OCO—, —O—COO—, —CO—NR$^o$—, —NR$^o$—CO—, —NR—CO—NR$^o$— or a single bond.

Typical spacer groups Sp" are, for example, —(CH$_2$)$_{p1}$—, —(CH$_2$CH$_2$O)$_{q1}$—CH$_2$CH$_2$—, —CH$_2$CH$_2$—S—CH$_2$CH$_2$—, —CH$_2$CH$_2$—NH—CH$_2$CH$_2$— or —(SiR$^{oo}$R$^{ooo}$—O)$_{p1}$—, in which p1 is an integer from 1 to 12, q1 is an integer from 1 to 3, and R$^{oo}$ and R$^{ooo}$ have the meanings indicated above.

Particularly preferred groups -Sp"—X"— are —(CH$_2$)$_{p1}$—, —(CH$_2$)$_{p1}$—O—, —(CH$_2$)$_{p1}$—O—CO—, —(CH$_2$)$_{p1}$—O—CO—O—, in which p1 and q1 have the meanings indicated above.

Particularly preferred groups Sp" are, for example, in each case straight-chain ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methyliminoethylene, 1-methylalkylene, ethenylene, propenylene and butenylene.

In a further preferred embodiment of the invention, P in formula I denotes a radical containing two or more polymerisable groups (multifunctional polymerisable radicals). Suitable radicals of this type and polymerisable compounds containing them and the preparation thereof are described, for example, in U.S. Pat. No. 7,060,200 B1 or US 2006/0172090 A1. Particular preference is given to multifunctional polymerisable radicals selected from the following formulae:

| | |
|---|---|
| —X-alkyl-CHP$^1$—CH$_2$—CH$_2$P$^2$ | I*a |
| —X-alkyl-C(CH$_2$P$^1$)(CH$_2$P$^2$)—CH$_2$P$^3$ | I*b |
| —X-alkyl-CHP$^1$CHP$^2$—CH$_2$P$^3$ | I*c |
| —X-alkyl-C(CH$_2$P$^1$)(CH$_2$P$^2$)—C$_{aa}$H$_{2aa+1}$ | I*d |
| —X-alkyl-CHP$^1$—CH$_2$P$^2$ | I*e |
| —X-alkyl-CHP$^1$P$^2$ | I*f |
| —X-alkyl-CP$^1$P$^2$—C$_{aa}$H$_{2aa+1}$ | I*g |
| —X-alkyl-C(CH$_2$P$^1$)(CH$_2$P$^2$)—CH$_2$OCH$_2$—C(CH$_2$P$^3$)(CH$_2$P$^4$)CH$_2$P$^5$ | I*h |
| —X-alkyl-CH((CH$_2$)$_{aa}$P$^1$)((CH$_2$)$_{bb}$P$^2$) | I*i |
| —X-alkyl-CHP$^1$CHP$^2$—C$_{aa}$H$_{2aa+1}$ | I*k |
| —X'-alkyl-C(CH$_3$)(CH$_2$P$^1$)(CH$_2$P$^2$) | I*m | in which alkyl denotes a single bond or straight-chain or branched alkylene having 1 to 12 C atoms, in which one or more non-adjacent CH$_2$ groups may each be replaced, independently of one another, by —C(R$^{oo}$)=C(R$^{ooo}$)—, —C≡C—, —N(R$^{oo}$)—, —O—, —S—, —CO—, —CO—O—, —O—CO—, —O—CO—O— in such a way that O and/or S atoms are not linked directly to one another and in which, in addition, one or more H atoms may be replaced by F, Cl or CN, where R$^{oo}$ and R$^{ooo}$ have the meanings indicated above, aa and bb each, independently of one another, denote 0, 1, 2, 3, 4, 5 or 6, X has one of the meanings indicated for X', and P$^{1-5}$ each, independently of one another, have one of the meanings indicated for P.

The polymerisable compounds of the formula I are characterised in that at least one of the radicals Z$^1$ and Z$^2$ present in the compounds denotes a CC triple bond. Surprisingly, it has been found that, on use of these compounds in LC media and PSA displays according to the invention, the desired pretilt can be achieved particularly quickly and the production time of the display can be significantly shortened. The polymerisable compounds according to the invention exhibit a significantly faster polymerisation rate in the PSA displays, meaning that fewer unreacted residual amounts remain in the LC cell, improving the electro-optical properties thereof and simplifying controlled reaction of these residual amounts.

Particular preference is given to compounds of the formula I in which

A$^1$, A$^2$, A$^3$ each, independently of one another, denote 1,4-phenylene, naphthalene-2,6-diyl, phenanthrene-2,7-diyl or anthracene-2,7-diyl, where all these groups may be unsubstituted or mono- or polysubstituted by L, L denotes P—, P-Sp-, OH, CH$_2$OH, F, Cl, Br, I, —CN, —NO$_2$, —NCO, —NCS, —OCN, —SCN, —C(=O)N(R$^x$)$_2$, —C(=O)Y$^1$, —C(=O)R$^x$, —N(R$^x$)$_2$, optionally substituted silyl, optionally substituted aryl having 6 to 20 C atoms, straight-chain or branched alkyl or alkoxy having 1 to 25, preferably 1 to 12, C atoms, or straight-chain or branched alkenyl, alkynyl, alkylcarbonyl, alkoxycarbonyl, alkylcarbonyloxy or alkoxycarbonyloxy having 2 to 25, preferably 2 to 12, C atoms, in which, in addition, one or more H atoms in all these groups may be replaced by F, Cl, P— or P-Sp-, $Y^1$ denotes halogen, and $R^x$ denotes P—, P-Sp-, H, halogen, straight-chain, branched or cyclic alkyl having 1 to 25, preferably 1 to 12, C atoms, in which, in addition, one or more non-adjacent $CH_2$ groups may be replaced by —O—, —S—, —CO—, —CO—O—, —O—CO—, —O—CO—O— in such a way that O and/or S atoms are not linked directly to one another, and in which, in addition, one or more H atoms may be replaced by F, Cl, P— or P-Sp-.

Further preferred compounds of the formula I and sub-formulae thereof indicated above and below are selected from one or more of the following preferred embodiments, which can be combined with one another as desired, in which P on each occurrence, identically or differently, denotes acrylate ($CH_2$=CH—C(O)—O—) or methacrylate ($CH_2$=C($CH_3$)—C(O)—O—), s1 denotes 1 and s2 denotes 0 or s1 denotes 0 and s2 denotes 1, s1 and s2 denote 0, Sp denotes —$(CH_2)_{p1}$—, —$(CH_2)_{p1}$—O—, —$(CH_2)_{p1}$—O—CO— or —$(CH_2)_{p1}$—O—CO—O—, preferably —$(CH_2)_{p1}$— or —$(CH_2)_{p1}$—O—, in which p1 denotes an integer from 1 to 12, preferably from 1 to 5, particularly preferably from 1 to 3, Sp and/or Sp" denote an alkylene radical having 1 to 5, preferably 1 to 3, C atoms, $A^1$, $A^2$ and $A^3$ each, independently of one another and on each occurrence identically or differently, denote phenylene-1,4-diyl or naphthalene-2,6-diyl, which may also be mono- or polysubstituted by L as described above and below, L neither denotes nor contains a polymerisable group, L denotes an unpolymerisable group, preferably selected from F, Cl, —CN and straight-chain or branched alkyl having 1 to 25, particularly preferably 1 to 10, C atoms, in which, in addition, one or more non-adjacent $CH_2$ groups may each be replaced, independently of one another, by —C($R^{00}$)=C($R^{000}$)—, —C≡C—, —N($R^{00}$)—, —O—, —S—, —CO—, —CO—O—, —O—CO—, —O—CO—O— in such a way that O and/or S atoms are not linked directly to one another, and in which, in addition, one or more H atoms may be replaced by F, Cl, Br, I or CN, L denotes F, Cl, Br, I, —CN, —$NO_2$, —NCO, —NCS, —OCN or —SCN, preferably F, L denotes straight-chain or branched alkyl or alkoxy having 1 to 12 C atoms, or straight-chain or branched alkenyl, alkynyl, alkylcarbonyl, alkoxycarbonyl, alkylcarbonyloxy or alkoxycarbonyloxy having 2 to 12 C atoms, in which, in addition, one or more H atoms in all these groups may be replaced by F, Cl or P-Sp-, L denotes P— or P-Sp-, at least one of the radicals $Z^1$ and $Z^2$ denotes —C≡C— and the other radicals $Z^1$ and $Z^2$ each, independently of one another, denote —C≡C—, —CO—O—, —O—CO— or a single bond, at least one of the radicals $Z^1$ and $Z^2$ denotes —C≡C— and the other radicals $Z^1$ and $Z^2$ each, independently of one another, denote —C≡C— or a single bond, all radicals $Z^1$ and $Z^2$ occurring in the compounds of the formula I denote —C≡C—, m denotes 0 or 1, m denotes 0, m denotes 1 and $Z^2$ denotes —CO—O— or —O—CO—, m denotes 1 and $Z^2$ denotes —C≡C— or a single bond.

Particularly preferred compounds of the formula I are selected from the group consisting of the following sub-formulae:

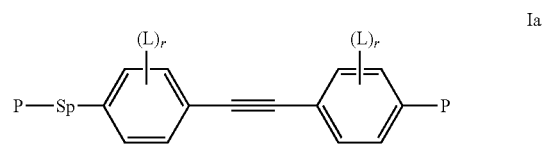

Ia

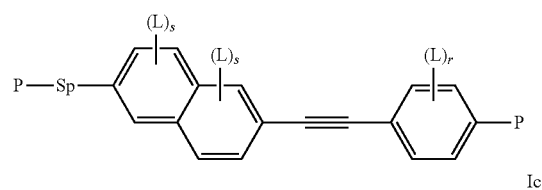

Ib

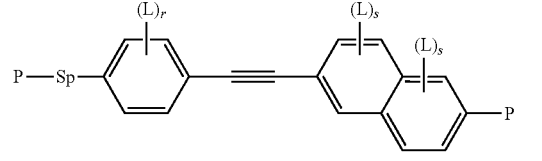

Ic

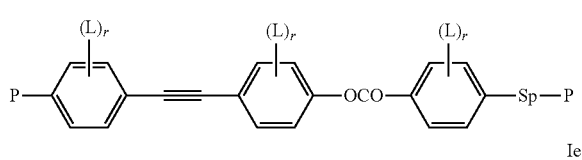

Id

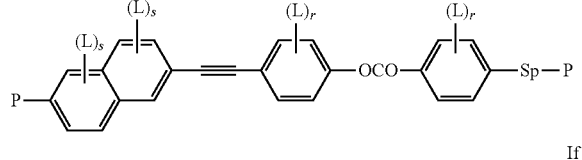

Ie

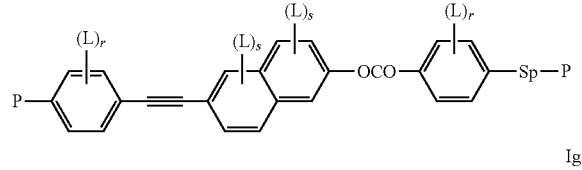

If

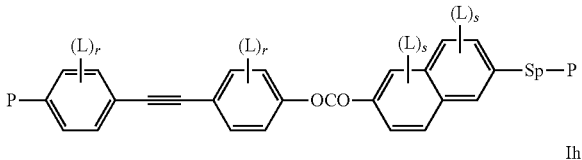

Ig

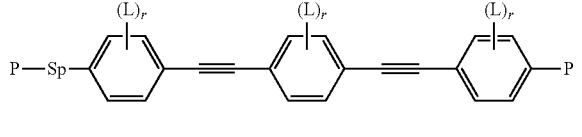

Ih

-continued

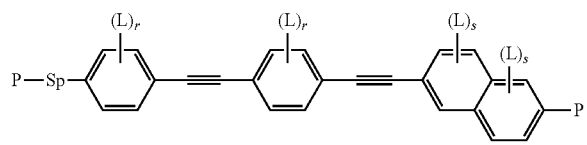
Ii

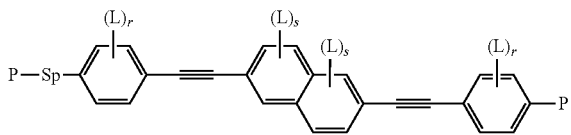
Ik

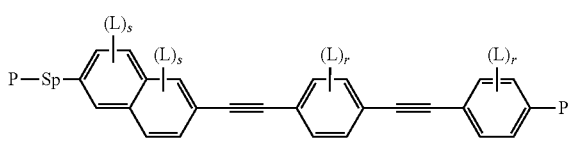
Im

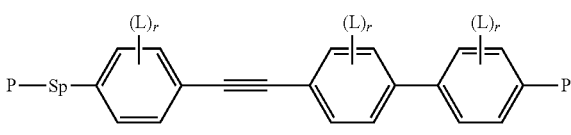
In

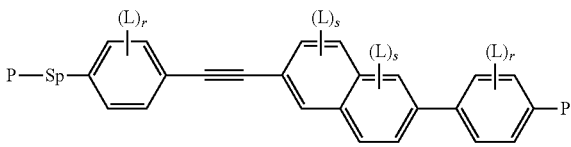
Io

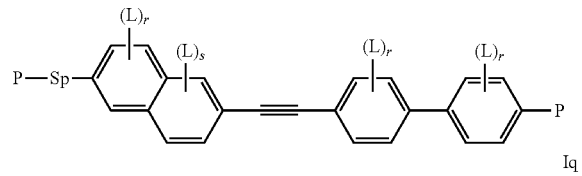
Ip

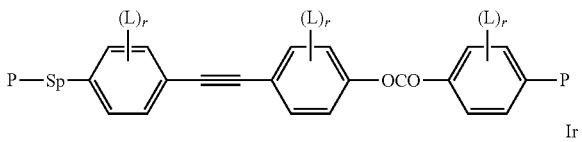
Iq

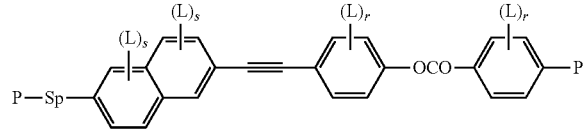
Ir

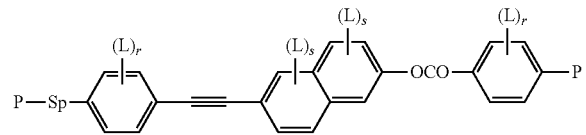
Is

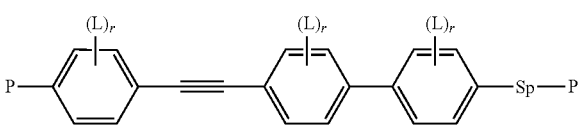
Iu

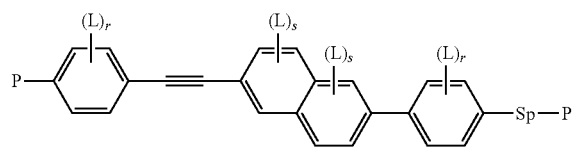
Iv

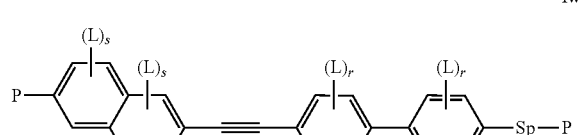
Iw in which P, Sp and L have one of the meanings indicated above and below, r denotes 0, 1, 2, 3 or 4, and s denotes 0, 1, 2 or 3.

P in the compounds of the formula I and the sub-formulae Ia-Ip preferably denotes acrylate or methacrylate, furthermore fluoroacrylate.

Sp in the compounds of the formula I and the sub-formulae Ia-Ip preferably denotes —(CH$_2$)$_{p1}$—, —(CH$_2$)$_{p1}$—O—, —(CH$_2$)$_{p1}$—O—CO— or —(CH$_2$)$_{p1}$—O—CO—O— or mirror images thereof, in which p1 denotes an integer from 1 to 12, preferably from 1 to 6, particularly preferably 1, 2, 3 or 4, and where the linking to the adjacent benzene ring takes place via the O atom.

The invention furthermore relates to novel compounds of the formula I.

The invention furthermore relates to novel intermediates for the preparation of compounds of the formula I, selected from formula II G-O-(Sp)$_{s1}$-A$^1$-Z$^1$-A$^2$(-Z$^2$-A$^3$)$_m$-(Sp)$_{s2}$-O-G'    II in which Sp, s1, s2, A$^1$, A$^2$, A$^3$, Z$^1$, Z$^2$ and m have the meanings indicated in formula I or above and below, and G and G' each, independently of one another, denote an H atom or a protecting group.

Suitable protecting groups G are known to the person skilled in the art. Preferred protecting groups are alkyl, acyl and alkylsilyl or arylsilyl groups, 2-tetrahydropyranyl or methoxymethyl.

Particularly preferred intermediates of the formula II are selected from the group consisting of the above-mentioned sub-formulae Ia-Ip in which "P—" in each case denotes G-O— and "—P" in each case denotes —O-G', where G and G' preferably denote H.

Particularly suitable and preferred processes for the preparation of compounds and intermediates of the formulae I and II and sub-formulae thereof are depicted by way of example in the following schemes and preferably comprise one or more of the steps described below.

The compounds and intermediates of the formulae I and II and sub-formulae thereof can be prepared analogously to processes known to the person skilled in the art and described in standard works of organic chemistry, such as, for example, in Houben-Weyl, Methoden der organischen Chemie [Methods of Organic Chemistry], Thieme-Verlag, Stuttgart.

For example, compounds of the formula I are synthesised by esterification or etherification of the intermediates of the formula II using corresponding acids, acid derivatives, or halogenated compounds containing a group P. As depicted by way of example in Scheme 1, compounds of the formula I in which P is, for example, an acrylate or methacrylate group can be obtained by esterification of the corresponding alcohols of the formula II in which G=G'=H using acid derivatives, such as, for example, (meth)acryloyl chloride or (meth)acrylic anhydride, in the presence of a base and optionally 4-(N,N-dimethylamino)pyridine (DMAP). Furthermore, the alcohols can also be esterified using (meth)acrylic acid in the presence of a dehydrating agent, for example by the Steglich method using dicyclohexylcarbodiimide (DCC).

The invention thus furthermore relates to a process for the preparation of a compound of the formula I in which a compound of the formula II is esterified or etherified using corresponding acids, acid derivatives, or halogenated compounds containing a group P, in the presence of a dehydrating reagent.

Scheme 1

HO—(Sp)$_{s1}$—A$^1$—Z$^1$—A$^2$(—Z$^2$—A$^3$)$_m$—(Sp)$_{s2}$—OH

↓

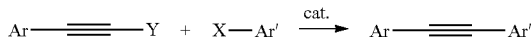

(R = H or CH$_3$; Sp, s1, s2, L, A$^{1-3}$, Z$^{1-2}$, m as defined in formula II)

The synthesis of the tolan skeleton in the compounds of the formulae I and II is carried out by processes known to the person skilled in the art and described in the literature. Some particularly suitable variants are depicted by way of example below (Scheme 2): thus, aryl halides and triflates (X=Hal, OSO$_2$CF$_3$) can be converted into tolans and analogous diarylacetylenes in a multiplicity of transition metal-catalysed cross-coupling reactions, for example by the Sonogashira method (Y=H, see, for example, R. Chinchilla, C. Najera, Chem. Rev. 2007, 107, 874-922; J. Tsuji, Palladium Reagent and Catalysts; Wiley: New York, 1995), by the Stille method (Y=Sn(alkyl)$_3$, see, for example, V. Farina, V. Krishna-murthy, W. J. Scott, The Stille Reaction. Organic Reactions (Hoboken, N.J., United States) (1997), Vol. 50), in reactions of the Kumada type (Y=MgHal, T. Kamikawa, T. Hayashi, J. Org. Chem. 1998, 63(24), 8922-8925) or by the Negishi method (Y=ZnHal, see, for example, R. Rossi et al., Tetrahedron 59 (2003) 2067-2081).

Scheme 2

Ar—≡≡—Y + X—Ar' $\xrightarrow{cat.}$ Ar—≡≡—Ar'

The arylacetylenes are themselves accessible by Sonogashira coupling to silylacetylenes (Scheme 3). The arylsilylacetylenes obtained in a first step are deprotected, for example using tetrabutylammonium fluoride or Olah's reagent, to give the target compounds.

Scheme 3

R$_3$Si—≡≡—H + X—Ar' $\xrightarrow{cat.}$
R$_3$Si—≡≡—Ar ⟶ H—≡≡—Ar

Further access to arylacetylenes is provided by the reaction of arylcarbaldehydes by the Corey and Fuchs method (Tetrahedron Lett. 1972, 36, 3769-3772; Scheme 4).

Scheme 4

Ar—CHO ⟶ A—≡≡—H

For the formal elimination of water from ketoenols to give terminal alkynes (Scheme 5), see, for example, E. Negishi et al., Organic Syntheses, 1986, 64, 44-49; I. M. Lyapkalo, Synlett 2009, 4, 558-561.

Scheme 5

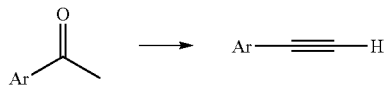

The invention furthermore relates to the processes described above and below for the preparation of compounds of the formulae I and II, in particular for the preparation of compounds of the formula I from compounds of the formula II.

For the production of PSA displays, the polymerisable compounds are polymerised or crosslinked (if one compound contains two or more polymerisable groups) by in-situ polymerisation in the LC medium between the substrates of the LC display with application of a voltage. The polymerisation can be carried out in one step. It is also possible firstly to carry out the polymerisation with application of a voltage in a first step in order to produce a pretilt angle, and subsequently, in a second polymerisation step without an applied voltage, to polymerise or crosslink the compounds which have not reacted in the first step ("end curing").

Suitable and preferred polymerisation methods are, for example, thermal or photopolymerisation, preferably photopolymerisation, in particular UV photopolymerisation. One or more initiators can optionally also be added here. Suitable conditions for the polymerisation and suitable types and amounts of initiators are known to the person skilled in the art and are described in the literature. Suitable for free-radical polymerisation are, for example, the commercially available photoinitiators Irgacure651®, Irgacure184®, Irgacure907®, Irgacure369® or Darocure1173® (Ciba AG). If an initiator is employed, its proportion is preferably 0.001 to 5% by weight, particularly preferably 0.001 to 1% by weight.

The polymerisable compounds according to the invention are also suitable for polymerisation without an initiator, which is accompanied by considerable advantages, such, for example, lower material costs and in particular less contamination of the LC medium by possible residual amounts of the initiator or degradation products thereof. The polymerisation can thus also be carried out without the addition of an initiator. In a preferred embodiment, the LC medium thus comprises no polymerisation initiator.

The polymerisable component A) or the LC medium may also comprise one or more stabilisers in order to prevent undesired spontaneous polymerisation of the RMs, for example during storage or transport. Suitable types and amounts of stabilisers are known to the person skilled in the art and are described in the literature. Particularly suitable are, for example, the commercially available stabilisers from the Irganox® series (Ciba AG), such as, for example, Irganox® 1076. If stabilisers are employed, their proportion, based on the total amount of RMs or the polymerisable component A), is preferably 10-10,000 ppm, particularly preferably 50-500 ppm.

The LC media according to the invention for use in PSA displays preferably comprise <5% by weight, particularly preferably <1% by weight, very particularly preferably <0.5% by weight, of polymerisable compounds, in particular polymerisable compounds of the above-mentioned formula I and sub-formulae thereof.

Particular preference is given to LC media comprising one, two or three polymerisable compounds according to the invention.

Preference is furthermore given to LC media in which the polymerisable component (component A) comprises exclusively polymerisable compounds according to the invention.

Preference is furthermore given to LC media in which component B) is an LC compound or an LC mixture which has a nematic liquid-crystal phase.

Preference is furthermore given to achiral polymerisable compounds according to the invention and LC media in which the compounds of component A) and/or B) are selected exclusively from the group consisting of achiral compounds.

Preference is furthermore given to LC media in which the polymerisable component or component A) comprises one or more polymerisable compounds according to the invention containing one polymerisable group (monoreactive) and one or more polymerisable compounds according to the invention containing two or more, preferably two, polymerisable groups (di- or multireactive).

Preference is furthermore given to PSA displays and LC media in which the polymerisable component or component A) comprises exclusively polymerisable compounds according to the invention containing two polymerisable groups (direactive).

The proportion of the polymerisable component or component A) in the LC media according to the invention is preferably <5%, particularly preferably <1%, very particularly preferably <0.5%.

The proportion of the liquid-crystalline component or component B) in the LC media according to the invention is preferably >95%, particularly preferably >99%.

The polymerisable compounds according to the invention can be polymerised individually, but it is also possible to polymerise mixtures which comprise two or more polymerisable compounds according to the invention, or mixtures comprising one or more polymerisable compounds according to the invention and one or more further polymerisable compounds (comonomers), which are preferably mesogenic or liquid-crystalline. In the case of polymerisation of such mixtures, copolymers form. The invention furthermore relates to the polymerisable mixtures mentioned above and below. The polymerisable compounds and comonomers are mesogenic or non-mesogenic, preferably mesogenic or liquid-crystalline.

Suitable and preferred mesogenic comonomers, particularly for use in PSA displays, are selected, for example, from the following formulae:

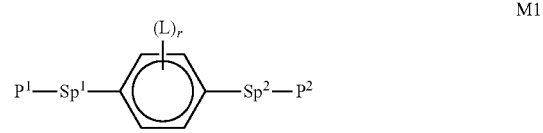

M1

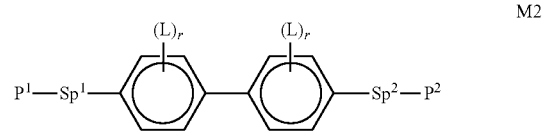

M2

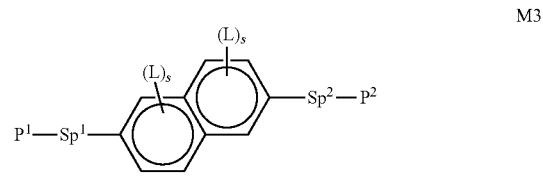

M3

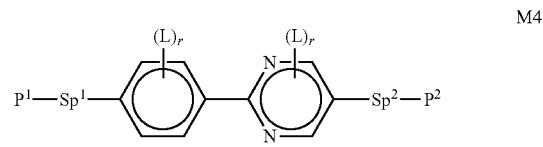

M4

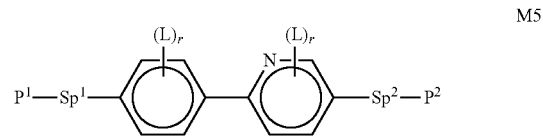

M5

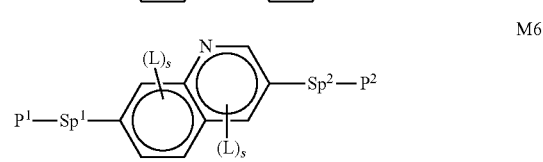

M6

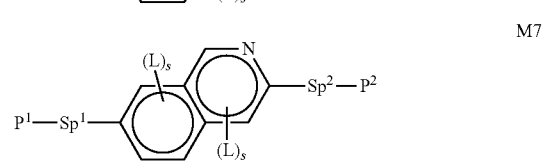

M7

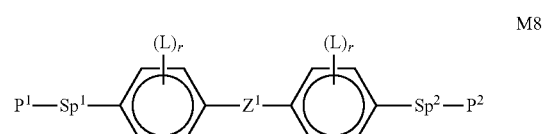

M8

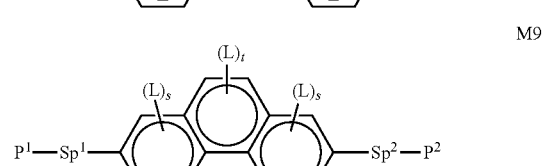

M9

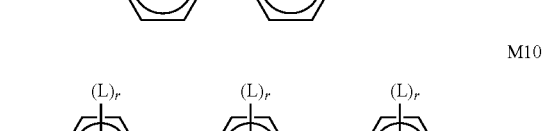

M10

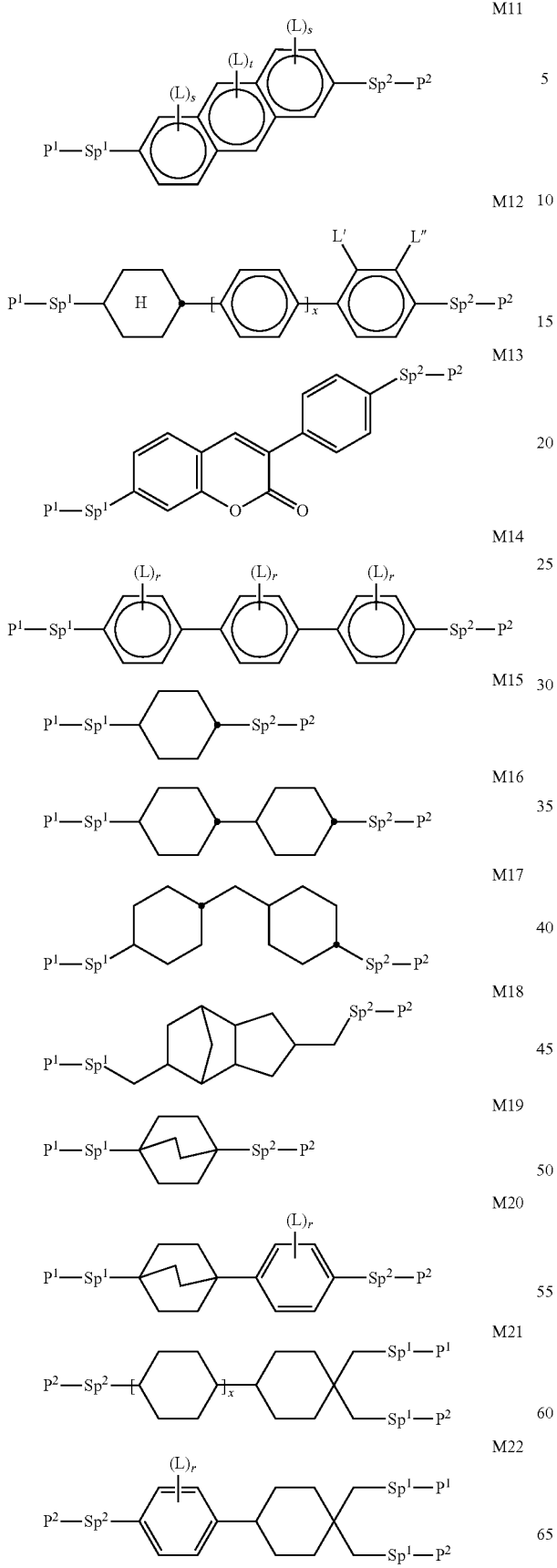
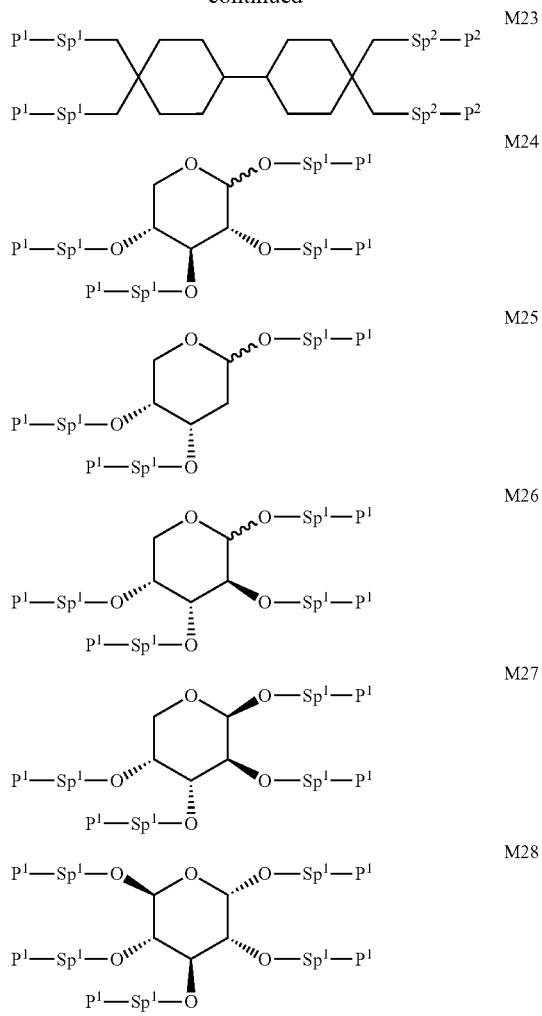

in which the individual radicals have the following meanings:

$P^1$ and $P^2$ each, independently of one another, denote a polymerisable group, preferably having one of the meanings indicated above and below for P, particularly preferably an acrylate, methacrylate, fluoroacrylate, oxetane, vinyloxy or epoxide group, $Sp^1$ and $Sp^2$ each, independently of one another, denote a single bond or a spacer group, preferably having one of the meanings indicated above and below for Sp, and particularly preferably denote $-(CH_2)_{p1}-$, $-(CH_2)_{p1}-O-$, $-(CH_2)_{p1}-CO-O-$ or $-(CH_2)_{p1}-O-CO-O-$, in which p1 is an integer from 1 to 12, and where the linking to the adjacent ring in the last-mentioned groups takes place via the O atom, where, in addition, one or more of the radicals $P^1$-$Sp^1$- and $P^2$-$Sp^2$- may denote $R^{aa}$, with the proviso that at least one of the radicals $P^1$-$Sp^1$- and $P^2$-$Sp^2$- present does not denote $R^{aa}$, $R^{aa}$ denotes H, F, Cl, CN or straight-chain or branched alkyl having 1 to 25 C atoms, in which, in addition, one or more non-adjacent $CH_2$ groups may each be replaced, independently of one another, by $C(R^0)=C(R^{00})-$, $-C\equiv C-$, $-N(R^0)-$, $-O-$, $-S-$, $-CO-$, $-CO-O-$, $-O-CO-$, $-O-CO-O-$ in such a way that O and/or S atoms are not linked directly to one another, and in which, in addition, one or more H atoms may be replaced by F, Cl, CN or P¹-Sp¹-, particularly preferably straight-chain or branched, optionally mono- or polyfluorinated alkyl, alkoxy, alkenyl, alkynyl, alkylcarbonyl, alkoxycarbonyl, alkylcarbonyloxy or alkoxycarbonyloxy having 1 to 12 C atoms (where the alkenyl and alkynyl radicals have at least two C atoms and the branched radicals have at least three C atoms), $R^O$, $R^{OO}$ each, independently of one another and identically or differently on each occurrence, denote H or alkyl having 1 to 12 C atoms, $R^y$ and $R^z$ each, independently of one another, denote H, F, $CH_3$ or $CF_3$, $Z^1$ denotes —O—, —CO—, —C($R^yR^z$)— or —$CF_2CF_2$—, $Z^2$ and $Z^3$ each, independently of one another, denote —CO—O—, —O—CO—, —$CH_2$O—, —O$CH_2$—, —$CF_2$O—, —O$CF_2$— or —$(CH_2)_n$—, where n is 2, 3 or 4, L on each occurrence, identically or differently, denotes F, Cl, CN or straight-chain or branched, optionally mono- or polyfluorinated alkyl, alkoxy, alkenyl, alkynyl, alkylcarbonyl, alkoxycarbonyl, alkylcarbonyloxy or alkoxycarbonyloxy having 1 to 12 C atoms, preferably F, L' and L" each, independently of one another, denote H, F or Cl, r denotes 0, 1, 2, 3 or 4, s denotes 0, 1, 2 or 3, t denotes 0, 1 or 2, x denotes 0 or 1.

Besides the polymerisable compounds described above, the LC media for use in the LC displays according to the invention comprise an LC mixture ("host mixture") comprising one or more, preferably two or more, low-molecular-weight (i.e. monomeric or unpolymerised) compounds. The latter are stable or unreactive to a polymerisation reaction under the conditions used for polymerisation of the polymerisable compounds. In principle, any LC mixture which is suitable for use in conventional VA and OCB displays is suitable as host mixture. Suitable LC mixtures are known to the person skilled in the art and are described in the literature, for example mixtures in VA displays in EP 1 378 557 A1 and mixtures for OCB displays in EP 1 306 418 A1 and DE 102 24 046 A1.

In a first preferred embodiment of the present invention, the LC medium comprises an LC host mixture based on compounds having negative dielectric anisotropy. Such LC media are particularly suitable for use in PSA-VA displays. Particularly preferred embodiments of LC media of this type are mentioned in sections a)-x) below:

a) LC medium which comprises one or more compounds selected from the group consisting of the formulae CY and/or PY:

in which the individual radicals have the following meanings:

a denotes 1 or 2, b denotes 0 or 1,

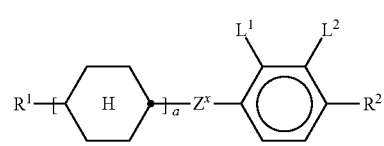

$R^1$ and $R^2$ each, independently of one another, denote alkyl having 1 to 12 C atoms, where, in addition, one or two non-adjacent $CH_2$ groups may be replaced by —O—, —CH=CH—, —CO—, —OCO— or —COO— in such a way that O atoms are not linked directly to one another, preferably alkyl or alkoxy having 1 to 6 C atoms, $Z^x$ and $Z^y$ each, independently of one another, denote —$CH_2CH_2$—, —CH=CH—, —$CF_2$O—, —O$CF_2$—, —$CH_2$O—, —O$CH_2$—, —CO—O—, —O—CO—, —$C_2F_4$—, —CF=CF—, —CH=CH—$CH_2$O— or a single bond, preferably a single bond, $L^{1-4}$ each, independently of one another, denote F, Cl, $OCF_3$, $CF_3$, $CH_3$, $CH_2F$, $CHF_2$.

Preferably, both radicals $L^1$ and $L^2$ denote F or one of the radicals $L^1$ and $L^2$ denotes F and the other denotes Cl, or both radicals $L^3$ and $L^4$ denote F or one of the radicals $L^3$ and $L^4$ denotes F and the other denotes Cl.

The compounds of the formula CY are preferably selected from the group consisting of the following sub-formulae:

CY1

CY2

CY3

CY4

CY5

-continued
CY6
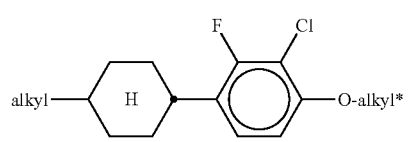
CY7
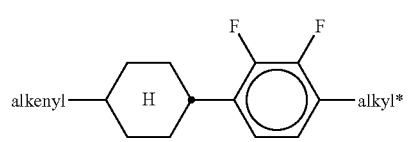
CY8
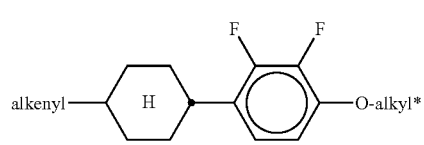
CY9
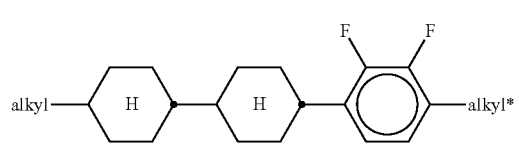
CY10
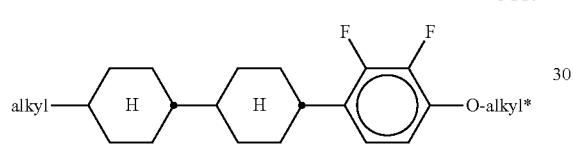
CY11
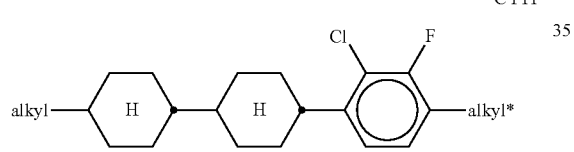
CY12
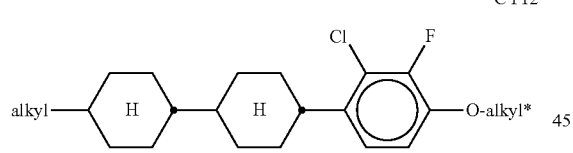
CY13
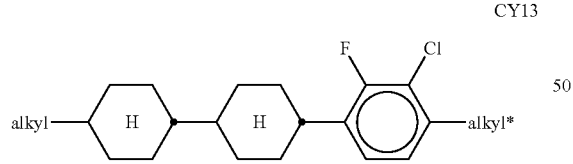
CY14
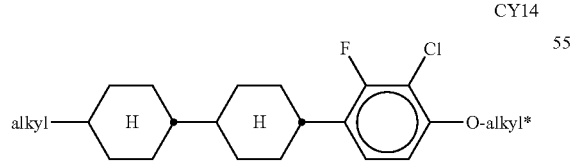
CY15
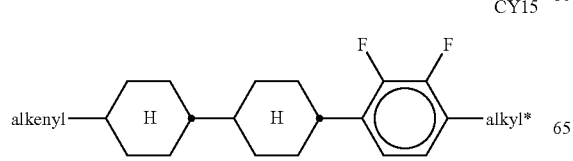
-continued
CY16
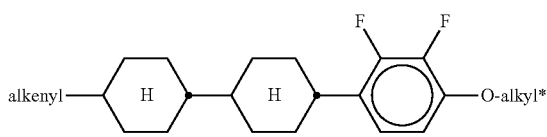
CY17
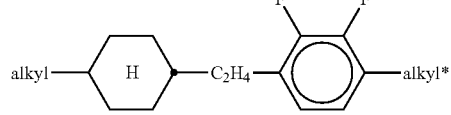
CY18
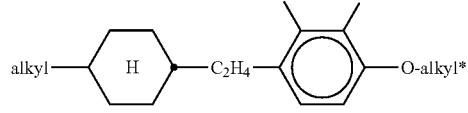
CY19
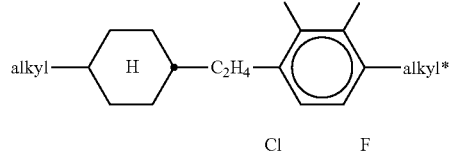
CY20
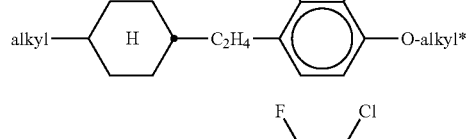
CY21
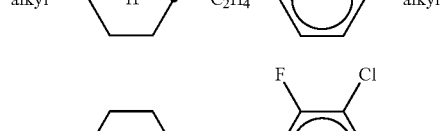
CY22
CY23
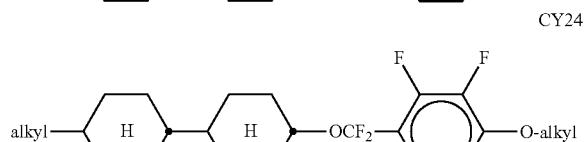
CY24
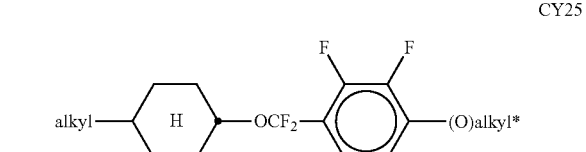
CY25
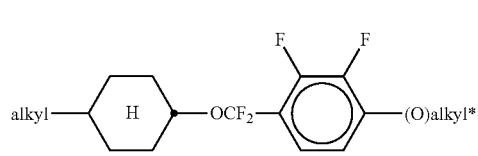
CY25

-continued

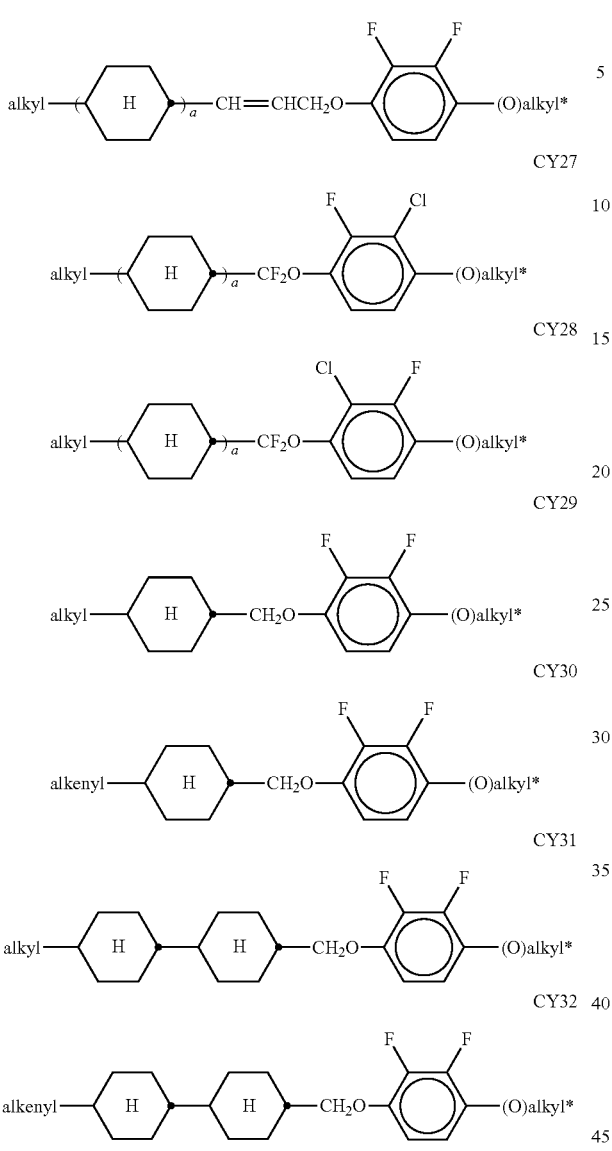

in which a denotes 1 or 2, alkyl and alkyl* each, independently of one another, denote a straight-chain alkyl radical having 1-6 C atoms, and alkenyl denotes a straight-chain alkenyl radical having 2-6 C atoms, and (O) denotes an oxygen atom or a single bond. Alkenyl preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

The compounds of the formula PY are preferably selected from the group consisting of the following sub-formulae:

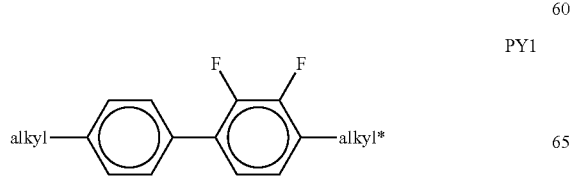

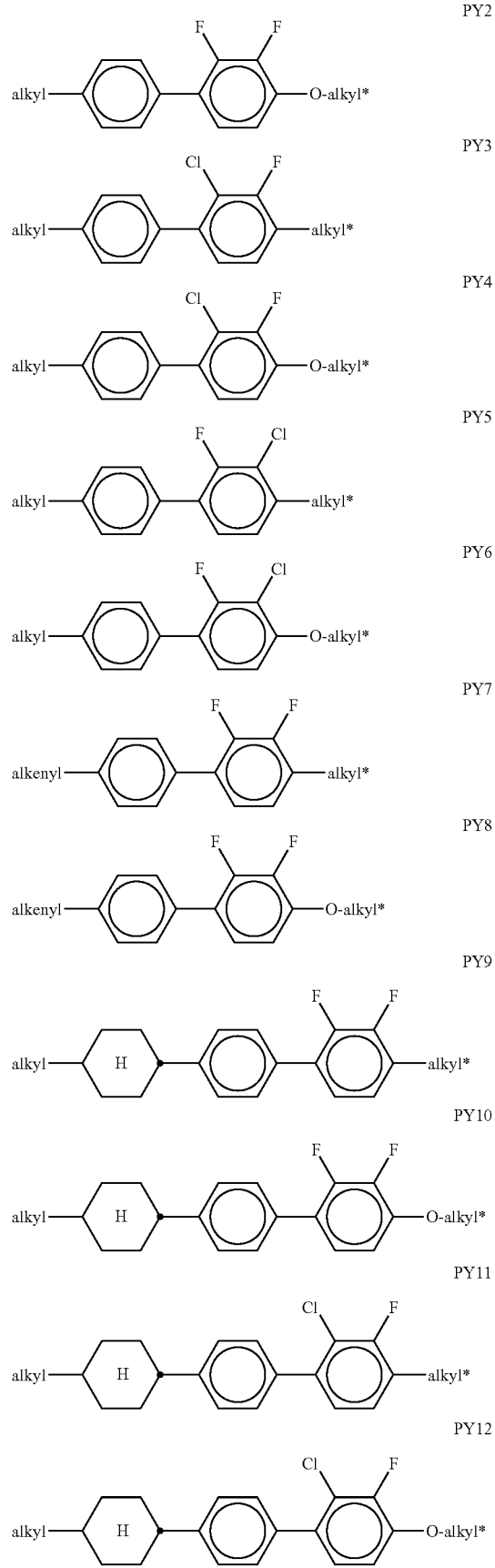

-continued

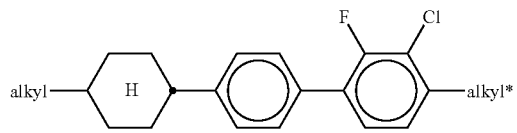
PY13

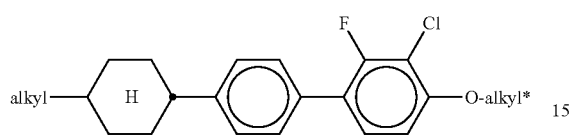
PY14

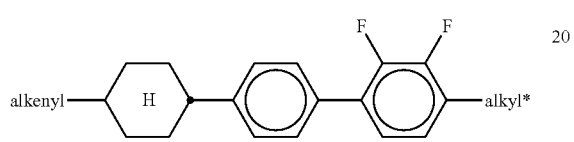
PY15

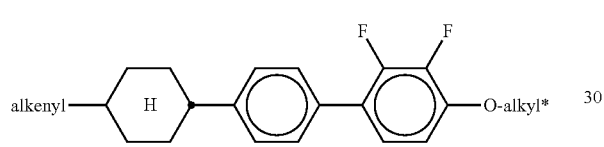
PY16

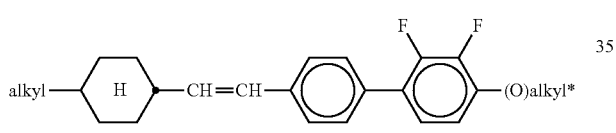
PY17

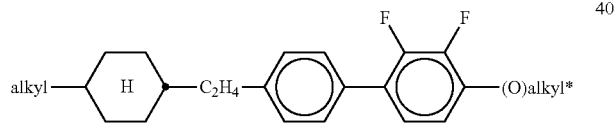
PY18

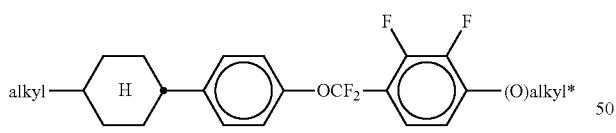
PY19

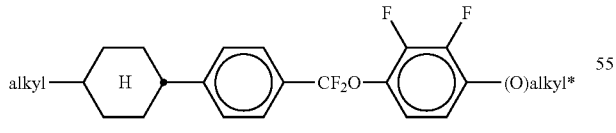
PY20 in which alkyl and alkyl* each, independently of one another, denote a straight-chain alkyl radical having 1-6 C atoms, and alkenyl denotes a straight-chain alkenyl radical having 2-6 C atoms, and (O) denotes an oxygen atom or a single bond. Alkenyl preferably denotes $CH_2$=CH—, $CH_2$=CHCH$_2$CH$_2$—, $CH_3$—CH=CH—, $CH_3$—CH$_2$—CH=CH—, $CH_3$—(CH$_2$)$_2$—CH=CH—, $CH_3$—(CH$_2$)$_3$—CH=CH— or $CH_3$—CH=CH—(CH$_2$)$_2$—.

b) LC medium which additionally comprises one or more compounds of the following formula:

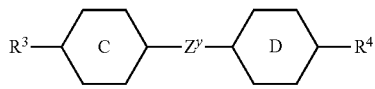
ZK in which the individual radicals have the following meanings:

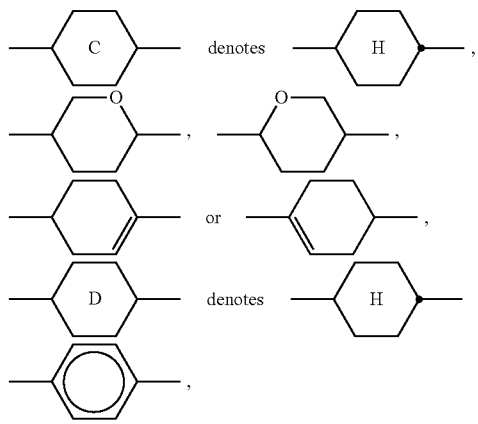

$R^3$ and $R^4$ each, independently of one another, denote alkyl having 1 to 12 C atoms, in which, in addition, one or two non-adjacent $CH_2$ groups may be replaced by —O—, —CH=CH—, —CO—, —O—CO— or —CO—O— in such a way that O atoms are not linked directly to one another, $Z^y$ denotes —CH$_2$CH$_2$—, —CH=CH—, —CF$_2$O—, —OCF$_2$—, —CH$_2$O—, —OCH$_2$—, —CO—O—, —O—CO—, —C$_2$F$_4$—, —CF=CF—, —CH=CH—CH$_2$O— or a single bond, preferably a single bond.

The compounds of the formula ZK are preferably selected from the group consisting of the following sub-formulae:

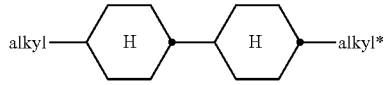
ZK1

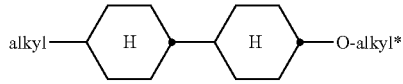
ZK2

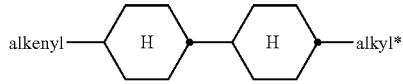
ZK3

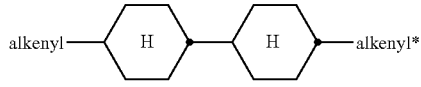
ZK4

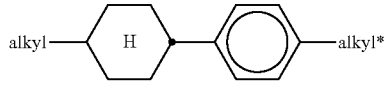
ZK5

-continued

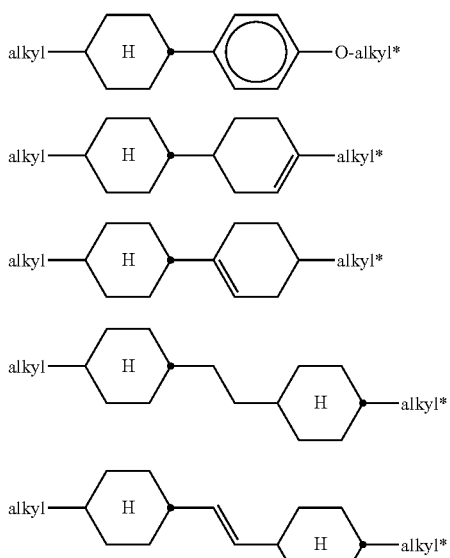

in which alkyl and alkyl* each, independently of one another, denote a straight-chain alkyl radical having 1-6 C atoms, and alkenyl denotes a straight-chain alkenyl radical having 2-6 C atoms. Alkenyl preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

c) LC medium which additionally comprises one or more compounds of the following formula:

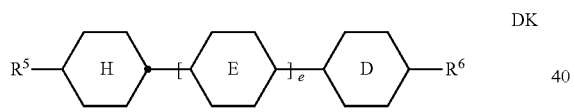

in which the individual radicals on each occurrence, identically or differently, have the following meanings:

$R^5$ and $R^6$ each, independently of one another, have one of the meanings indicated above for $R^1$,

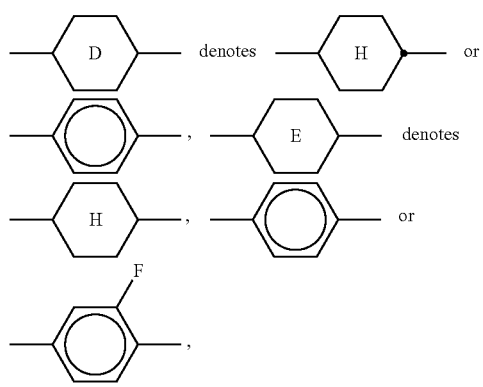

and e denotes 1 or 2.

The compounds of the formula DK are preferably selected from the group consisting of the following sub-formulae:

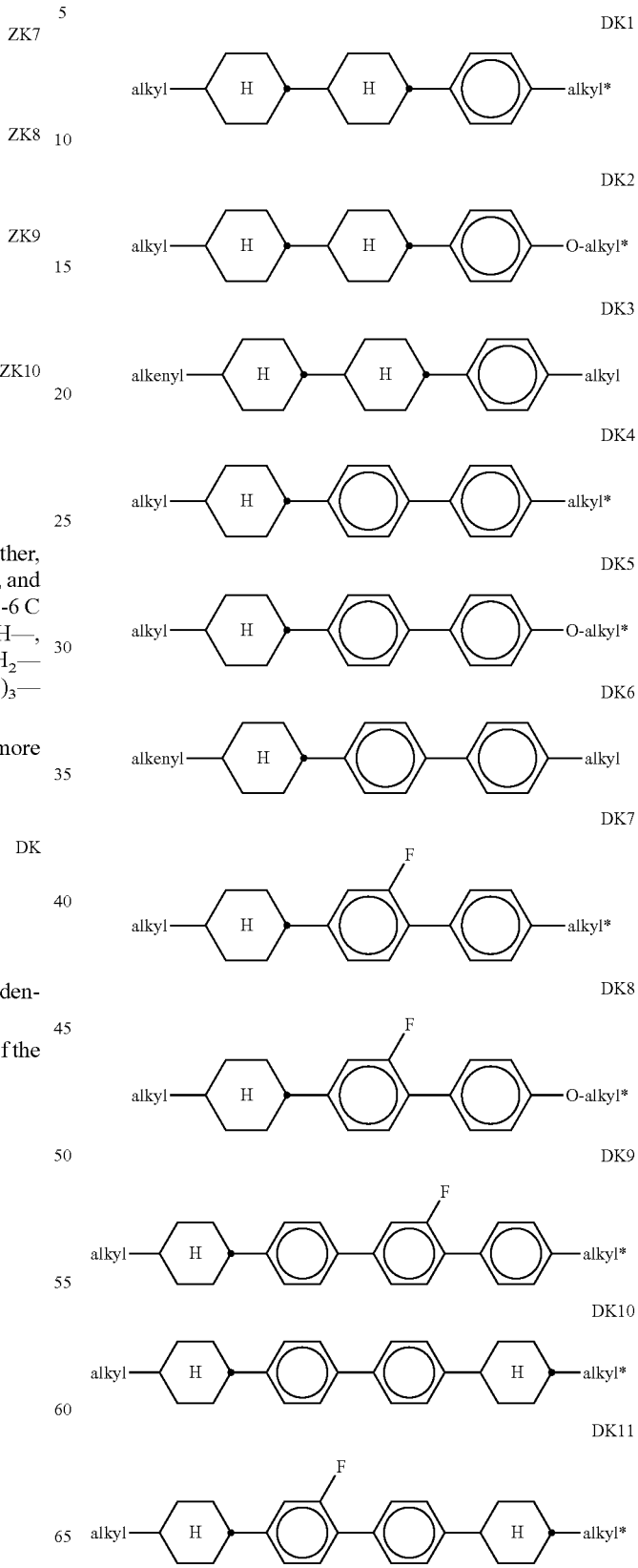

-continued

DK12

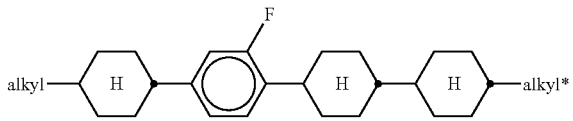

in which alkyl and alkyl* each, independently of one another, denote a straight-chain alkyl radical having 1-6 C atoms, and alkenyl and alkenyl* each, independently of one another, denote a straight-chain alkenyl radical having 2-6 C atoms. Alkenyl and alkenyl* preferably denote CH$_2$=CH—, CH$_2$=CHCH$_2$CH$_2$—, CH$_3$—CH=CH—, CH$_3$—CH$_2$—CH=CH—, CH$_3$—(CH$_2$)$_2$—CH=CH—, CH$_3$—(CH$_2$)$_3$—CH=CH— or CH$_3$—CH=CH—(CH$_2$)$_2$—.

d) LC medium which additionally comprises one or more compounds of the following formula:

LY

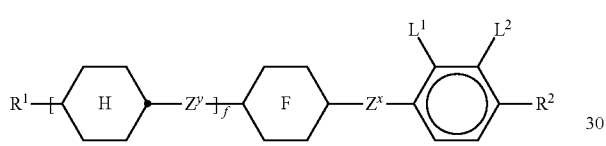

in which the individual radicals have the following meanings:

 denotes 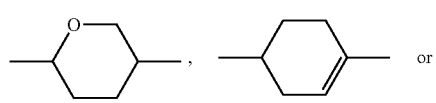,

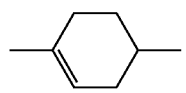

f denotes 0 or 1,
R$^1$ and R$^2$ each, independently of one another, denote alkyl having 1 to 12 C atoms, where, in addition, one or two non-adjacent CH$_2$ groups may be replaced by —O—, —CH=CH—, —CO—, —OCO— or —COO— in such a way that O atoms are not linked directly to one another,
Z$^x$ and Z$^y$ each, independently of one another, denote —CH$_2$CH$_2$—, —CH=CH—, —CF$_2$O—, —OCF$_2$—, —CH$_2$O—, —OCH$_2$—, —CO—O—, —O—CO—, —C$_2$F$_4$—, —CF=CF—, —CH=CH—CH$_2$O— or a single bond, preferably a single bond,
L$^1$ and L$^2$ each, independently of one another, denote F, Cl, OCF$_3$, CF$_3$, CH$_3$, CH$_2$F, CHF$_2$.
Preferably, both radicals L$^1$ and L$^2$ denote F or one of the radicals L$^1$ and L$^2$ denotes F and the other denotes Cl.

The compounds of the formula LY are preferably selected from the group consisting of the following sub-formulae:

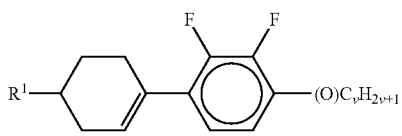 LY1

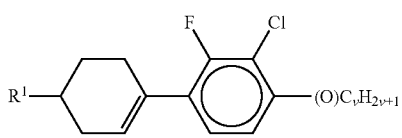 LY2

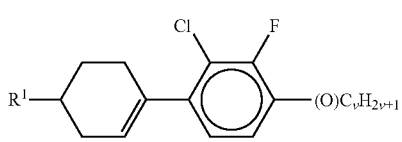 LY3

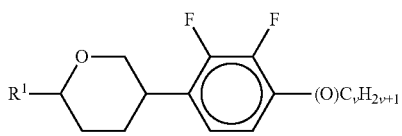 LY4

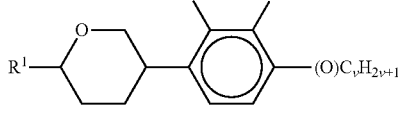 LY5

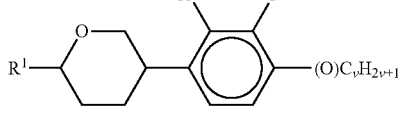 LY6

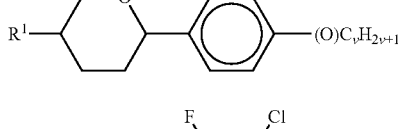 LY7

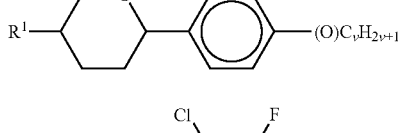 LY8

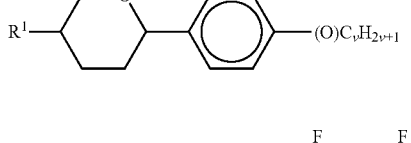 LY9

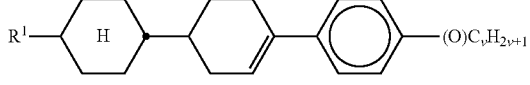 LY10

LY11
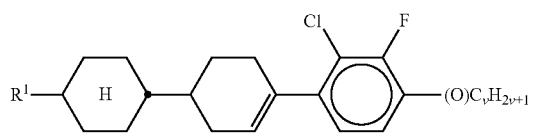

LY12
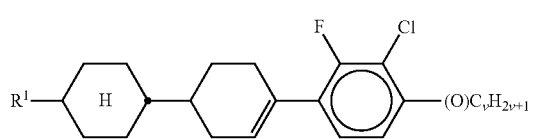

LY13
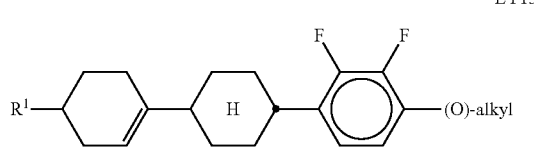

LY14

LY15
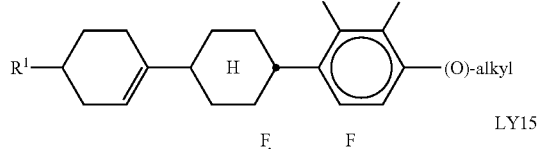

LY16
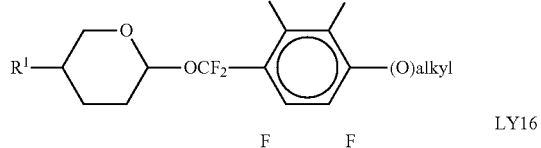

LY17
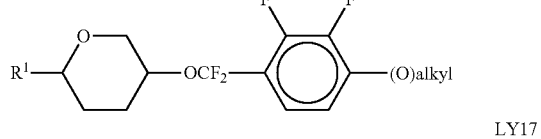

LY18
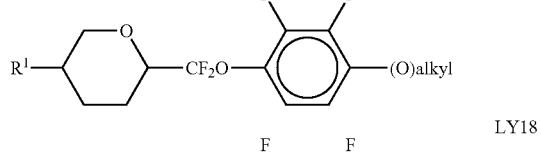

LY19
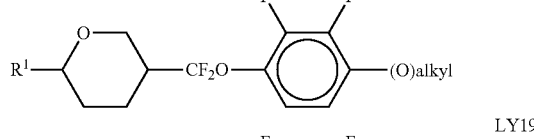

LY20
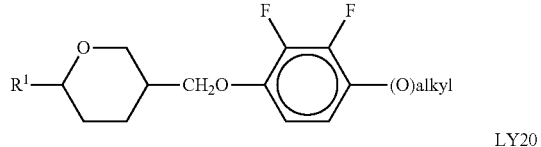

LY21
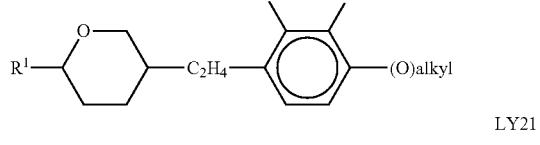

LY22
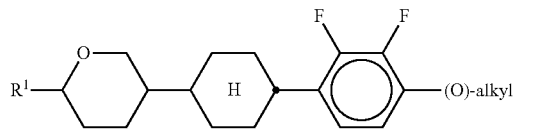

LY23
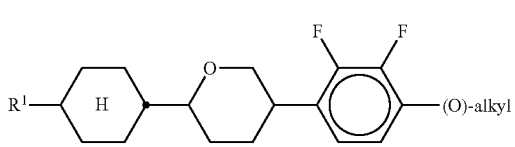

LY24 in which $R^1$ has the meaning indicated above, alkyl denotes a straight-chain alkyl radical having 1-6 C atoms, (O) denotes an oxygen atom or a single bond, and v denotes an integer from 1 to 6. $R^1$ preferably denotes straight-chain alkyl having 1 to 6 C atoms or straight-chain alkenyl having 2 to 6 C atoms, in particular $CH_3$, $C_2H_5$, n-$C_3H_7$, n-$C_4H_9$, n-$C_5H_{11}$, $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

e) LC medium which additionally comprises one or more compounds selected from the group consisting of the following formulae:

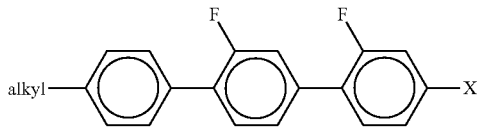
G1

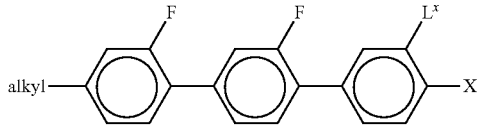
G2

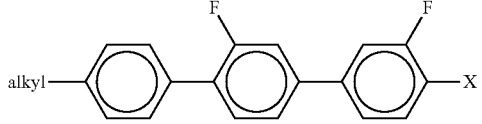
G3

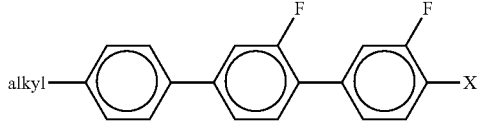
G4 in which alkyl denotes $C_{1-6}$-alkyl, $L^x$ denotes H or F, and X denotes F, Cl, $OCF_3$, $OCHF_2$ or $OCH=CF_2$. Particular preference is given to compounds of the formula G1 in which X denotes F.

f) LC medium which additionally comprises one or more compounds selected from the group consisting of the following formulae:

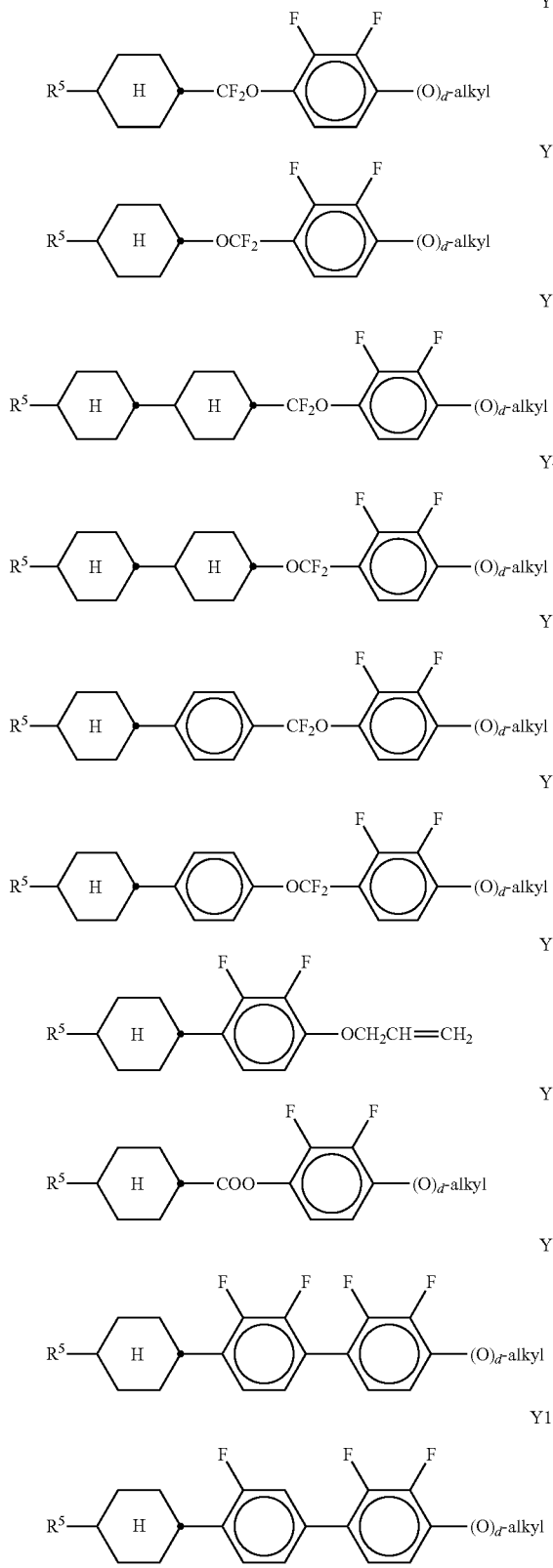
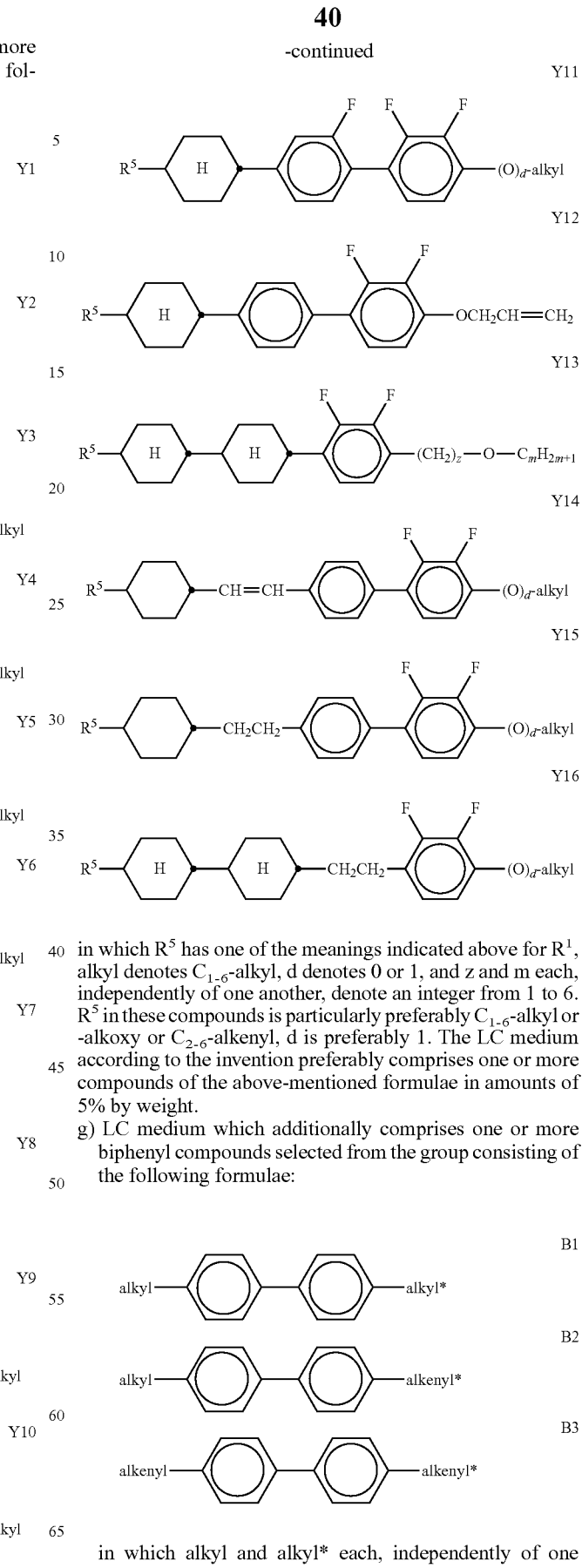

in which $R^5$ has one of the meanings indicated above for $R^1$, alkyl denotes $C_{1-6}$-alkyl, d denotes 0 or 1, and z and m each, independently of one another, denote an integer from 1 to 6. $R^5$ in these compounds is particularly preferably $C_{1-6}$-alkyl or -alkoxy or $C_{2-6}$-alkenyl, d is preferably 1. The LC medium according to the invention preferably comprises one or more compounds of the above-mentioned formulae in amounts of 5% by weight.

g) LC medium which additionally comprises one or more biphenyl compounds selected from the group consisting of the following formulae:

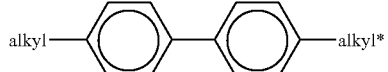

B1

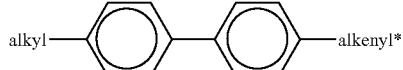

B2

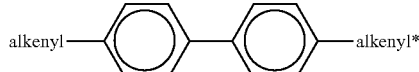

B3 in which alkyl and alkyl* each, independently of one another, denote a straight-chain alkyl radical having 1-6

C atoms, and alkenyl and alkenyl* each, independently of one another, denote a straight-chain alkenyl radical having 2-6 C atoms. Alkenyl and alkenyl* preferably denote CH$_2$=CH—, CH$_2$=CHCH$_2$CH$_2$—, CH$_3$—CH=CH—, CH$_3$—CH$_2$—CH=CH—, CH$_3$—(CH$_2$)$_2$—CH=CH—, CH$_3$—(CH$_2$)$_3$—CH=CH— or CH$_3$—CH=CH—(CH$_2$)$_2$—.

The proportion of the biphenyls of the formulae B1 to B3 in the LC mixture is preferably at least 3% by weight, in particular ≥5% by weight.

The compounds of the formula B2 are particularly preferred.

The compounds of the formulae B1 to B3 are preferably selected from the group consisting of the following sub-formulae:

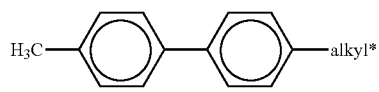

B1a

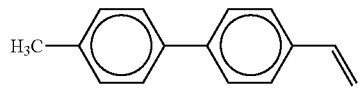

B2a

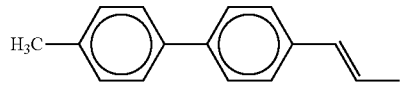

B2b

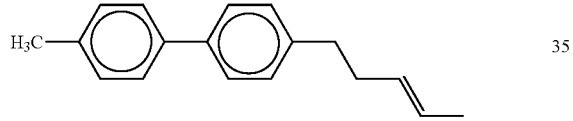

B2c in which alkyl* denotes an alkyl radical having 1-6 C atoms. The medium according to the invention particularly preferably comprises one or more compounds of the formulae B1a and/or B2c.

h) LC medium which additionally comprises one or more terphenyl compounds of the following formula:

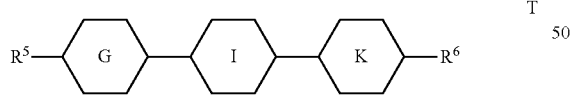

T in which R$^5$ and R$^6$ each, independently of one another, have one of the meanings indicated above for R$^1$, and

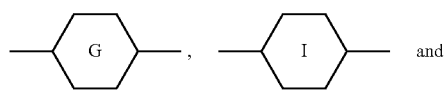

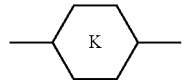

each, independently of one another, denote

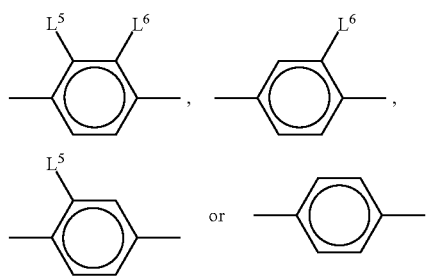

in which L$^5$ denotes F or Cl, preferably F, and L$^6$ denotes F, Cl, OCF$_3$, CF$_3$, CH$_3$, CH$_2$F or CHF$_2$, preferably F.

The compounds of the formula T are preferably selected from the group consisting of the following sub-formulae:

T1

T2

T3

T4

T5

T6

T7

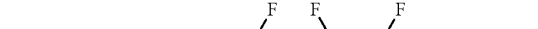

-continued

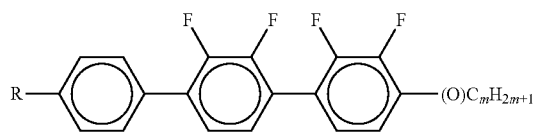
T8

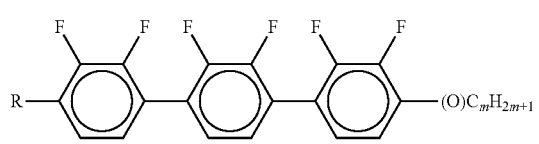
T9

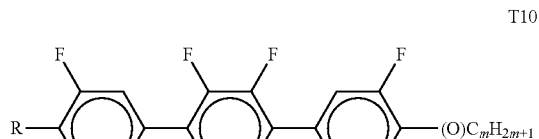
T10

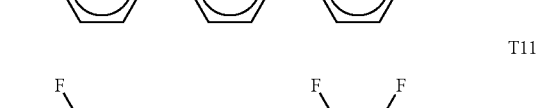
T11

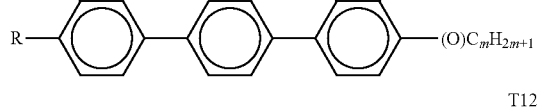
T12

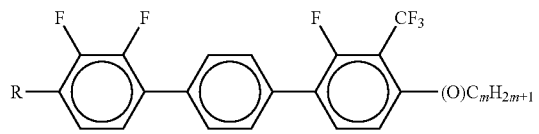
T13

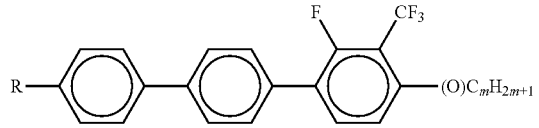
T14

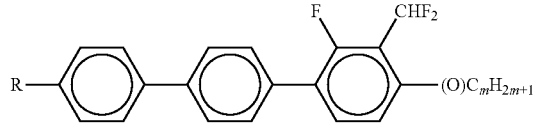
T15

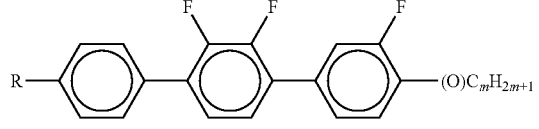
T16

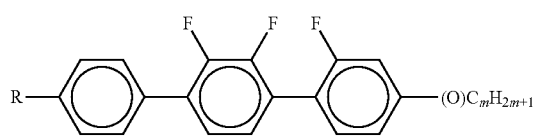
T17

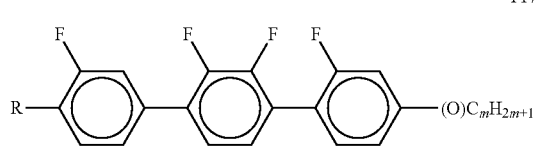

-continued

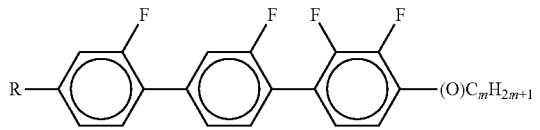
T18

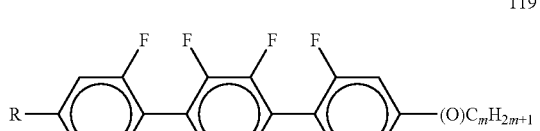
T19

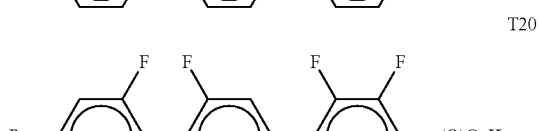
T20

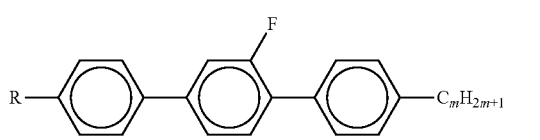
T21

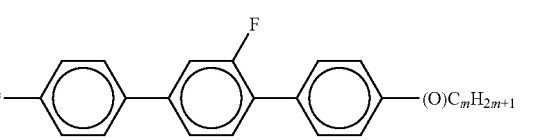
T22

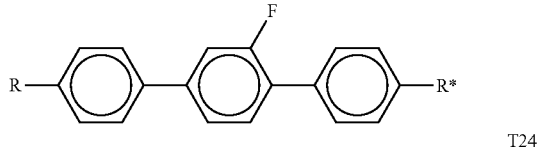
T23

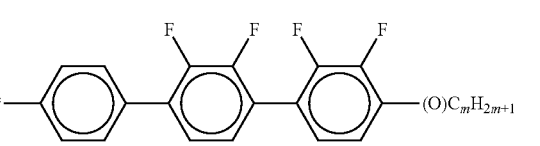
T24 in which R denotes a straight-chain alkyl or alkoxy radical having 1-7 C atoms, R* denotes a straight-chain alkenyl radical having 2-7 C atoms, (O) denotes an oxygen atom or a single bond, and m denotes an integer from 1 to 6. R* preferably denotes $CH_2$=CH—, $CH_2$=CHCH$_2$CH$_2$—, $CH_3$—CH=CH—, $CH_3$—CH$_2$—CH=CH—, $CH_3$—(CH$_2$)$_2$—CH=CH—, $CH_3$—(CH$_2$)$_3$—CH=CH— or $CH_3$—CH=CH—(CH$_2$)$_2$—.

R preferably denotes methyl, ethyl, propyl, butyl, pentyl, hexyl, methoxy, ethoxy, propoxy, butoxy or pentoxy.

The LC medium according to the invention preferably comprises the terphenyls of the formula T and the preferred sub-formulae thereof in an amount of 0.5-30% by weight, in particular 1-20% by weight.

Particular preference is given to compounds of the formulae T1, T2, T3 and T21. In these compounds, R preferably denotes alkyl, furthermore alkoxy, each having 1-5 C atoms.

The terphenyls are preferably employed in mixtures according to the invention if the Δn value of the mixture is to be ≥0.1. Preferred mixtures comprise 2-20% by weight of one or more terphenyl compounds of the formula T, preferably selected from the group of compounds T1 to T22.

i) LC medium which additionally comprises one or more compounds selected from the group consisting of the following formulae:

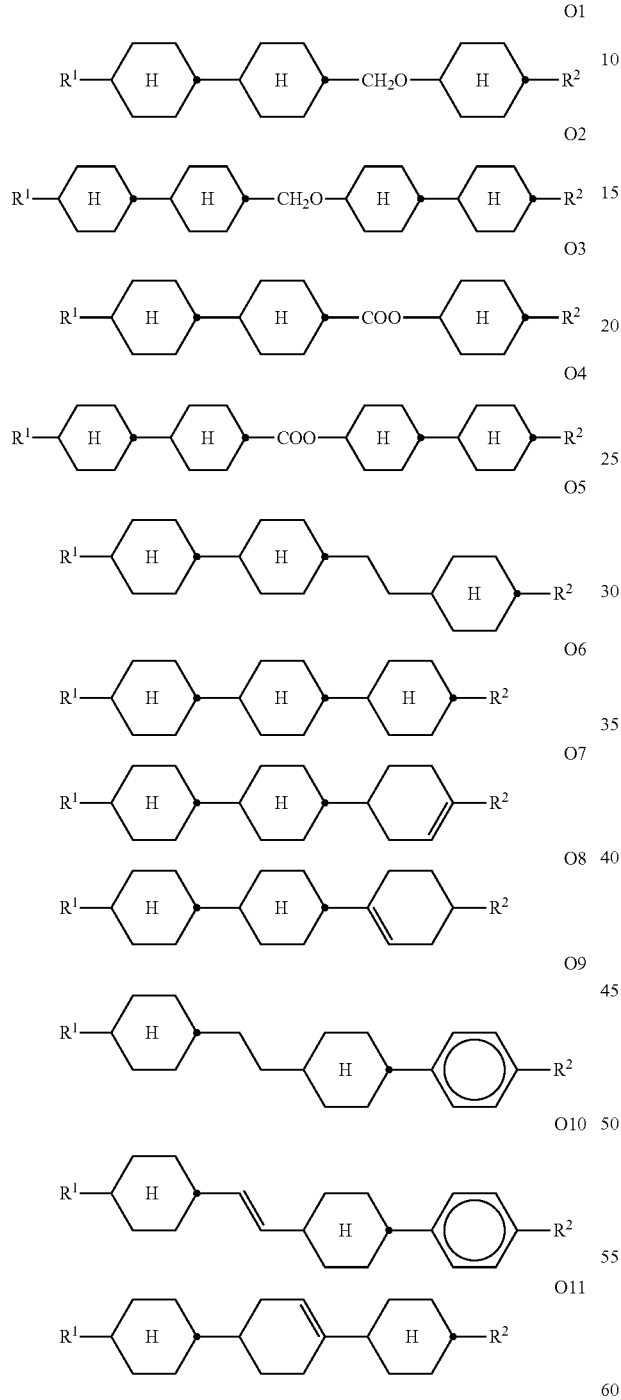

in which $R^1$ and $R^2$ have the meanings indicated above and preferably each, independently of one another, denote straight-chain alkyl having 1 to 6 C atoms or straight-chain alkenyl having 2 to 6 C atoms.

Preferred media comprise one or more compounds selected from the formulae O1, O3 and O4.

k) LC medium which additionally comprises one or more compounds of the following formula:

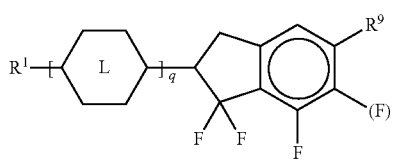

in which

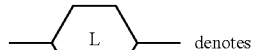 denotes

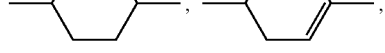

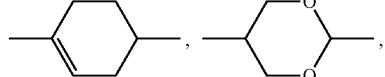

$R^9$ denotes H, $CH_3$, $C_2H_5$ or n-$C_3H_7$, (F) denotes an optional fluorine substituent, and q denotes 1, 2 or 3, and $R^7$ has one of the meanings indicated for $R^1$, preferably in amounts of >3% by weight, in particular ≥5% by weight and very particularly preferably 5-30% by weight.

Particularly preferred compounds of the formula FI are selected from the group consisting of the following sub-formulae:

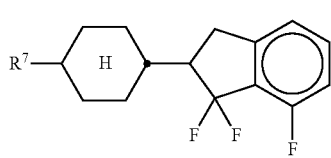

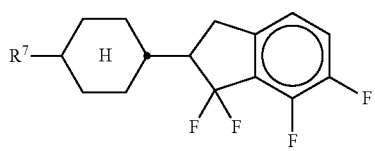

FI3 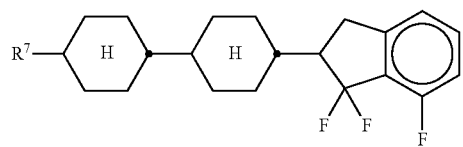

FI4 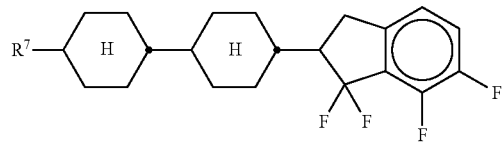

FI5 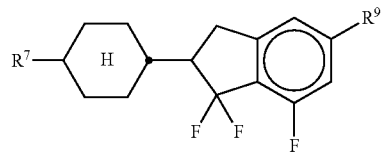

FI6 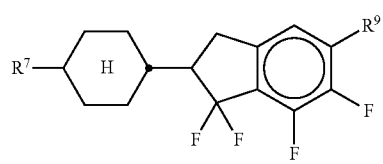

FI7 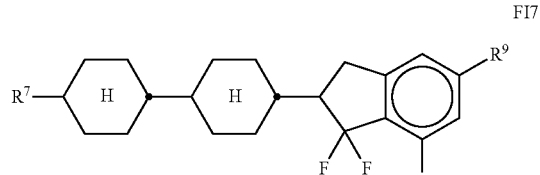

FI8 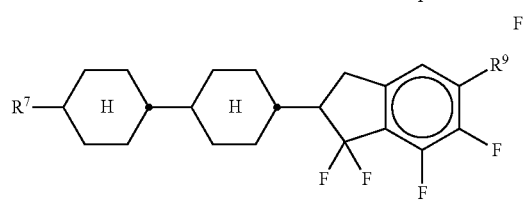

in which $R^7$ preferably denotes straight-chain alkyl, and $R^9$ denotes $CH_3$, $C_2H_5$ or $n-C_3H_7$. Particular preference is given to the compounds of the formulae FI1, FI2 and FI3.

m) LC medium which additionally comprises one or more compounds selected from the group consisting of the following formulae:

VK1 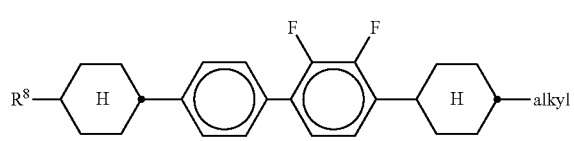

VK2 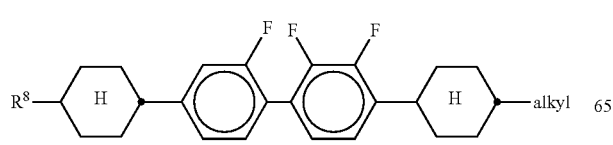

VK3 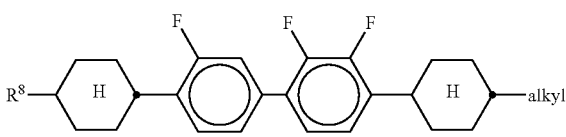

VK4 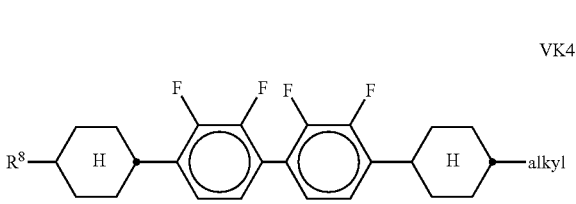

in which $R^8$ has the meaning indicated for $R^1$, and alkyl denotes a straight-chain alkyl radical having 1-6 C atoms.

n) LC medium which additionally comprises one or more compounds which contain a tetrahydronaphthyl or naphthyl unit, such as, for example, the compounds selected from the group consisting of the following formulae:

N1 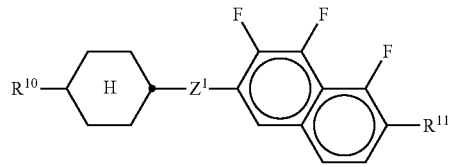

N2 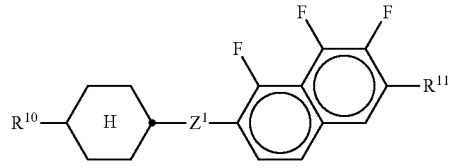

N3 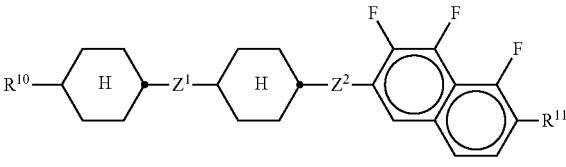

N4 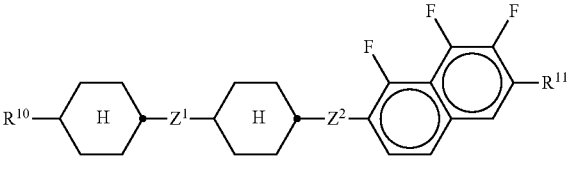

N5 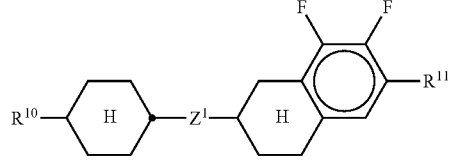

N6
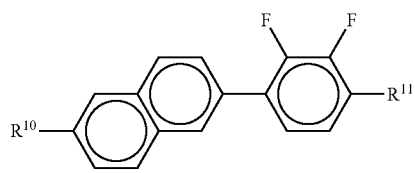

N7
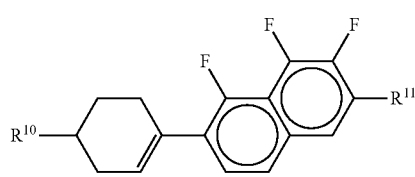

N8
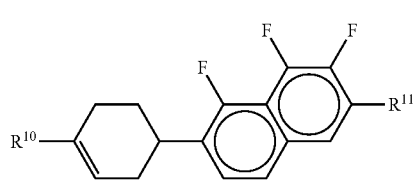

N9
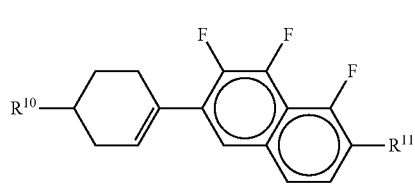

N10
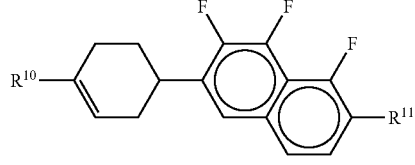

in which $R^{10}$ and $R^{11}$ each, independently of one another, have one of the meanings indicated for $R^1$, preferably denote straight-chain alkyl or alkoxy having 1 to 6 C atoms or straight-chain alkenyl having 2 to 6 C atoms, and $Z^1$ and $Z^2$ each, independently of one another, denote —C₂H₄—, —CH═CH—, —(CH₂)₄—, —(CH₂)₃O—, —O(CH₂)₃—, —CH═CH—CH₂CH₂—, —CH₂CH₂CH═CH—, —CH₂O—, —OCH₂—, —CO—O—, —O—CO—, —C₂F₄—, —CF═CF—, —CF═CH—, —CH═CF—, —CH₂— or a single bond.

j) LC medium which additionally comprises one or more difluorodibenzochromans and/or chromans of the following formulae:

BC
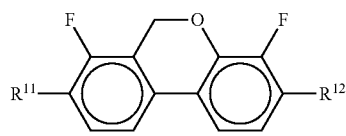

CR
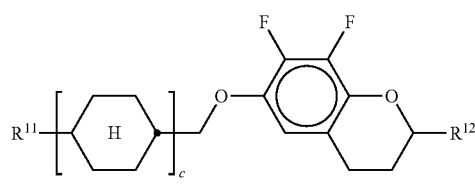

RC
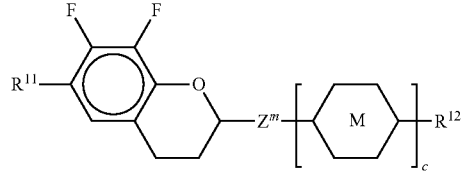

in which $R^{11}$ and $R^{12}$ each, independently of one another, have the meanings indicated above, ring M denotes trans-1,4-cyclohexylene or 1,4-phenylene, $Z^m$ denotes —C₂H₄—, —CH₂O—, —OCH₂—, —CO—O— or —O—CO—, and c denotes 0 or 1, preferably in amounts of 3 to 20% by weight, in particular in amounts of 3 to 15% by weight.

Particularly preferred compounds of the formulae BC and CR are selected from the group consisting of the following sub-formulae:

BC1
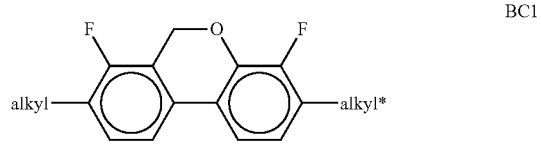

BC2
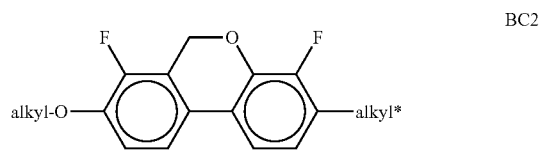

BC3
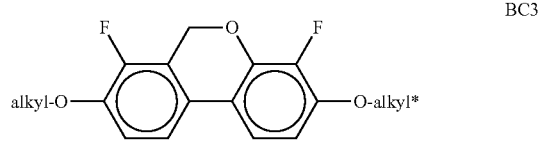

BC4
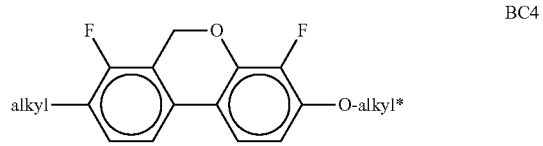

BC5
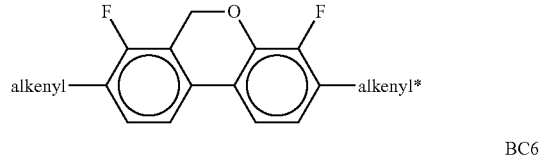

BC6
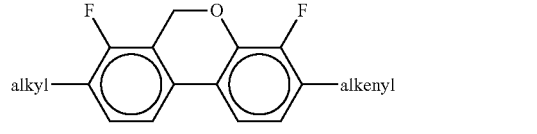

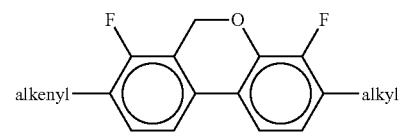
BC7

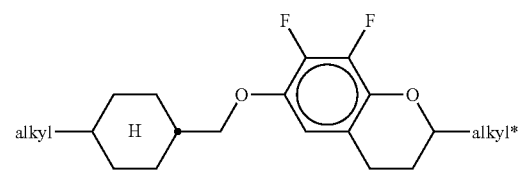
CR1

CR2

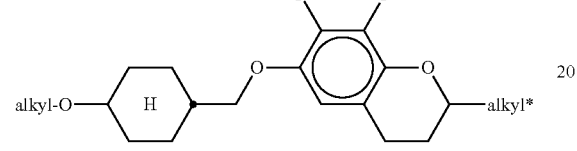
CR3

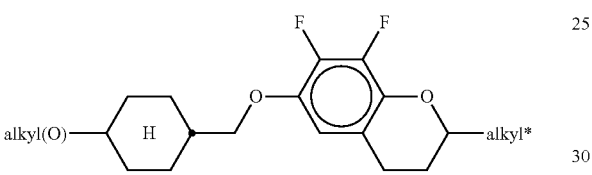
CR4

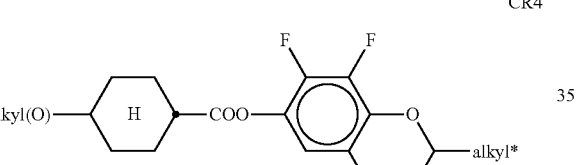
CR5

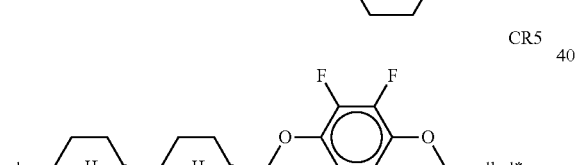
CR6

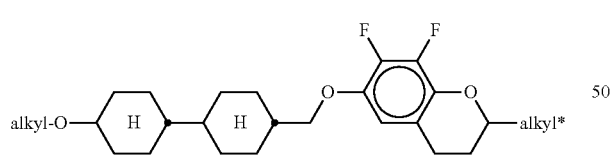
CR7

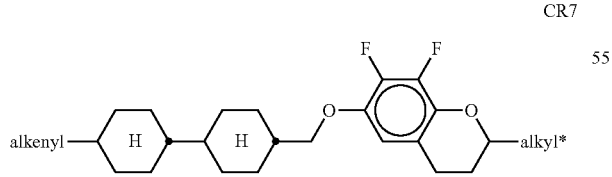
CR8

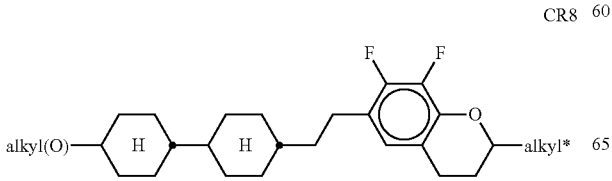

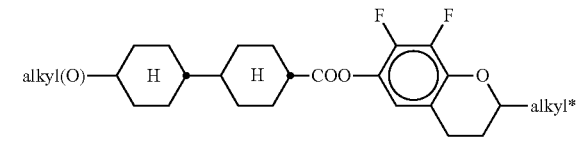
CR9

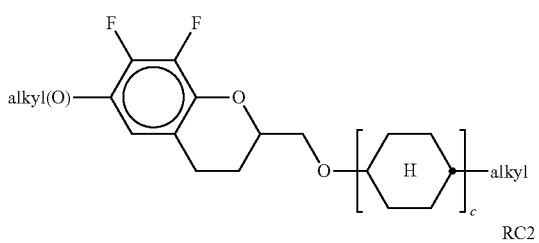
RC1

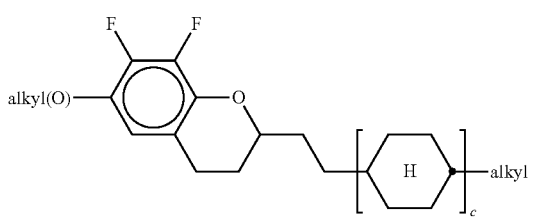
RC2

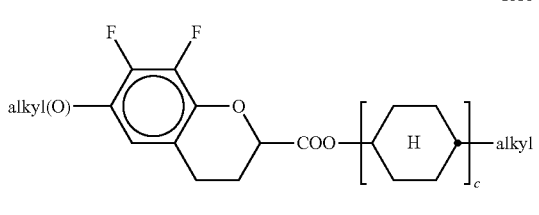
RC3 in which alkyl and alkyl* each, independently of one another, denote a straight-chain alkyl radical having 1-6 C atoms, (O) denotes an oxygen atom or a single bond, and alkenyl and alkenyl* each, independently of one another, denote a straight-chain alkenyl radical having 2-6 C atoms. Alkenyl and alkenyl* preferably denote $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

Very particular preference is given to mixtures comprising one, two or three compounds of the formula BC-2.

p) LC medium which additionally comprises one or more fluorinated phenanthrenes and/or dibenzofurans of the following formulae:

PH

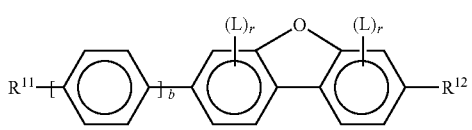
BF in which $R^{11}$ and $R^{12}$ each, independently of one another, have the meanings indicated above, b denotes 0 or 1, L denotes F, and r denotes 1, 2 or 3.

Particularly preferred compounds of the formulae PH and BF are selected from the group consisting of the following sub-formulae:

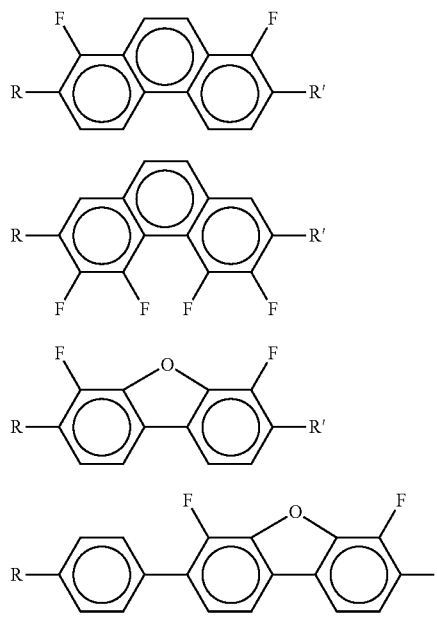

in which R and R' each, independently of one another, denote a straight-chain alkyl or alkoxy radical having 1-7 C atoms.

q) LC medium which, apart from the polymerisable compounds according to the invention, in particular of the formula I or sub-formulae thereof and the comonomers, comprises no compounds which contain a terminal vinyloxy group (—O—CH=CH$_2$).

r) LC medium which comprises 1 to 5, preferably 1, 2 or 3, polymerisable compounds, preferably selected from polymerisable compounds according to the invention, in particular of the formula I or sub-formulae thereof.

s) LC medium in which the proportion of polymerisable compounds, in particular of the formula I or sub-formulae thereof, in the mixture as a whole is 0.05 to 5%, preferably 0.1 to 1%.

t) LC medium which comprises 1 to 8, preferably 1 to 5, compounds of the formulae CY1, CY2, PY1 and/or PY2. The proportion of these compounds in the mixture as a whole is preferably 5 to 60%, particularly preferably 10 to 35%. The content of these individual compounds is preferably in each case 2 to 20%.

u) LC medium which comprises 1 to 8, preferably 1 to 5, compounds of the formulae CY9, CY10, PY9 and/or PY10. The proportion of these compounds in the mixture as a whole is preferably 5 to 60%, particularly preferably 10 to 35%. The content of these individual compounds is preferably in each case 2 to 20%.

v) LC medium which comprises 1 to 10, preferably 1 to 8, compounds of the formula ZK, in particular compounds of the formulae ZK1, ZK2 and/or ZK6. The proportion of these compounds in the mixture as a whole is preferably 3 to 25%, particularly preferably 5 to 45%. The content of these individual compounds is preferably in each case 2 to 20%.

w) LC medium in which the proportion of compounds of the formulae CY, PY and ZK in the mixture as a whole is greater than 70%, preferably greater than 80%.

x) PSA-VA display in which the pretilt angle is preferably ≤85°, particularly preferably ≤80°.

In a second preferred embodiment of the present invention, the LC medium comprises an LC host mixture based on compounds having positive dielectric anisotropy. LC media of this type are particularly suitable for use in PSA-OCB, PSA-TN, PSA-positive-VA, PSA-IPS and PSA-FFS displays. Particularly preferred embodiments of such displays are given below:

LC medium which comprises one or more compounds selected from the group consisting of the compounds of the following formulae:

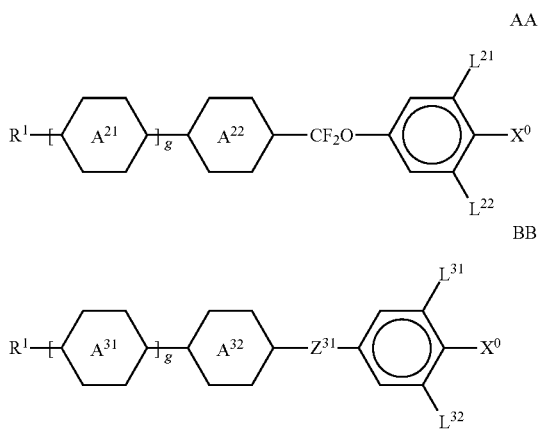

LC medium which, in addition to the compounds of the formulae AA and/or BB, comprises one or more compounds of the following formula:

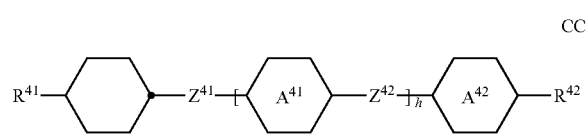

In the formulae AA, BB and CC, the individual radicals have the following meanings:

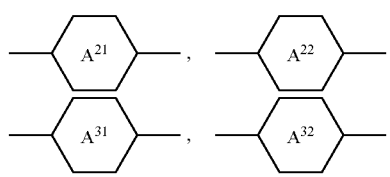

each, independently of one another, and identically or differently on each occurrence, denote

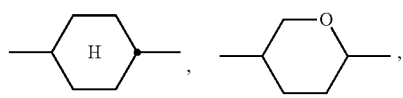

-continued

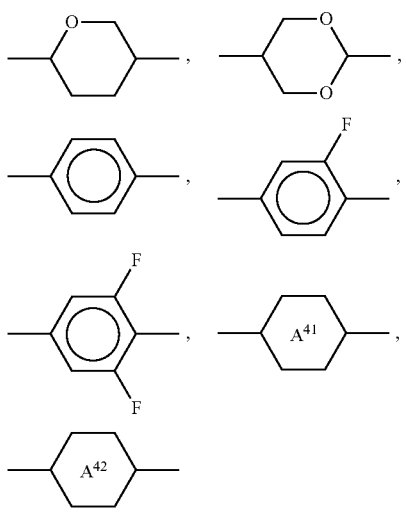

each, independently of one another, and identically or differently on each occurrence, denote

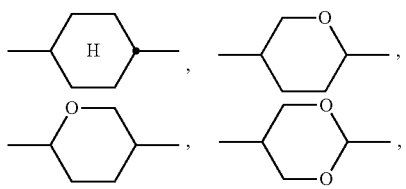

-continued

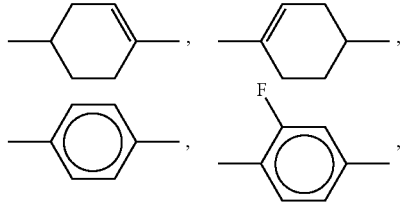

$R^{21}$, $R^{31}$, $R^{41}$, $R^{42}$ each, independently of one another, denote alkyl, alkoxy, oxaalkyl or fluoroalkyl having 1 to 9 C atoms or alkenyl having 2 to 9 C atoms, $X^0$ denotes F, Cl, halogenated alkyl or alkoxy having 1 to 6 C atoms or halogenated alkenyl or alkenyloxy having 2 to 6 C atoms, $Z^{31}$ denotes —CH$_2$CH$_2$—, —CF$_2$CF$_2$—, —COO—, trans-CH=CH—, trans-CF=CF—, —CH$_2$O— or a single bond, preferably —CH$_2$CH$_2$—, —COO—, trans-CH=CH— or a single bond, particularly preferably —COO—, trans-CH=CH— or a single bond, $Z^{41}$, $Z^{42}$ denotes —CH$_2$CH$_2$—, —COO—, trans-CH=CH—, trans-CF=CF—, —CH$_2$O—, —CF$_2$O—, —C≡C— or a single bond, preferably a single bond, $L^{21}$, $L^{22}$, $L^{31}$, $L^{32}$ denote H or F, g denotes 1, 2 or 3, h denotes 0, 1, 2 or 3.

$X^0$ preferably denotes F, Cl, CF$_3$, CHF$_2$, OCF$_3$, OCHF$_2$, OCFHCF$_3$, OCFHCHF$_2$, OCFHCHF$_2$, OCF$_2$CH$_3$, OCF$_2$CHF$_2$, OCF$_2$CHF$_2$, OCF$_2$CF$_2$CHF$_2$, OCF$_2$CF$_2$CHF$_2$, OCFHCF$_2$CF$_3$, OCFHCF$_2$CHF$_2$, OCF$_2$CF$_2$CF$_3$, OCF$_2$CF$_2$CClF$_2$, OCClFCF$_2$CF$_3$ or CH=CF$_2$, particularly preferably F or OCF$_3$.

The compounds of the formula AA are preferably selected from the group consisting of the following formulae:

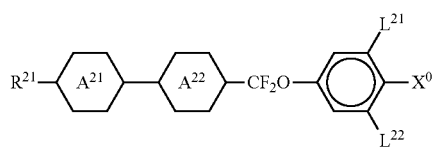

AA1

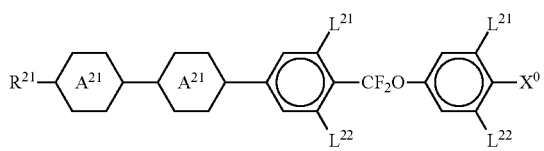

AA2

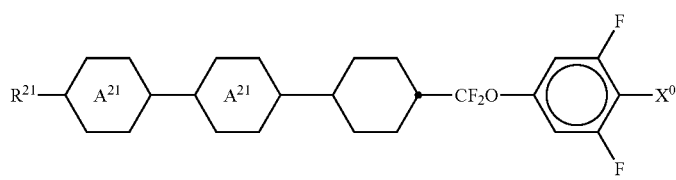

AA3

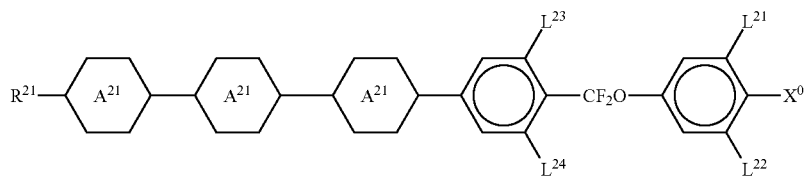

AA4 in which $A^{21}$, $R^{21}$, $X^0$, $L^{21}$ and $L^{22}$ have the meanings indicated in formula AA, $L^{23}$ and $L^{24}$ each, independently of one another, denote H or F, and $X^0$ preferably denotes F. Particular preference is given to compounds of the formulae AA1 and AA2.

Particularly preferred compounds of the formula AA1 are selected from the group consisting of the following sub-formulae:

AA1a
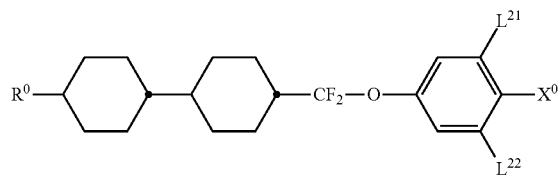

AA1b
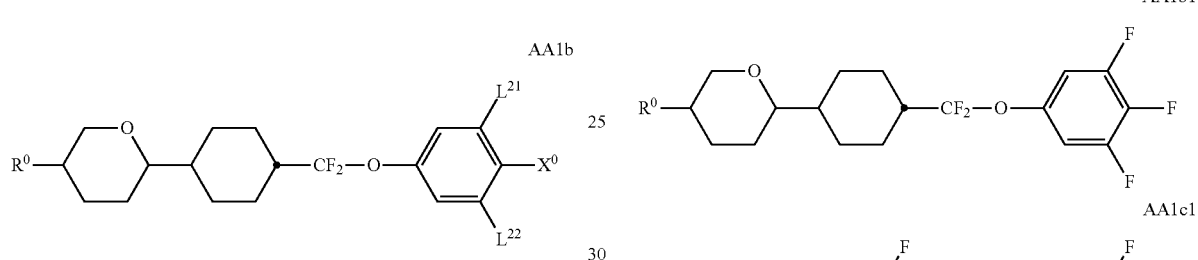

AA1c
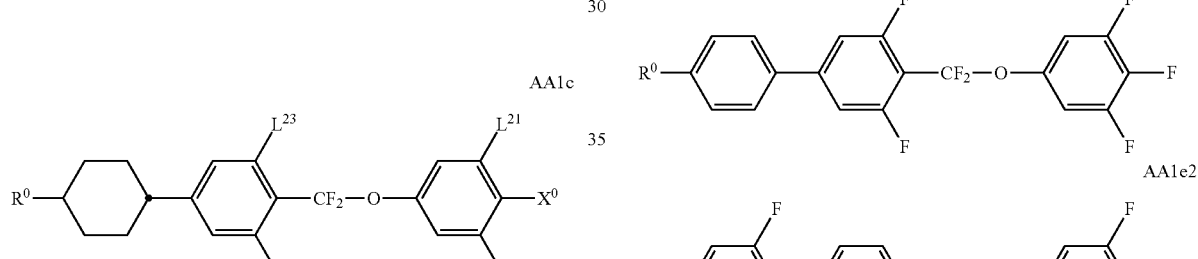

AA1d
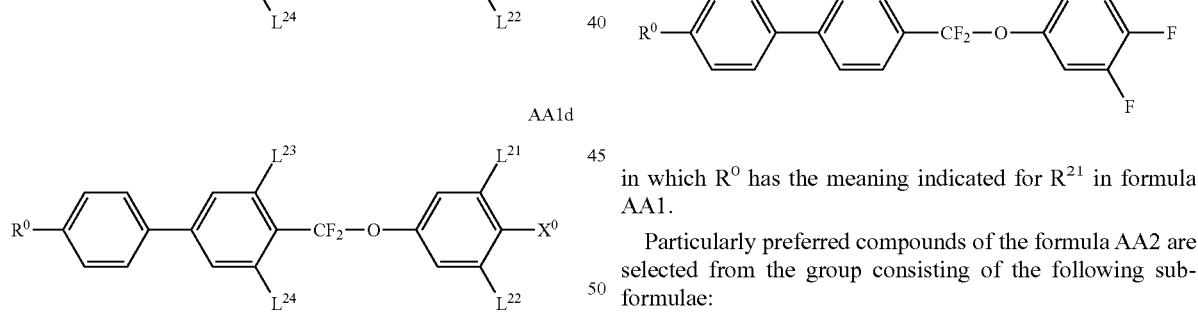

AA1e
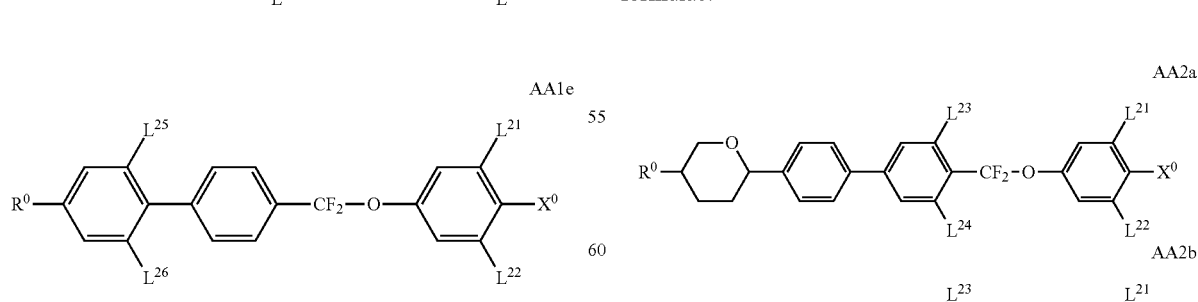

in which $R^0$ has one of the meanings indicated for $R^{21}$ in formula AA1, $X^0$, $L^{21}$ and $L^{22}$ have the meanings indicated in formula AA1, $L^{23}$, $L^{24}$, $L^{25}$ and $L^{26}$ each, independently of one another, denote H or F, and $X^0$ preferably denotes F.

Very particularly preferred compounds of the formula AA1 are selected from the group consisting of the following sub-formulae:

AA1a1
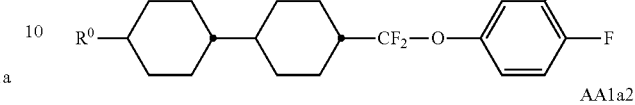

AA1a2

AA1b1
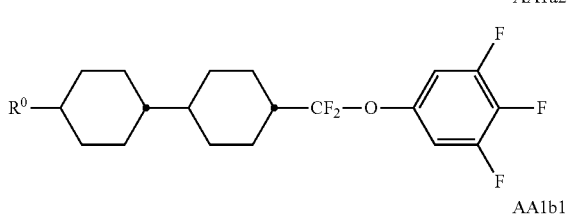

AA1c1
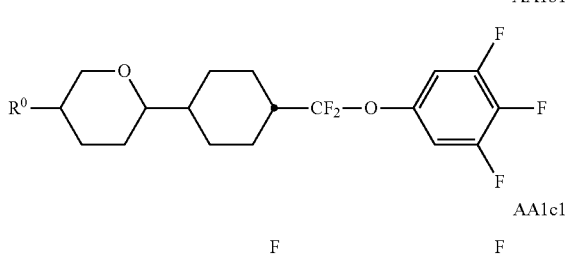

AA1e2
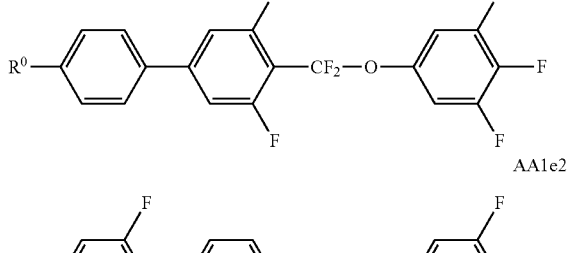

in which $R^0$ has the meaning indicated for $R^{21}$ in formula AA1.

Particularly preferred compounds of the formula AA2 are selected from the group consisting of the following sub-formulae:

AA2a
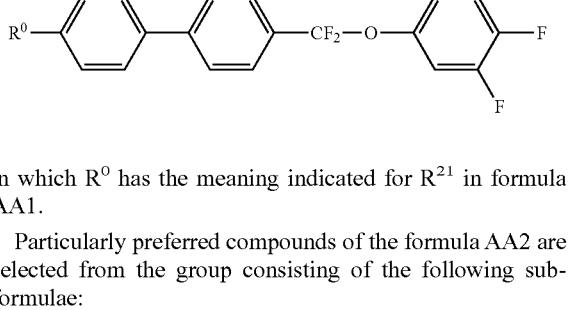

AA2b
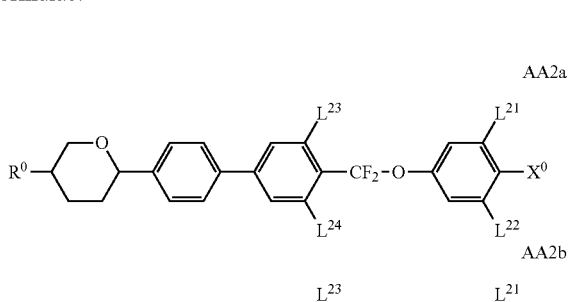

-continued
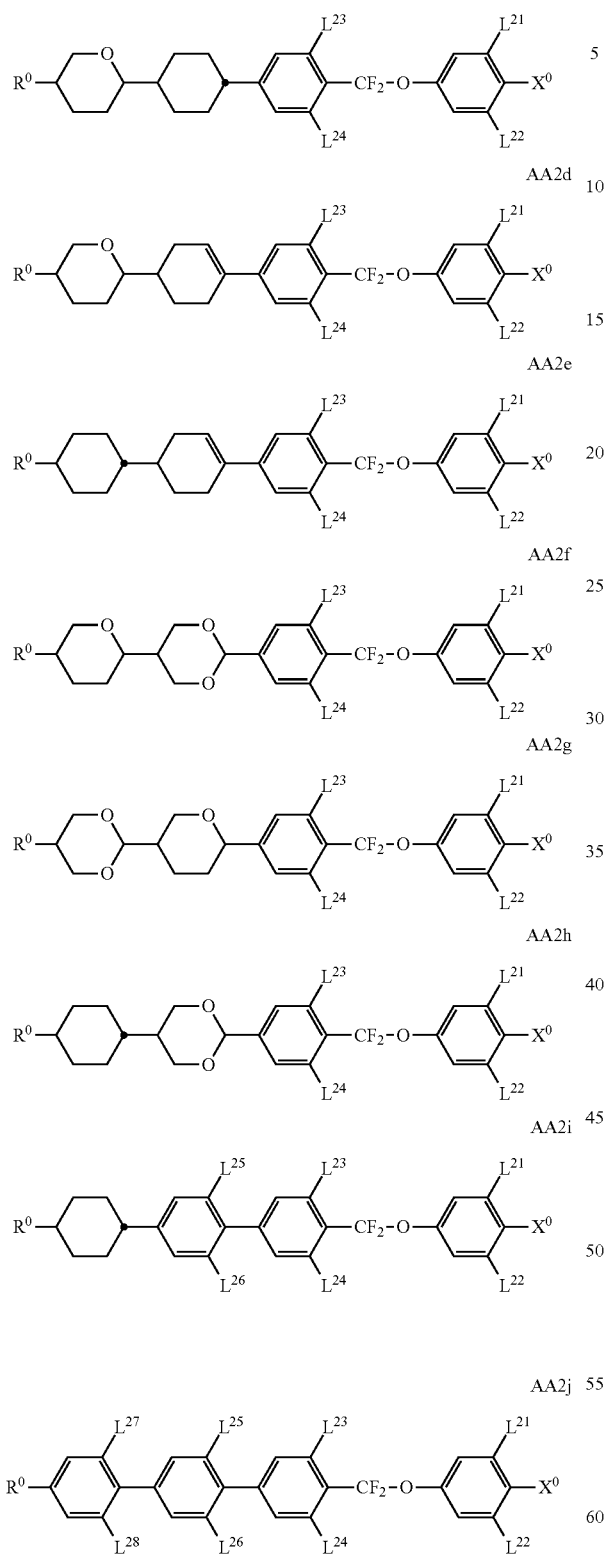
in which R⁰ has the meaning indicated for $R^{21}$ in formula AA1, $X^0$, $L^{21}$ and $L^{22}$ have the meanings indicated in formula AA, $L^{23}$, $L^{24}$, $L^{25}$ and $L^{26}$ each, independently of one another, denote H or F, and $X^0$ preferably denotes F.
Very particularly preferred compounds of the formula AA2 are selected from the group consisting of the following sub-formulae:
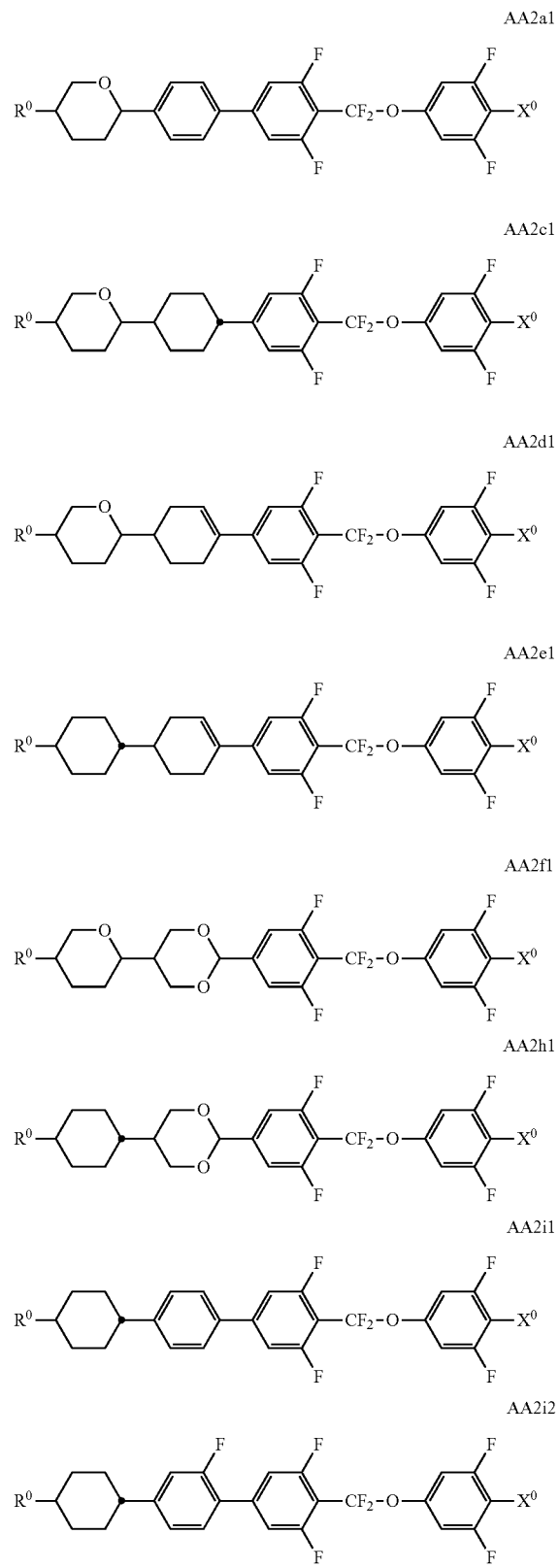

-continued

AA2j1
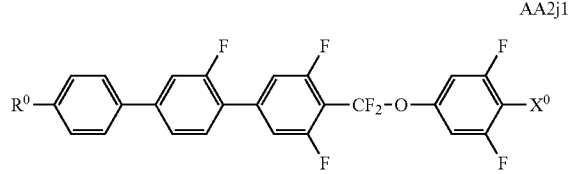

AA2j2
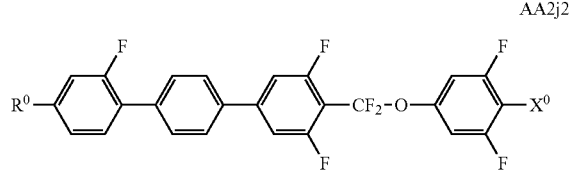

in which $R^0$ has the meaning indicated for $R^{21}$ in formula AA1.

Particularly preferred compounds of the formula AA3 are selected from the group consisting of the following sub-formulae:

AA3a
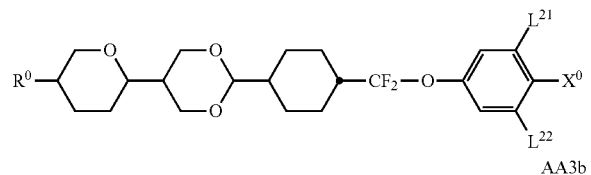

AA3b
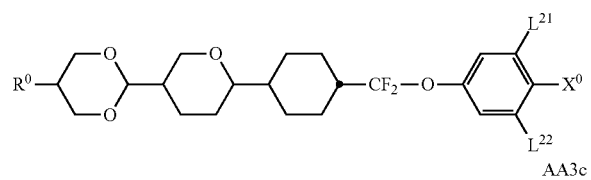

AA3c
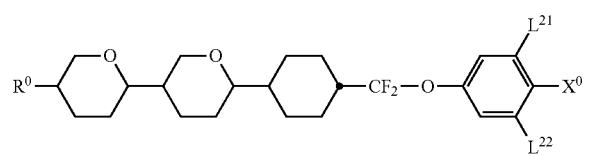

in which $R^0$ has the meaning indicated for $R^{21}$ in formula AA1, $X^0$, $L^{21}$ and $L^{22}$ have the meanings indicated in formula AA3, and $X^0$ preferably denotes F.

Particularly preferred compounds of the formula AA4 are selected from the group consisting of the following sub-formula:

AA4a
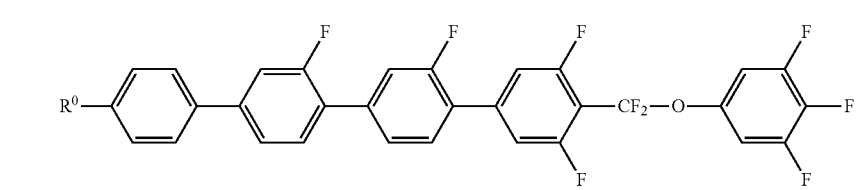

in which $R^0$ has the meaning indicated for $R^{21}$ in formula AA1.

The compounds of the formula BB are preferably selected from the group consisting of the following sub-formulae:

BB1
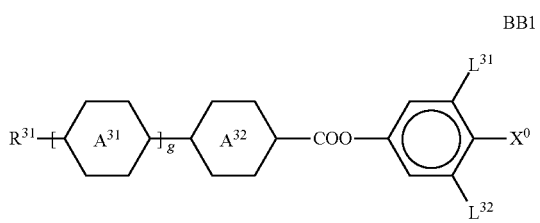

BB2
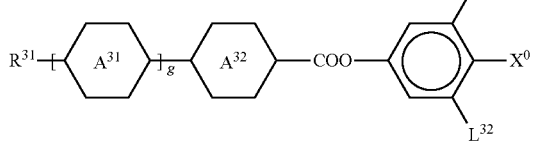

BB3
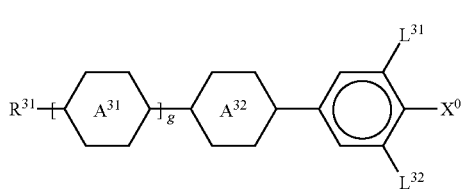

in which $A^{31}$, $A^{32}$, $R^{31}$, $X^0$, $L^{31}$ and $L^{32}$ have the meanings indicated in formula BB, and $X^0$ preferably denotes F. Particular preference is given to compounds of the formulae BB1 and BB2.

Particularly preferred compounds of the formula BB1 are selected from the group consisting of the following sub-formulae:

BB1a
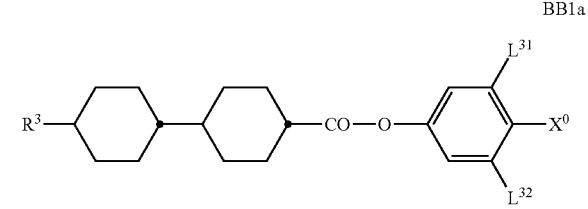

BB1b

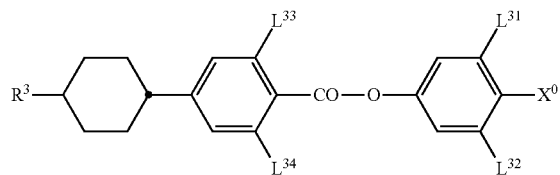

in which R³ has the meaning indicated for R³¹ in formula BB1, X⁰, L³¹ and L³² have the meanings indicated in formula BB1, and X⁰ preferably denotes F.

Very particularly preferred compounds of the formula BB1a are selected from the group consisting of the following sub-formulae:

BB1a1

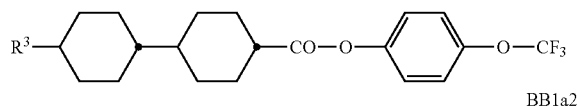

BB1a2

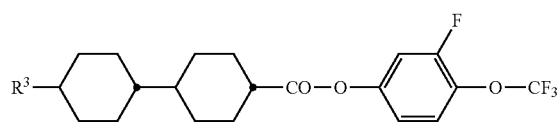

BB1a3

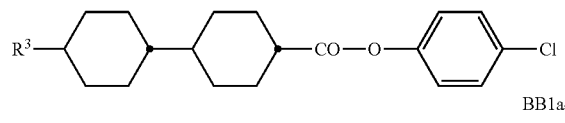

BB1a4

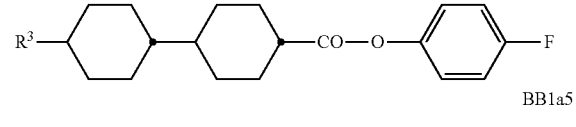

BB1a5

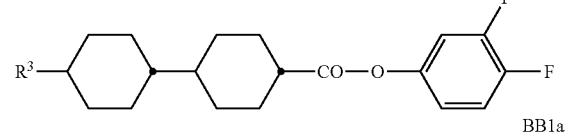

BB1a6

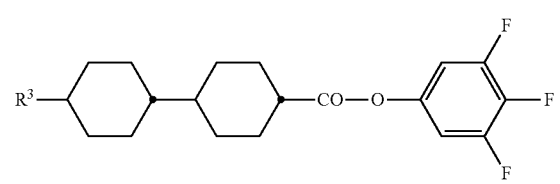

in which R³ has the meaning indicated for R³¹ in formula BB1.

Very particularly preferred compounds of the formula BB1b are selected from the group consisting of the following sub-formulae:

BB1b1

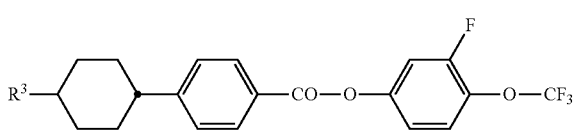

BB1b2

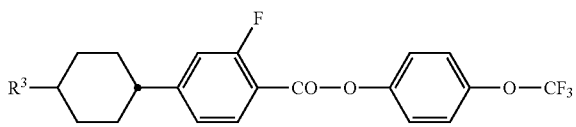

BB1b3

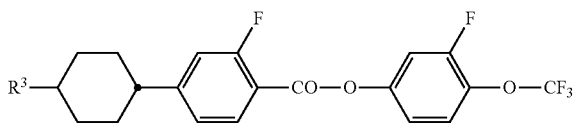

BB1b4

(not present — see below)

in which R³ has the meaning indicated for R³¹ in formula BB1.

Particularly preferred compounds of the formula BB2 are selected from the group consisting of the following sub-formulae:

BB2a

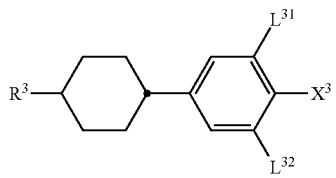

BB2b

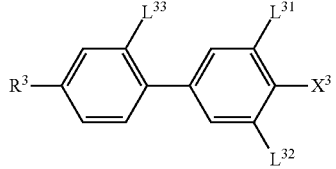

BB2c

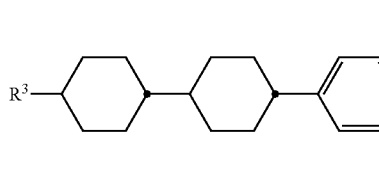

BB2d

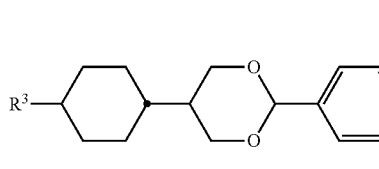

BB2e

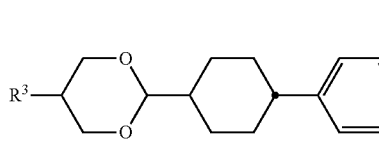

-continued

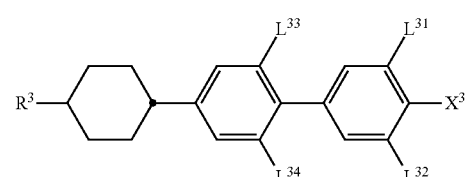
BB2f

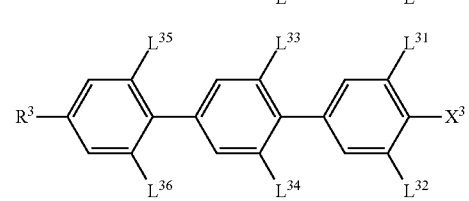
BB2g

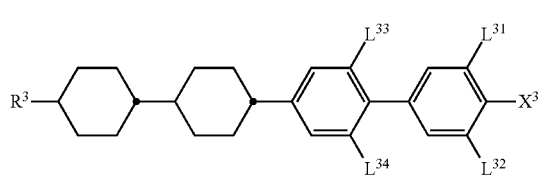
BB2h

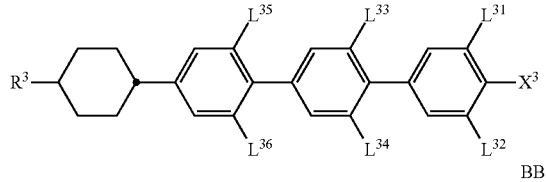
BB2i

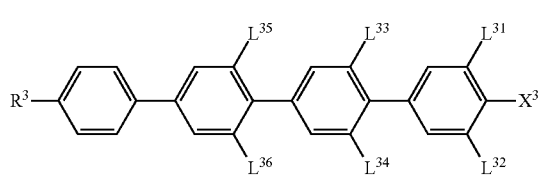
BB2k in which $R^0$ has one of the meanings indicated for $R^{21}$ in formula BB2, $X^0$, $L^{31}$ and $L^{32}$ have the meanings indicated in formula BB2, $L^{33}$, $L^{34}$, $L^{35}$ and $L^{36}$ each, independently of one another, denote H or F, and $X^0$ preferably denotes F.

Very particularly preferred compounds of the formula BB2a are selected from the group consisting of the following sub-formulae:

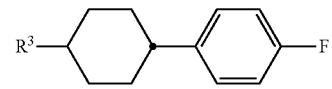
BB2a1

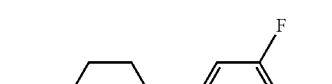
BB2a2

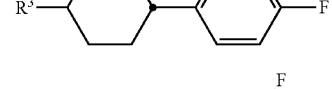
BB2a3

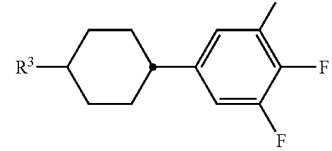

-continued

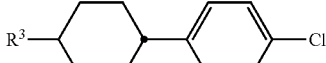
BB2a4

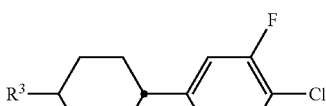
BB2a5 in which $R^3$ has the meaning indicated for $R^{31}$ in formula BB2.

Very particularly preferred compounds of the formula BB2b are selected from the group consisting of the following sub-formulae:

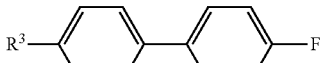
BB2b1

BB2b2

BB2b3

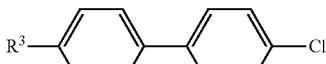
BB2b4 in which $R^3$ has the meaning indicated for $R^{31}$ in formula BB2.

Very particularly preferred compounds of the formula BB2c are selected from the group consisting of the following sub-formulae:

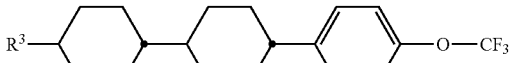
BB2c1

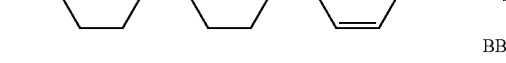
BB2c1

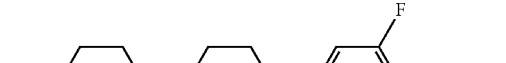
BB2c3

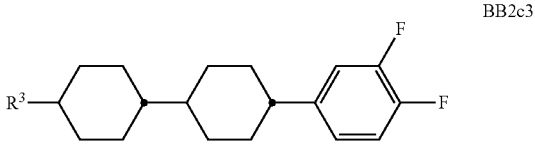

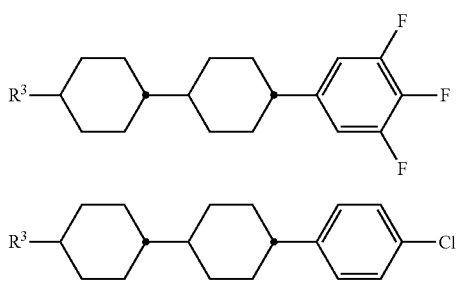

BB2c4

BB2c4 in which R³ has the meaning indicated for R³¹ in formula BB2.

Very particularly preferred compounds of the formulae BB2d and BB2e are selected from the group consisting of the following sub-formulae:

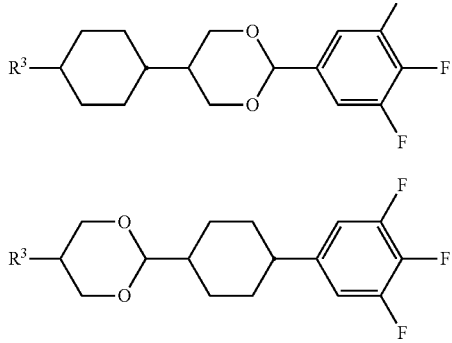

BB2d1

BB2e1 in which R³ has the meaning indicated for R³¹ in formula BB2.

Very particularly preferred compounds of the formula BB2f are selected from the group consisting of the following sub-formulae:

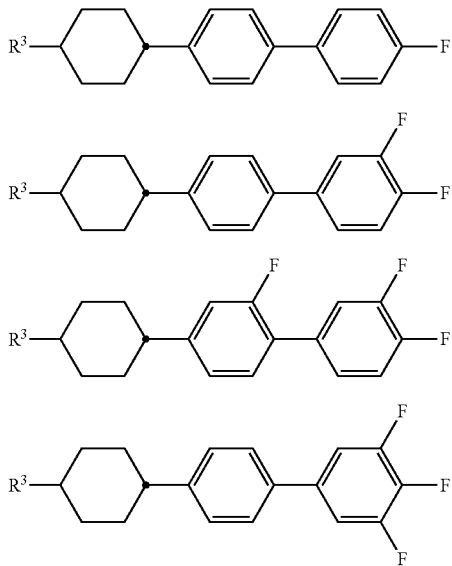

BB2F1

BB2F2

BB2F3

BB2F4

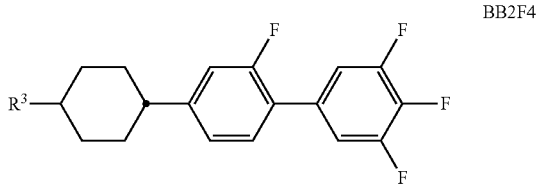

BB2F4 in which R³ has the meaning indicated for R³¹ in formula BB2.

Very particularly preferred compounds of the formula BB2g are selected from the group consisting of the following sub-formulae:

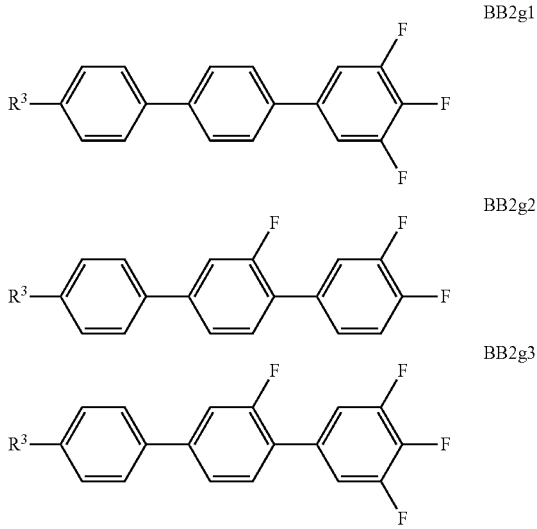

BB2g1

BB2g2

BB2g3

BB2g4

BB2g5

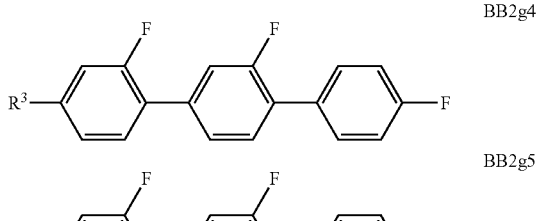

in which R³ has the meaning indicated for R³¹ in formula BB2.

Very particularly preferred compounds of the formula BB2h are selected from the group consisting of the following sub-formulae:

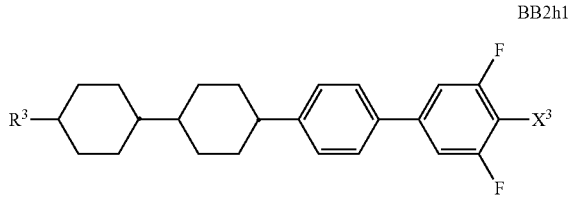

BB2h1

-continued

BB2h2

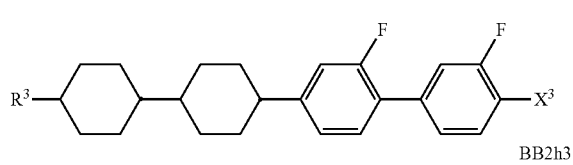

BB2h3

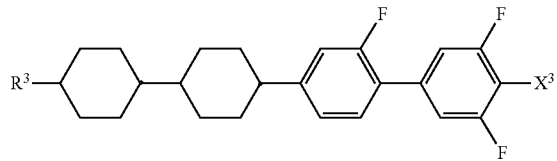

in which R³ has the meaning indicated for R³¹ in formula BB2.

Very particularly preferred compounds of the formula BB2i are selected from the group consisting of the following sub-formulae:

BB2i1

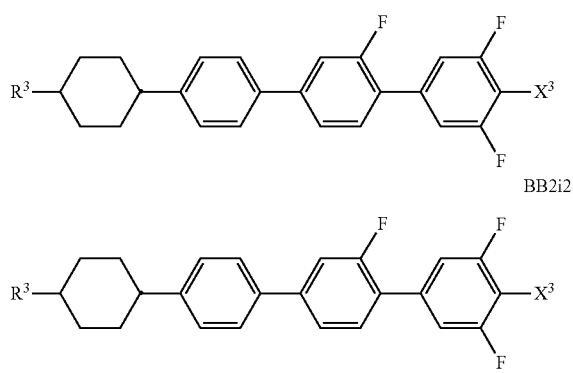

BB2i2 in which R³ has the meaning indicated for R³¹ in formula BB2.

Very particularly preferred compounds of the formula BB2k are selected from the group consisting of the following sub-formulae:

BB2k1

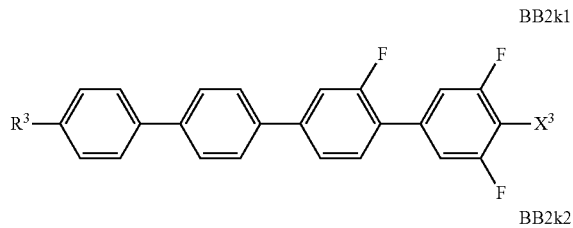

BB2k2

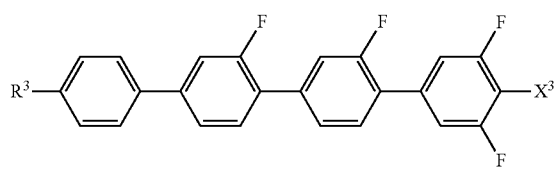

in which R³ has the meaning indicated for R³¹ in formula BB2.

Alternatively or additionally to the compounds of formulae BB1 and/or BB2, the LC medium may also comprise one or more compounds of the formula BB3 as defined above.

Particularly preferred compounds of the formula BB3 are selected from the group consisting of the following sub-formulae:

BB3a

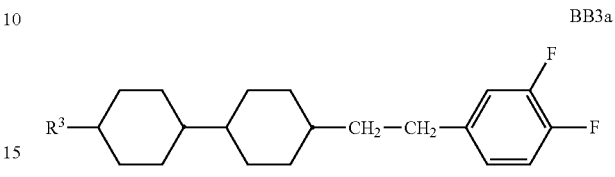

BB3b

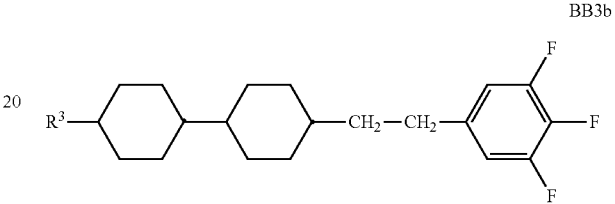

in which R³ has the meaning indicated for R³¹ in formula BB3.

In addition to the compounds of the formulae AA and/or BB, the LC medium in accordance with this second preferred embodiment preferably comprises one or more dielectrically neutral compounds having a dielectric anisotropy of −1.5 to +3 which are selected from the group consisting of compounds of the formula CC as defined above.

Particularly preferred compounds of the formula CC are selected from the group consisting of the following sub-formulae:

CC1

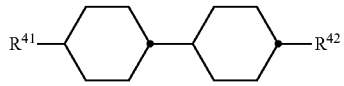

CC2

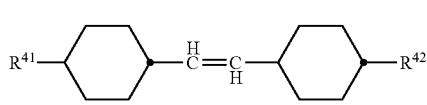

CC3

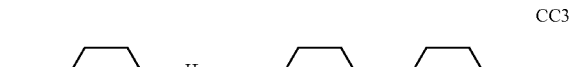

CC4

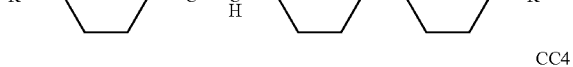

CC5

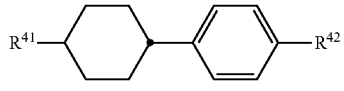

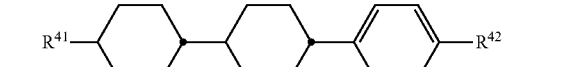

CC6

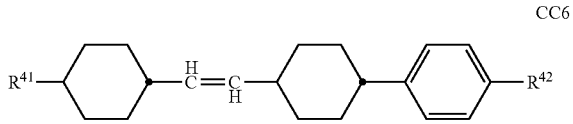

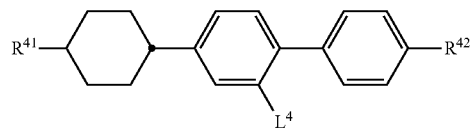
CC7

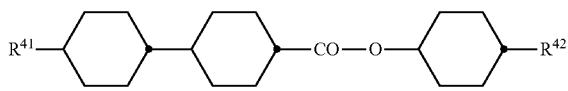
CC8

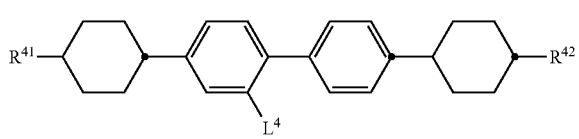
CC9

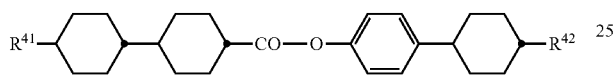
CC10

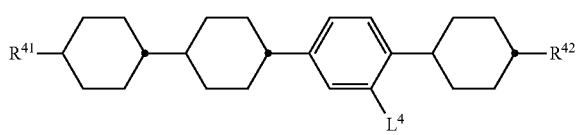
CC11

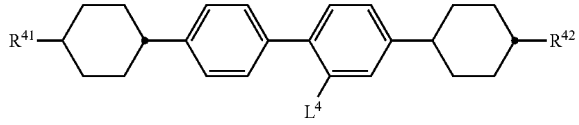
CC12

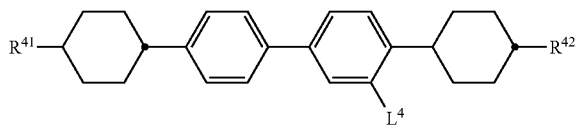
CC13

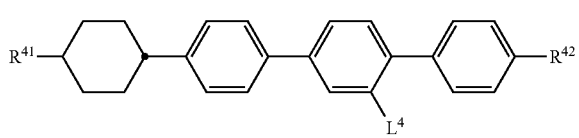
CC14 in which $R^{41}$ and $R^{42}$ have the meanings indicated in formula CC and preferably each, independently of one another, denote alkyl, alkoxy, fluorinated alkyl or fluorinated alkoxy having 1 to 7 C atoms, or alkenyl, alkenyloxy, alkoxyalkyl or fluorinated alkenyl having 2 to 7 C atoms, and $L^4$ denotes H or F.

In addition or alternatively to the compounds of the formula CC, the LC medium in accordance with this second preferred embodiment preferably comprises one or more dielectrically neutral compounds having a dielectric anisotropy of −1.5 to +3 which are selected from the group consisting of compounds of the formula DD,

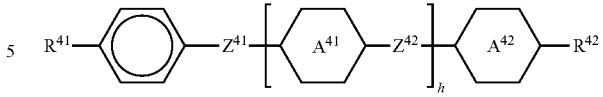
DD in which $A^{41}$, $A^{42}$, $Z^{41}$, $Z^{42}$, $R^{41}$, $R^{42}$ and h have the meanings indicated in formula CC.

Particularly preferred compounds of the formula DD are selected from the group consisting of the following sub-formulae:

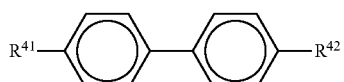
DD1

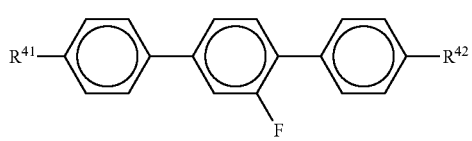
DD2 in which $R^{41}$ and $R^{42}$ have the meanings indicated in formula DD and $R^{41}$ preferably denotes alkyl and, in formula DD1, $R^{42}$ preferably denotes alkenyl, particularly preferably —(CH$_2$)$_2$—CH═CH—CH$_3$, and, in formula DD2, $R^{42}$ preferably denotes alkyl, —(CH$_2$)$_2$—CH═CH$_2$ or —(CH$_2$)$_2$—CH═CH—CH$_3$.

The concentration of the compounds of the formulae AA and BB in the LC medium according to the invention is preferably 2% to 60%, particularly preferably 3% to 35%, very particularly preferably 4% to 30% of the mixture as a whole.

The concentration of the compounds of the formulae CC and DD in the LC medium according to the invention is preferably 2% to 70%, in particular 5% to 65%, particularly preferably 10% to 60%, and very particularly preferably 10%, preferably 15%, to 50% of the mixture as a whole.

The combination of low-molecular-weight compounds as constituent of the LC host mixture in accordance with the preferred embodiments mentioned above with the polymerised compounds described above causes low threshold voltages, low rotational viscosities and very good low-temperature stabilities in the LC media according to the invention at the same time as constantly high clearing points and high HR values, and allows the rapid establishment of a particularly low pretilt angle in PSA displays. In particular, the LC media exhibit significantly shortened response times, in particular also the grey-shade response times, in PSA displays compared with the media from the prior art.

The liquid-crystal mixture preferably has a nematic phase range of at least 80 K, particularly preferably at least 100 K, and a rotational viscosity of not greater than 250 mPa·s, preferably not greater than 200 mPa·s, at 20° C.

In the VA-type displays according to the invention, the molecules in the layer of the LC medium in the switched-off state are aligned perpendicular to the electrode surfaces (homeotropically) or have a tilted homeotropic alignment. On application of an electrical voltage to the electrodes, a realignment of the LC molecules takes place with the longitudinal molecular axes parallel to the electrode surfaces.

LC media according to the invention of the first preferred embodiment, in particular those for use in displays of the PSA-VA type, have a negative dielectric anisotropy Δ∈, preferably from about −0.5 to −10, in particular from about −2.5 to 7.5, at 20° C. and 1 kHz.

The birefringence Δn in LC media according to the invention of the first preferred embodiment, in particular in those for use in displays of the PSA-VA type, is preferably less than 0.16, particularly preferably between 0.06 and 0.14, in particular between 0.07 and 0.12.

In the OCB-type displays according to the invention, the molecules in the layer of the LC medium have a "bend" alignment. On application of an electrical voltage, a realignment of the LC molecules takes place with the longitudinal molecular axes perpendicular to the electrode surfaces.

LC media according to the invention for use in displays of the PSA-OCB type are preferably those having a positive dielectric anisotropy Δ∈ in accordance with the second preferred embodiment, and preferably have a dielectric anisotropy Δ∈ of about +4 to +17 at 20° C. and 1 kHz.

The birefringence Δn in LC media according to the invention of the second preferred embodiment for use in displays of the OCB type is preferably between 0.14 and 0.22, in particular between 0.16 and 0.22.

LC media according to the invention of the second preferred embodiment, in particular those for use in displays of the PSA-TN, PSA-positive-VA, PSA-IPS and PSA-FFS type, have a positive dielectric anisotropy Δ∈, preferably of +2 to +30, particularly preferably of +2 to +17, very particularly preferably of +3 to +15, at 20° C. and 1 kHz.

The birefringence Δn in LC media according to the invention of the second preferred embodiment, in particular in those for use in displays of the PSA-TN, PSA-IPS and PSA-FFS type, is preferably between 0.07 and 0.15, in particular between 0.08 and 0.13.

The LC media according to the invention may also comprise further additives which are known to the person skilled in the art and are described in the literature, such as, for example, polymerisation initiators, inhibitors, stabilisers, surface-active substances or chiral dopants. These may be polymerisable or non-polymerisable. Polymerisable additives are accordingly ascribed to the polymerisable component or component A). Non-polymerisable additives are accordingly ascribed to the non-polymerisable component or component B).

The LC media may, for example, comprise one or more chiral dopants, preferably those selected from the group consisting of compounds from Table B below.

Furthermore, it is possible to add to the LC media, for example, 0 to 15% by weight of pleochroic dyes, furthermore nanoparticles, conductive salts, preferably ethyldimethyldodecylammonium 4-hexoxybenzoate, tetrabutylammonium tetraphenylborate or complex salts of crown ethers (cf., for example, Haller et al., Mol. Cryst. Liq. Cryst. 24, 249-258 (1973)), for improving the conductivity, or substances for modifying the dielectric anisotropy, the viscosity and/or the alignment of the nematic phases. Substances of this type are described, for example, in DE-A 22 09 127, 22 40 864, 23 21 632, 23 38 281, 24 50 088, 26 37 430 and 28 53 728.

The individual components of the preferred embodiments a)-z) of the LC media according to the invention are either known or methods for the preparation thereof can readily be derived from the prior art by the person skilled in the relevant art, since they are based on standard methods described in the literature. Corresponding compounds of the formula CY are described, for example, in EP-A-0 364 538. Corresponding compounds of the formula ZK are described, for example, in DE-A-26 36 684 and DE-A-33 21 373.

The LC media which can be used in accordance with the invention are prepared in a manner conventional per se, for example by mixing one or more of the above-mentioned compounds with one or more polymerisable compounds as defined above, and optionally with further liquid-crystalline compounds and/or additives. In general, the desired amount of the components used in lesser amount is dissolved in the components making up the principal constituent, advantageously at elevated temperature. It is also possible to mix solutions of the components in an organic solvent, for example in acetone, chloroform or methanol, and to remove the solvent again, for example by distillation, after thorough mixing. The invention furthermore relates to the process for the preparation of the LC media according to the invention.

It goes without saying to the person skilled in the art that the LC media according to the invention may also comprise compounds in which, for example, H, N, O, Cl, F have been replaced by the corresponding isotopes.

The structure of the LC displays according to the invention corresponds to the usual geometry for PSA displays, as described in the prior art cited at the outset. Geometries without protrusions are preferred, in particular those in which, in addition, the electrode on the colour filter side is unstructured and only the electrode on the TFT side has slots. Particularly suitable and preferred electrode structures for PSA-VA displays are described, for example, in US 2006/0066793 A1.

The following examples explain the present invention without restricting it. However, they show the person skilled in the art preferred mixture concepts with compounds preferably to be employed and the respective concentrations thereof and combinations thereof with one another. In addition, the examples illustrate which properties and property combinations are accessible.

The following abbreviations are used:
(m, m, z: in each case, independently of one another, 1, 2, 3, 4, 5 or 6)

TABLE A

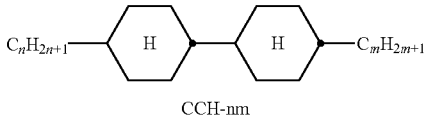

CCH-nm

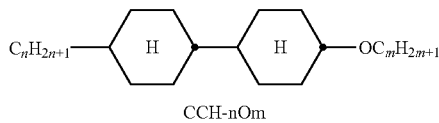

CCH-nOm

TABLE A-continued
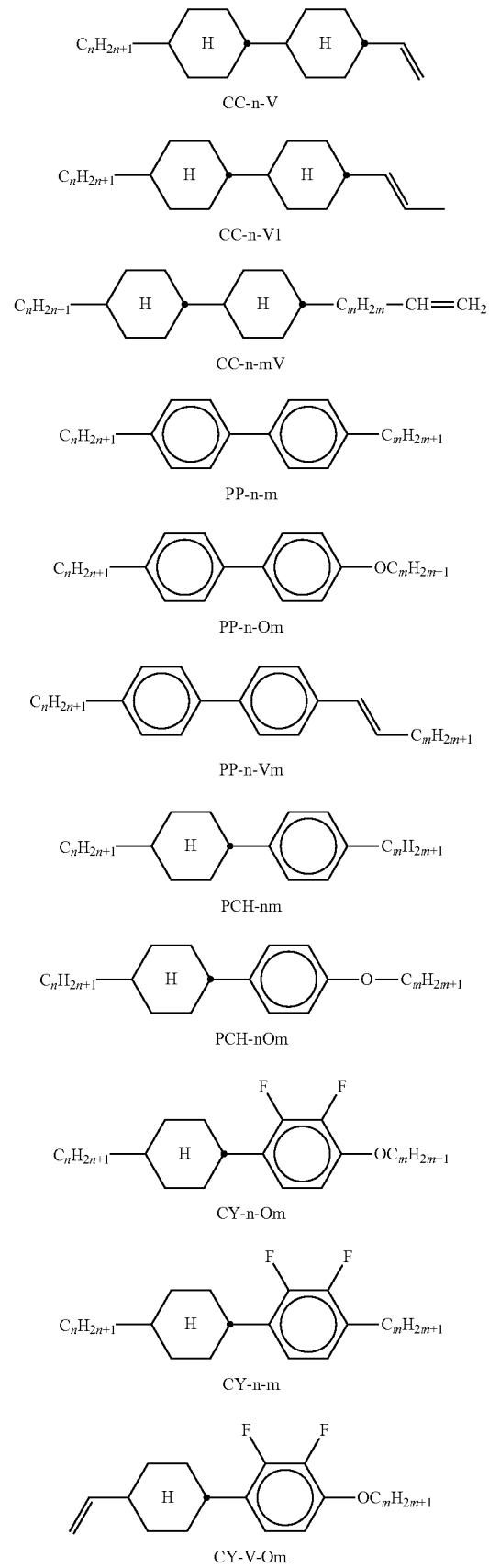

TABLE A-continued
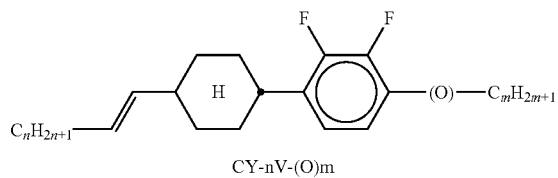
CY-nV-(O)m
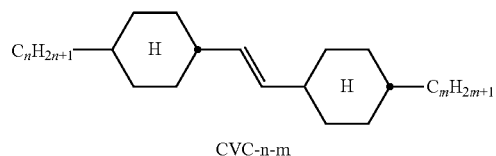
CVC-n-m
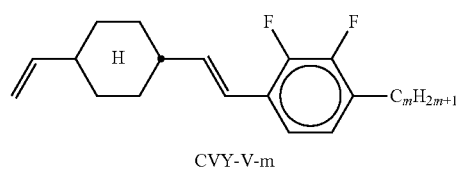
CVY-V-m
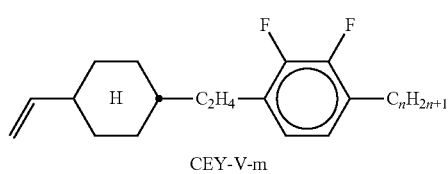
CEY-V-m
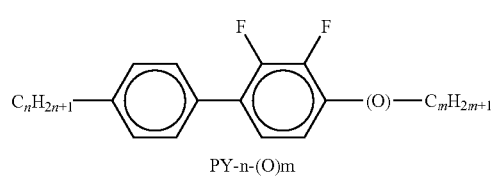
PY-n-(O)m
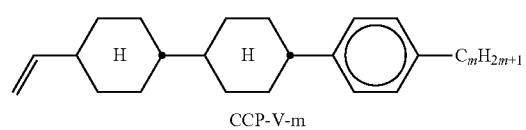
CCP-V-m
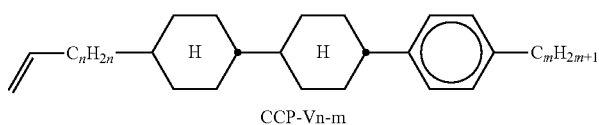
CCP-Vn-m
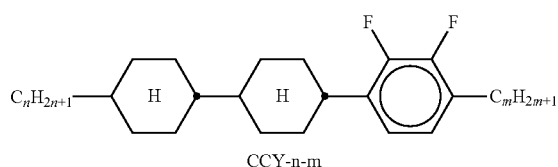
CCY-n-m
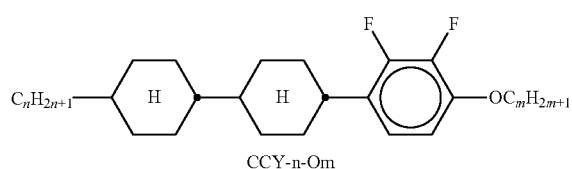
CCY-n-Om TABLE A-continued
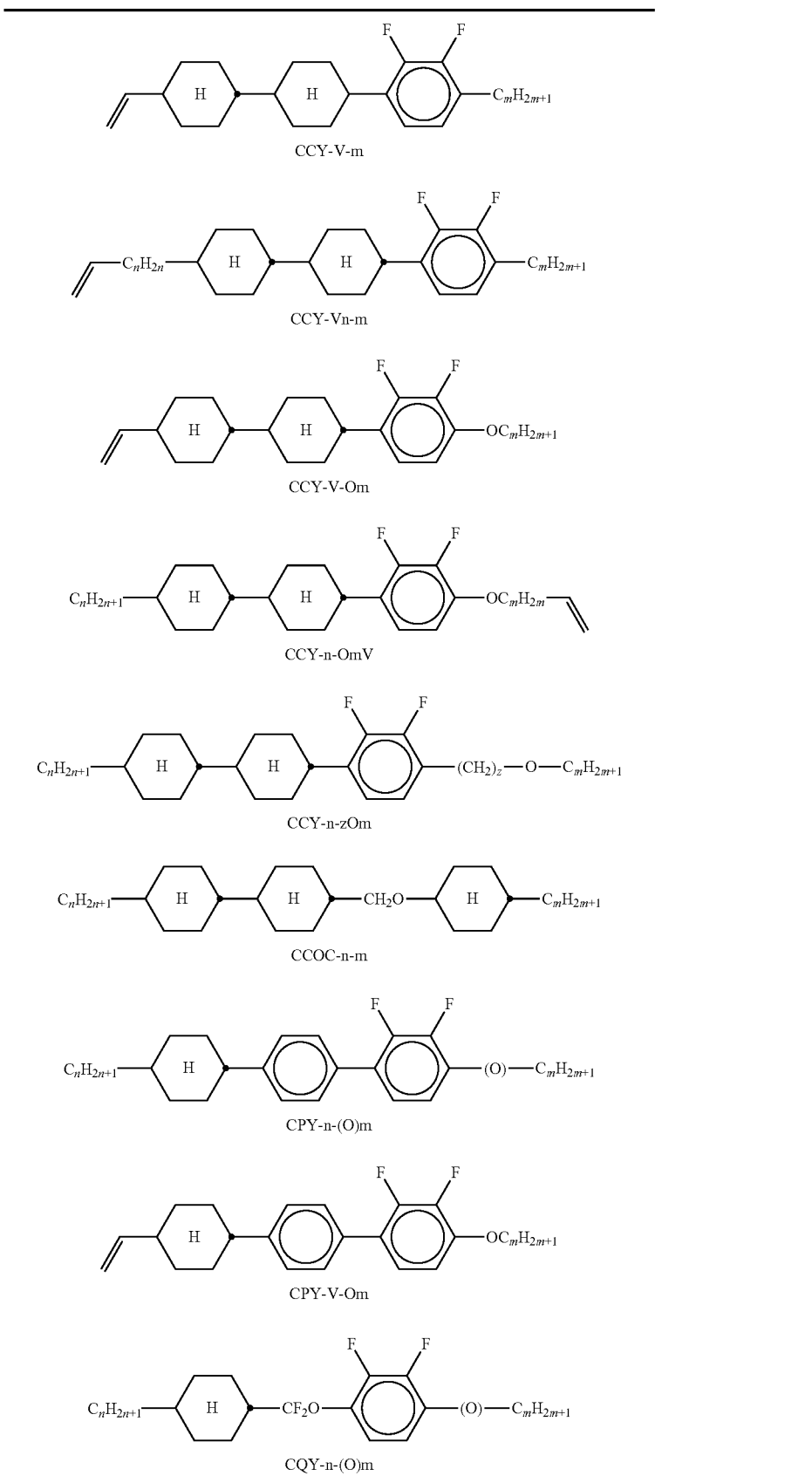

TABLE A-continued
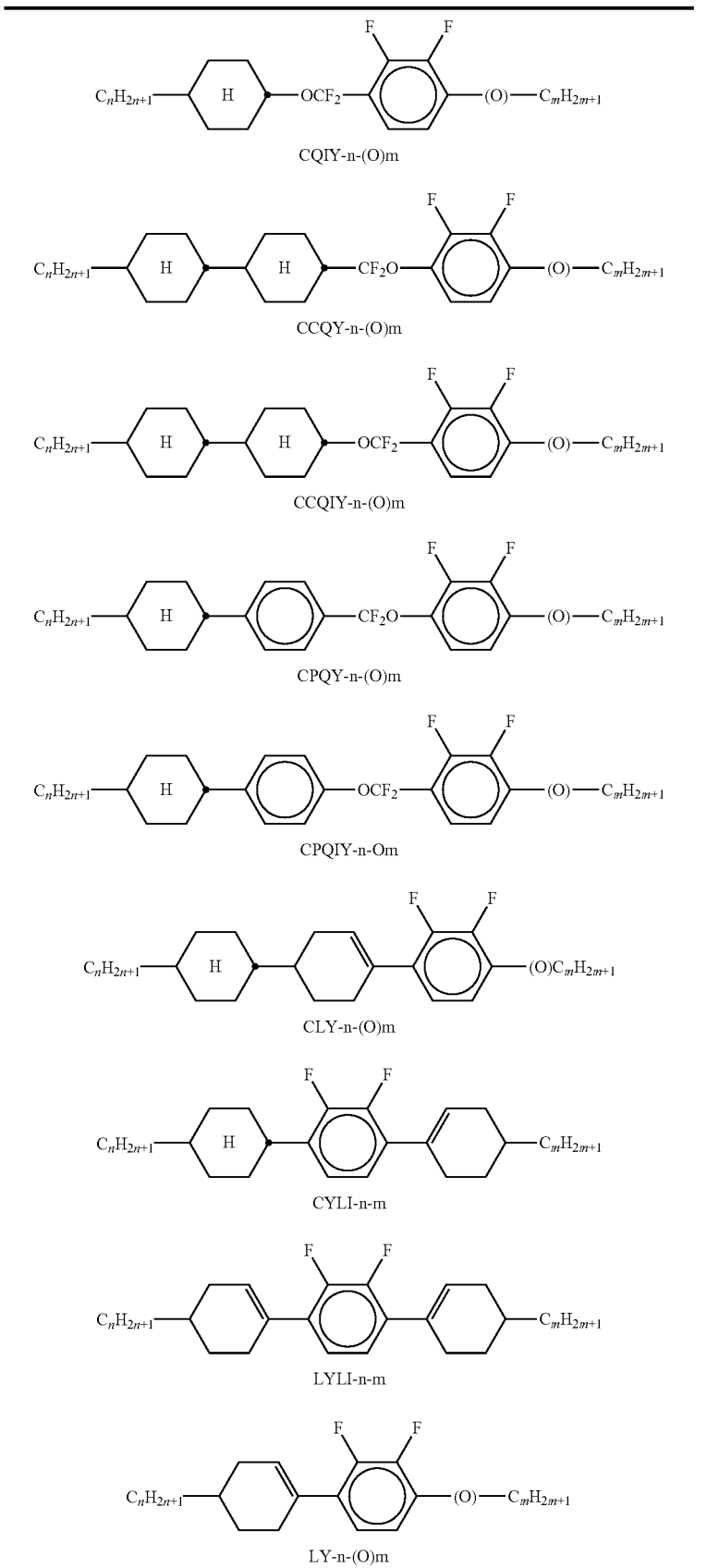

TABLE A-continued
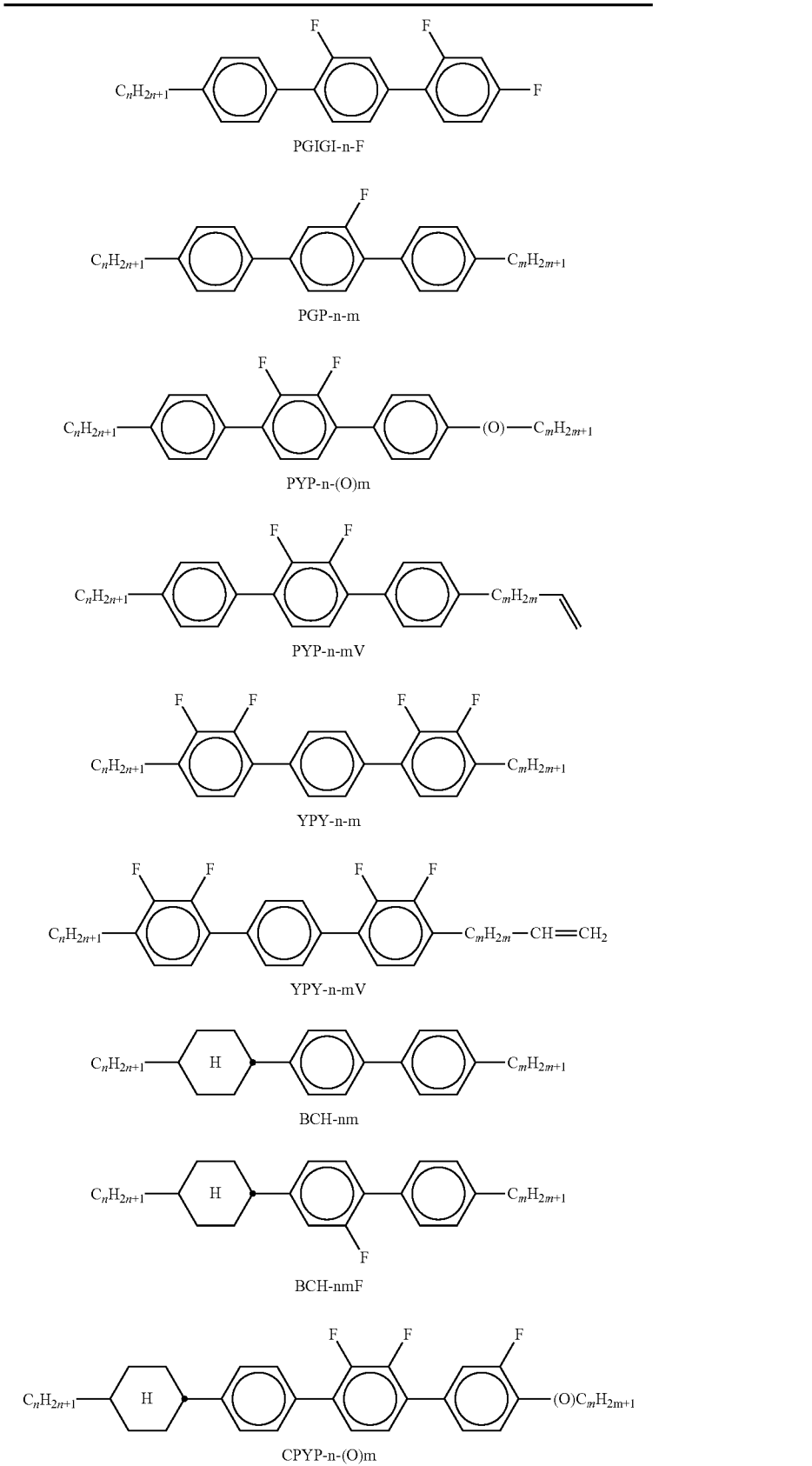

TABLE A-continued
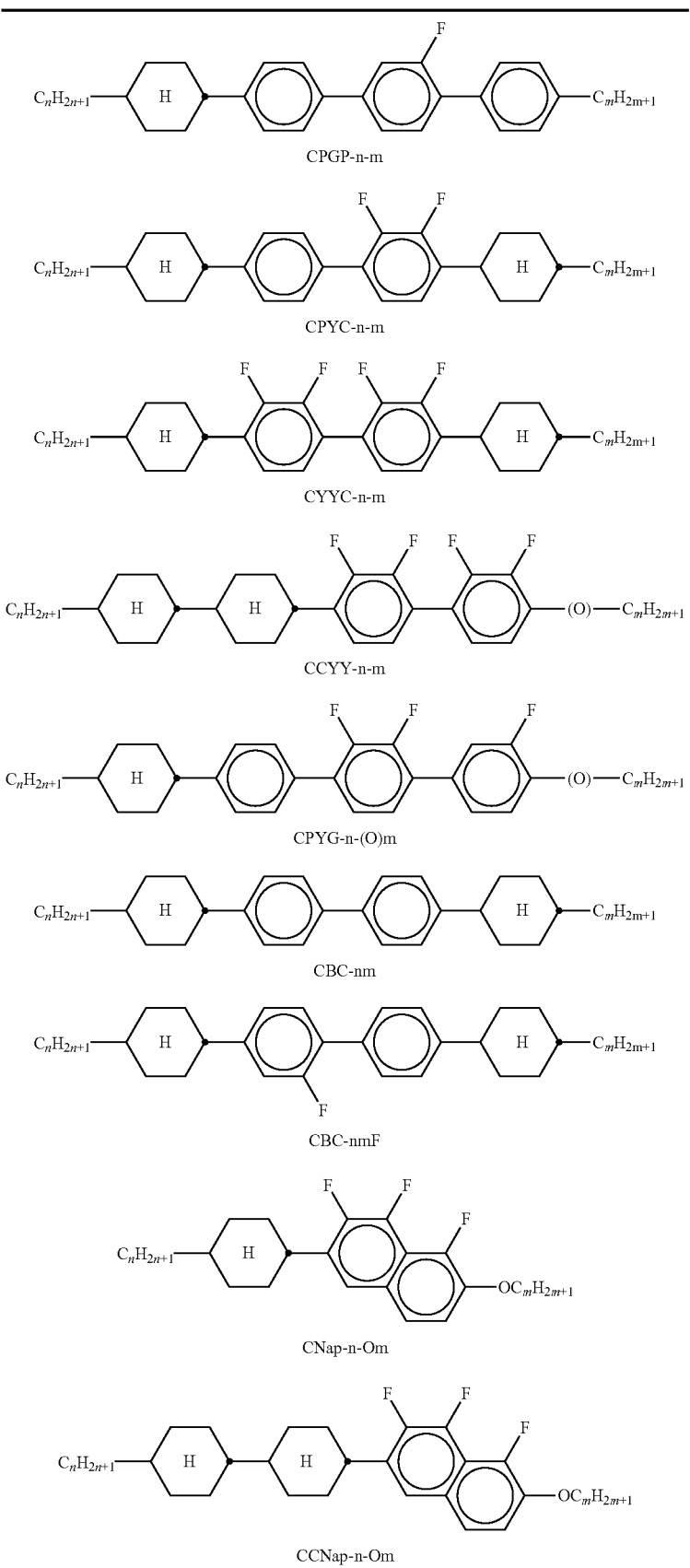

TABLE A-continued
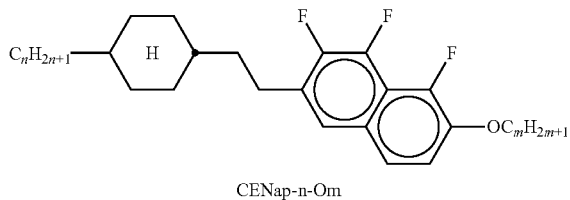
CENap-n-Om
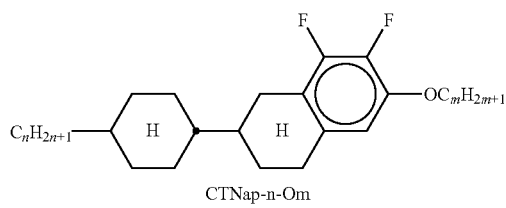
CTNap-n-Om
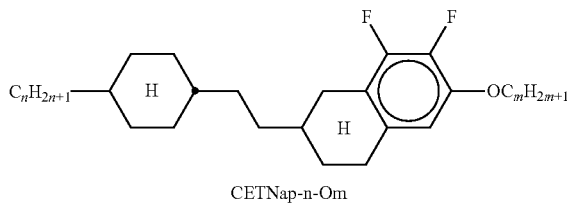
CETNap-n-Om
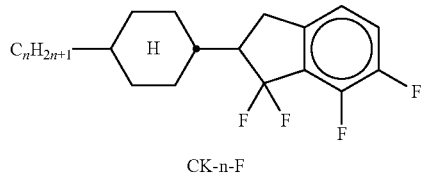
CK-n-F
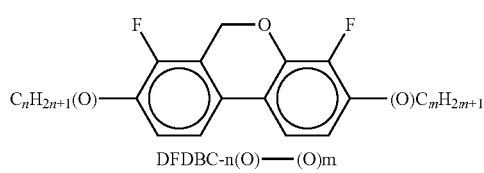
DFDBC-n(O)—(O)m
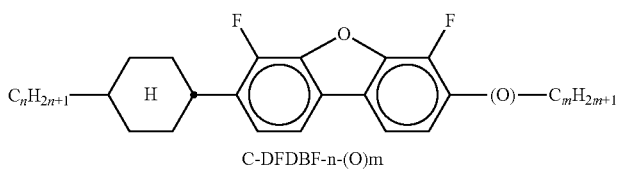
C-DFDBF-n-(O)m
In a preferred embodiment of the present invention, the LC media according to the invention comprise one or more compounds selected from the group consisting of compounds from Table A.
TABLE B
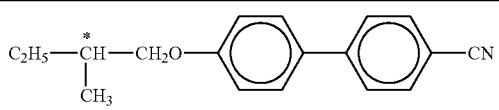
C 15

TABLE B-continued
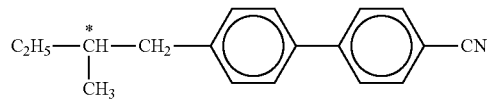
CB 15
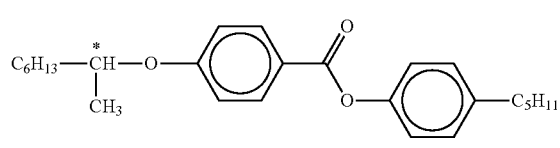
CM 21
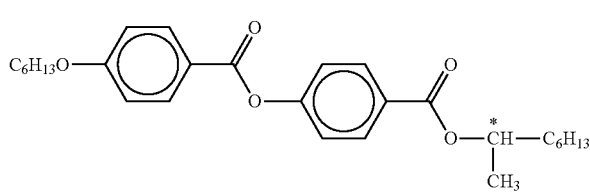
R/S-811
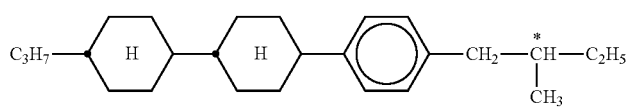
CM 44
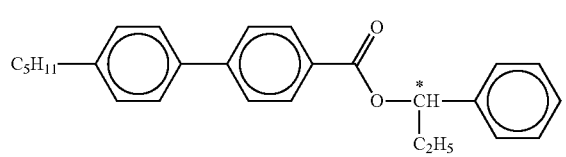
CM 45
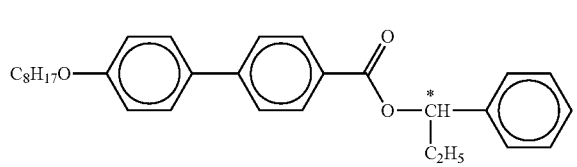
CM 47
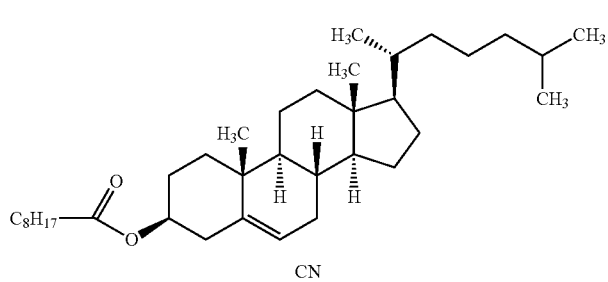
CN
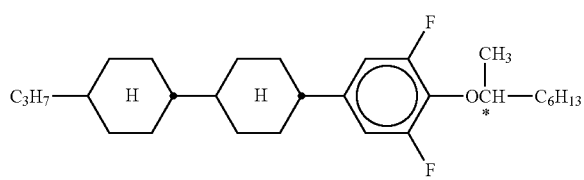
R/S-2011

TABLE B-continued

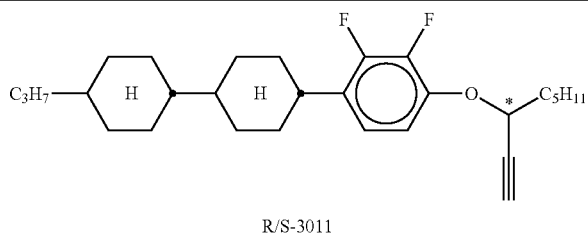

R/S-3011

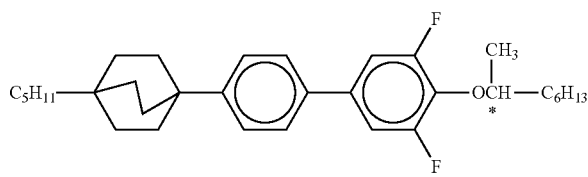

R/S-4011

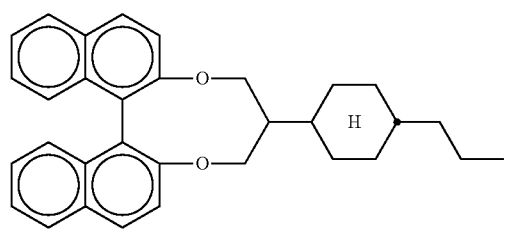

R/S-5011

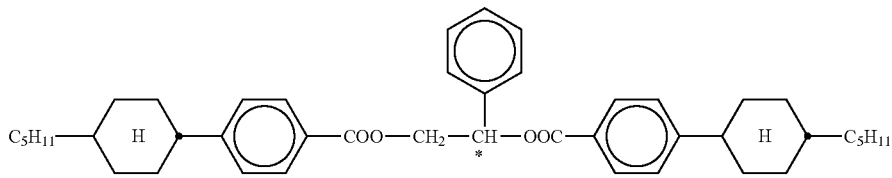

R/S-1011

Table B shows possible chiral dopants which can be added to the LC media according to the invention.

The LC media preferably comprise 0 to 10% by weight, in particular 0.01 to 5% by weight, particularly preferably 0.1 to 3% by weight, of dopants. The LC media preferably comprise one or more dopants selected from the group consisting of compounds from Table B.

TABLE C

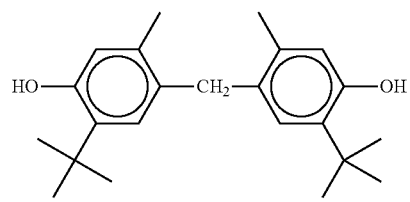

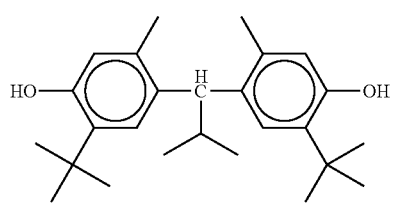

TABLE C-continued
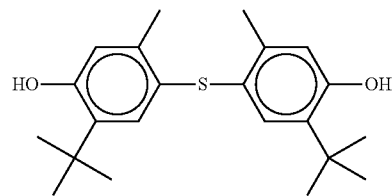
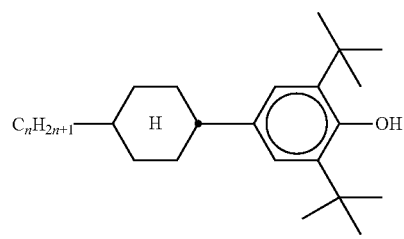
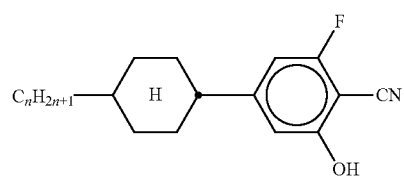
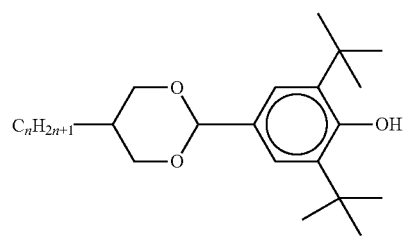
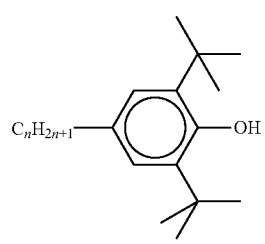
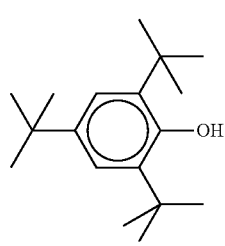
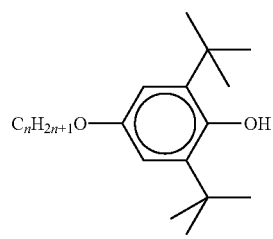

TABLE C-continued
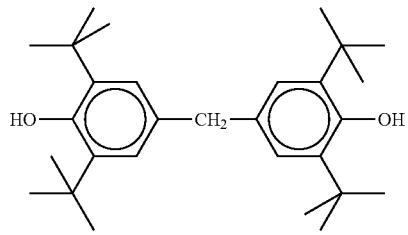
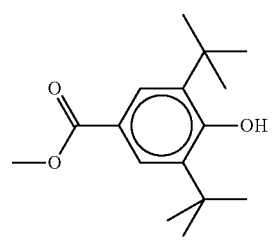
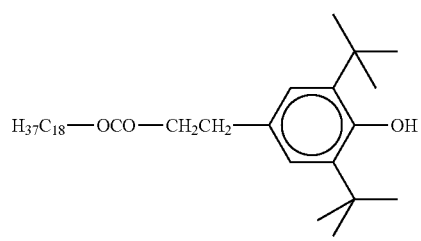
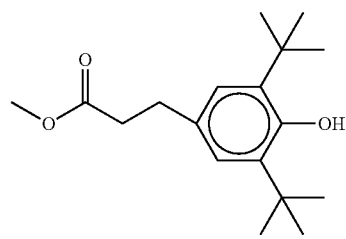
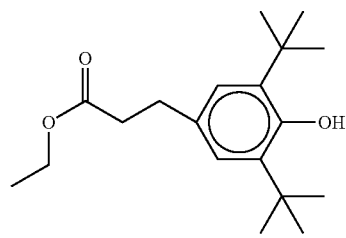
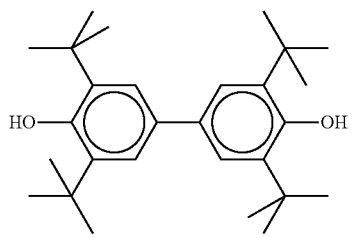

TABLE C-continued
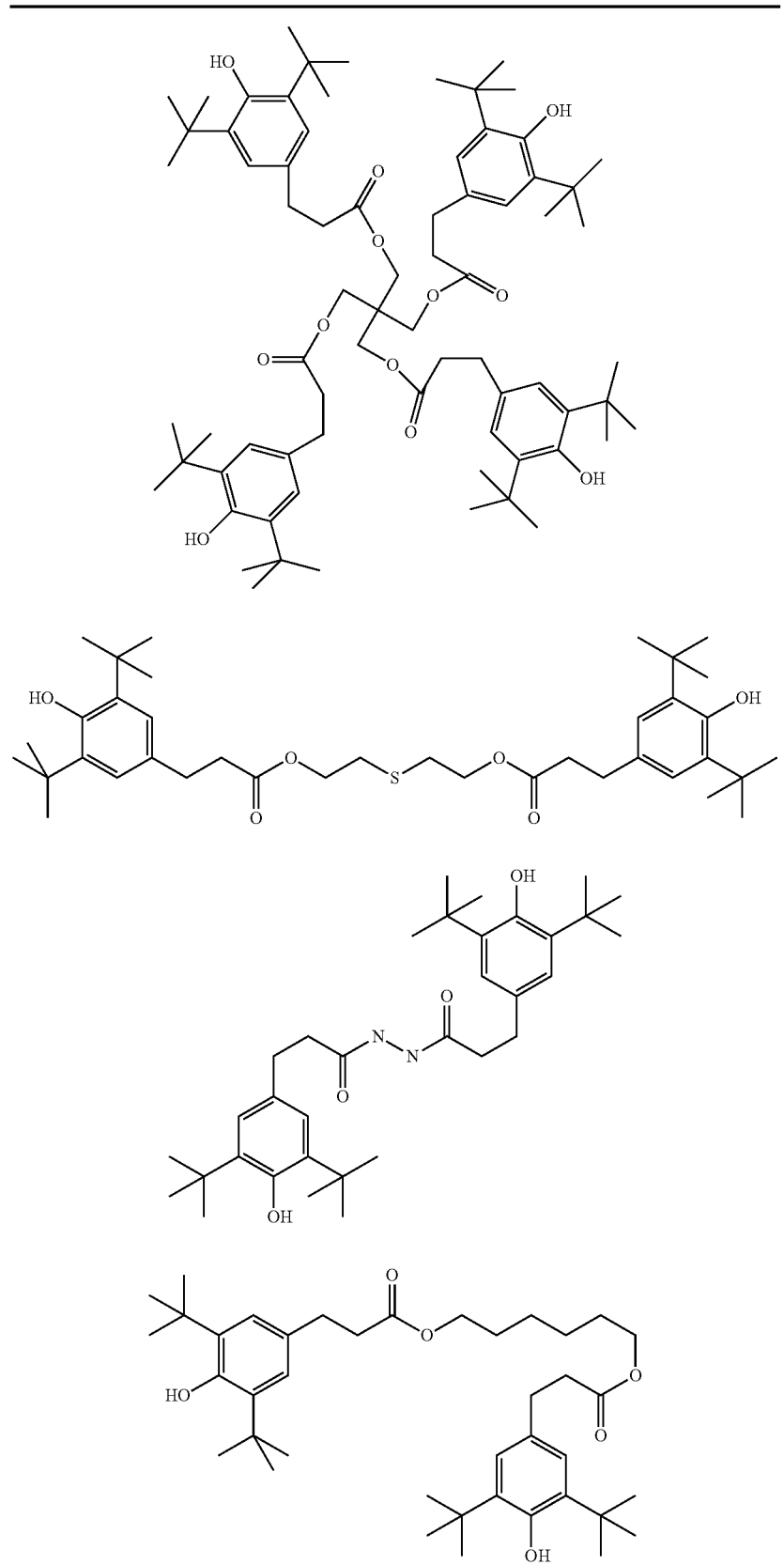

TABLE C-continued
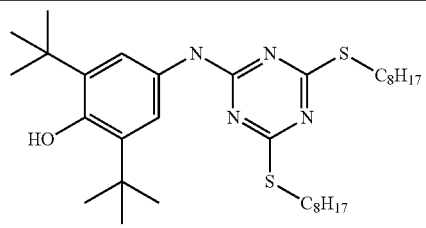
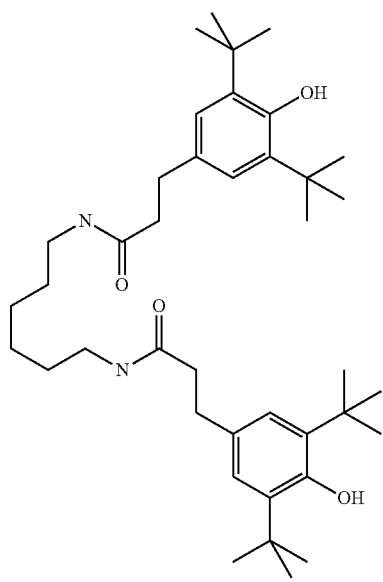 [SMILES: CC(C)(C)c1cc(CCC(=O)NCCCCCCNC(=O)CCc2cc(C(C)(C)C)c(O)c(C(C)(C)C)c2)cc(C(C)(C)C)c1O]
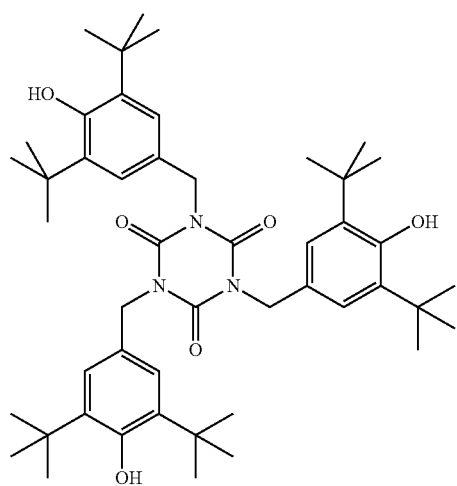 [SMILES: CC(C)(C)c1cc(Cn2c(=O)n(Cc3cc(C(C)(C)C)c(O)c(C(C)(C)C)c3)c(=O)n(Cc3cc(C(C)(C)C)c(O)c(C(C)(C)C)c3)c2=O)cc(C(C)(C)C)c1O]
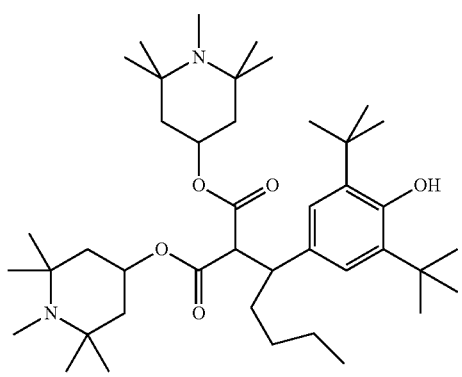 [SMILES: CCCCC(c1cc(C(C)(C)C)c(O)c(C(C)(C)C)c1)C(C(=O)OC1CC(C)(C)N(C)C(C)(C)C1)C(=O)OC1CC(C)(C)N(C)C(C)(C)C1]

TABLE C-continued
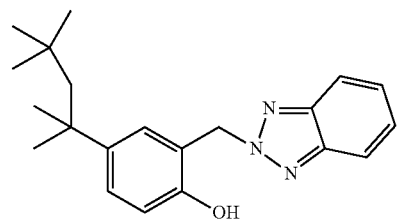 [SMILES: CC(C)(C)CC(C)(C)c1ccc(O)c(Cn2nc3ccccc3n2)c1]
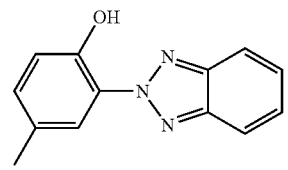 [SMILES: Cc1ccc(O)c(-n2nc3ccccc3n2)c1]
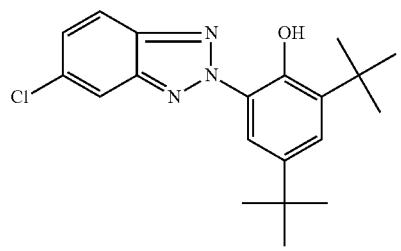 [SMILES: CC(C)(C)c1cc(-n2nc3ccc(Cl)cc3n2)c(O)c(C(C)(C)C)c1]
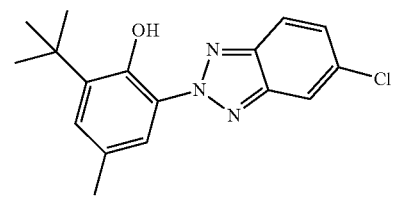 [SMILES: Cc1cc(-n2nc3ccc(Cl)cc3n2)c(O)c(C(C)(C)C)c1]
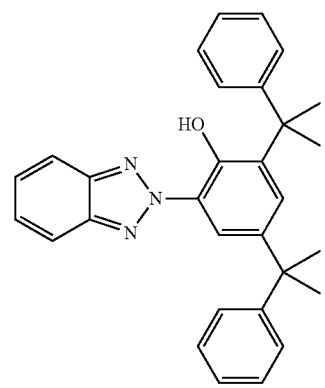 [SMILES: CC(C)(c1ccccc1)c1cc(-n2nc3ccccc3n2)c(O)c(C(C)(C)c2ccccc2)c1]
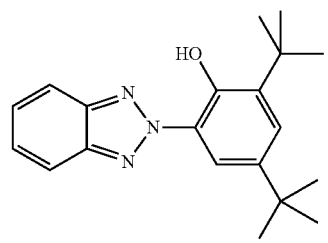 [SMILES: CC(C)(C)c1cc(-n2nc3ccccc3n2)c(O)c(C(C)(C)C)c1]

TABLE C-continued
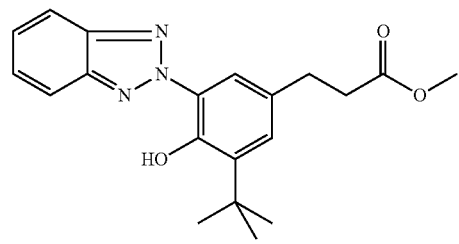 [SMILES: COC(=O)CCc1cc(-n2nc3ccccc3n2)c(O)c(C(C)(C)C)c1]
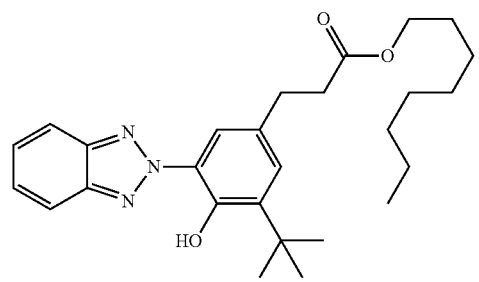 [SMILES: CCCCCCCCOC(=O)CCc1cc(-n2nc3ccccc3n2)c(O)c(C(C)(C)C)c1]
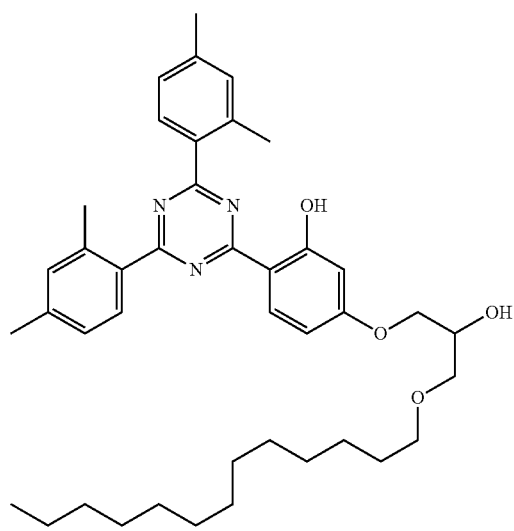 [SMILES: CCCCCCCCCCCCCOCC(O)COc1ccc(-c2nc(-c3ccc(C)cc3C)nc(-c3ccc(C)cc3C)n2)c(O)c1]
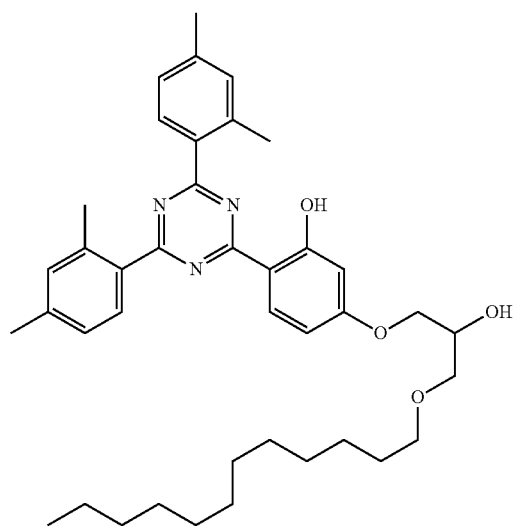 [SMILES: CCCCCCCCCCCCOCC(O)COc1ccc(-c2nc(-c3ccc(C)cc3C)nc(-c3ccc(C)cc3C)n2)c(O)c1]

TABLE C-continued

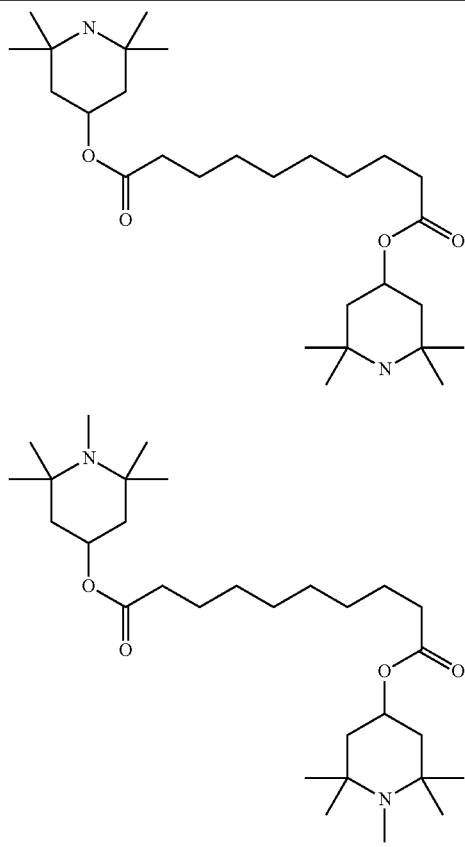

Table C shows possible stabilisers which can be added to the LC media according to the invention.

(n here denotes an integer from 1 to 12, preferably 1, 2, 3, 4, 5, 6, 7 or 8, terminal methyl groups are not shown).

The LC media preferably comprise 0 to 10% by weight, in particular 1 ppm to 5% by weight, particularly preferably 1 ppm to 1% by weight, of stabilisers. The LC media preferably comprise one or more stabilisers selected from the group consisting of compounds from Table C.

TABLE D

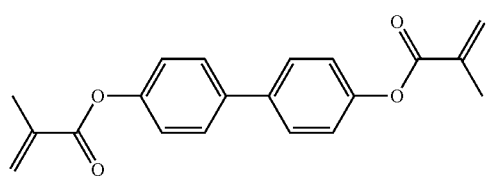 [SMILES: C=C(C)C(=O)Oc1ccc(-c2ccc(OC(=O)C(=C)C)cc2)cc1]

RM-1

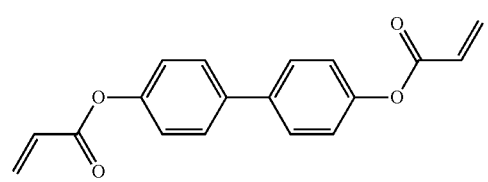 [SMILES: C=CC(=O)Oc1ccc(-c2ccc(OC(=O)C=C)cc2)cc1]

RM-2

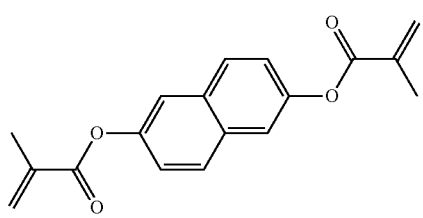 [SMILES: C=C(C)C(=O)Oc1ccc2cc(OC(=O)C(=C)C)ccc2c1]

RM-3

TABLE D-continued
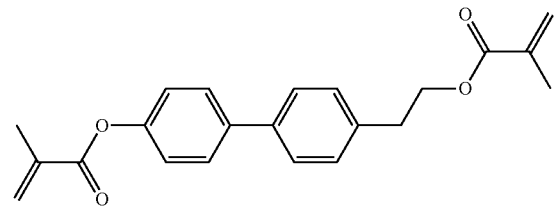 [SMILES: C=C(C)C(=O)OCCc1ccc(-c2ccc(OC(=O)C(=C)C)cc2)cc1]
RM-4
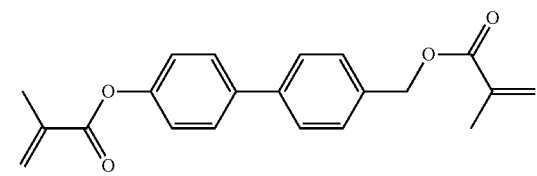 [SMILES: C=C(C)C(=O)OCc1ccc(-c2ccc(OC(=O)C(=C)C)cc2)cc1]
RM-5
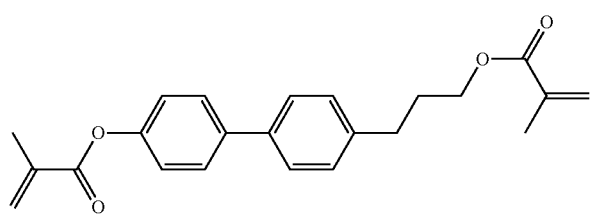 [SMILES: C=C(C)C(=O)OCCCc1ccc(-c2ccc(OC(=O)C(=C)C)cc2)cc1]
RM-6
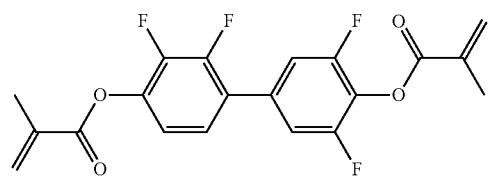 [SMILES: C=C(C)C(=O)Oc1ccc(-c2cc(F)c(OC(=O)C(=C)C)c(F)c2)c(F)c1F]
RM-7
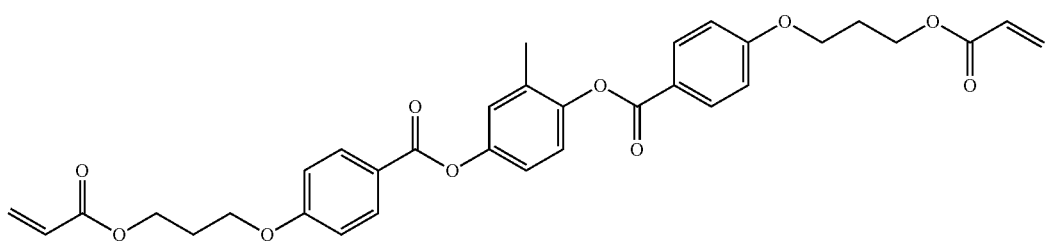 [SMILES: C=CC(=O)OCCCOc1ccc(C(=O)Oc2ccc(OC(=O)c3ccc(OCCCOC(=O)C=C)cc3)c(C)c2)cc1]
RM-8
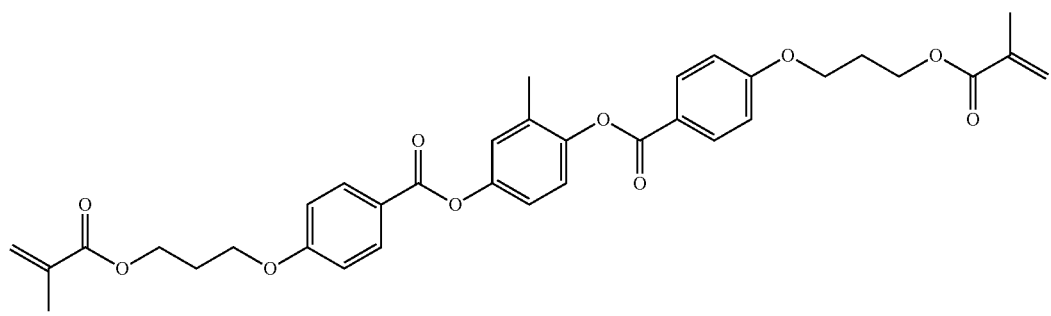 [SMILES: C=C(C)C(=O)OCCCOc1ccc(C(=O)Oc2ccc(OC(=O)c3ccc(OCCCOC(=O)C(=C)C)cc3)c(C)c2)cc1]
RM-9
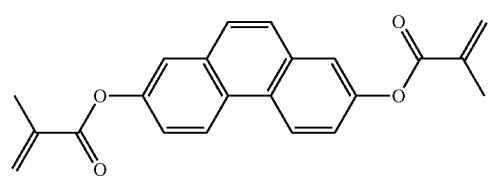 [SMILES: C=C(C)C(=O)Oc1ccc2c(ccc3cc(OC(=O)C(=C)C)ccc32)c1]
RM-10

TABLE D-continued
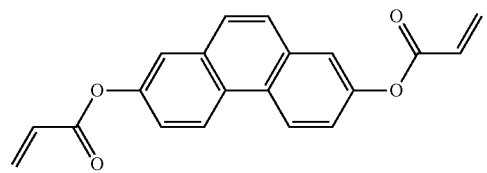 [SMILES: C=CC(=O)Oc1ccc2c(ccc3cc(OC(=O)C=C)ccc32)c1]
RM-11
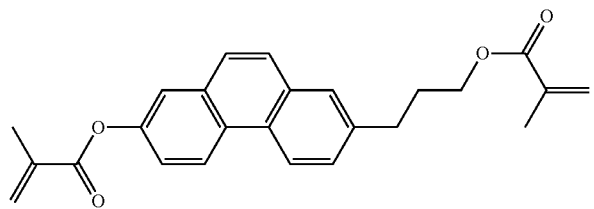 [SMILES: C=C(C)C(=O)OCCCc1ccc2c(ccc3cc(OC(=O)C(=C)C)ccc32)c1]
RM-12
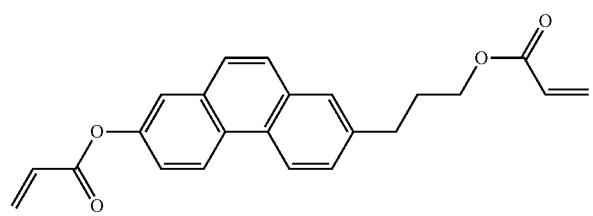 [SMILES: C=CC(=O)OCCCc1ccc2c(ccc3cc(OC(=O)C=C)ccc32)c1]
RM-13
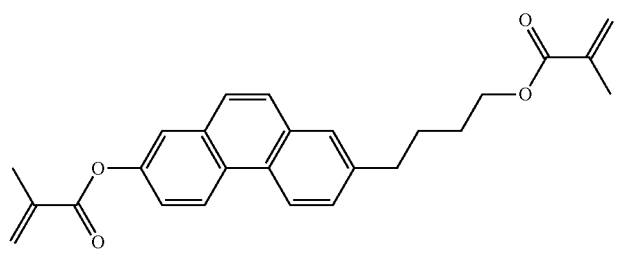 [SMILES: C=C(C)C(=O)OCCCCc1ccc2c(ccc3cc(OC(=O)C(=C)C)ccc32)c1]
RM-14
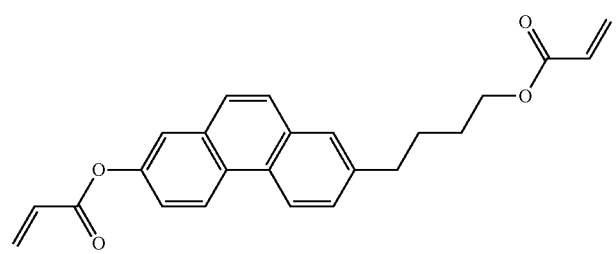 [SMILES: C=CC(=O)OCCCCc1ccc2c(ccc3cc(OC(=O)C=C)ccc32)c1]
RM-15
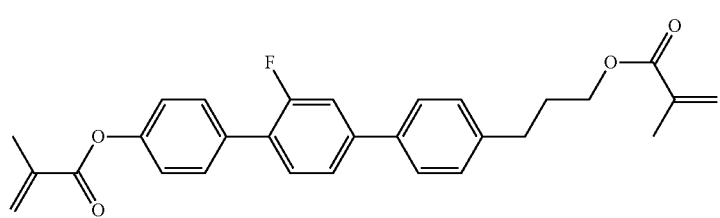 [SMILES: C=C(C)C(=O)OCCCc1ccc(-c2ccc(-c3ccc(OC(=O)C(=C)C)cc3)c(F)c2)cc1]
RM-16
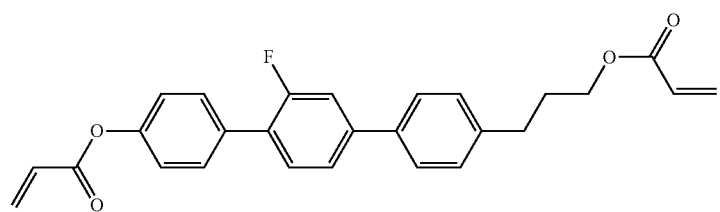
RM-17

TABLE D-continued
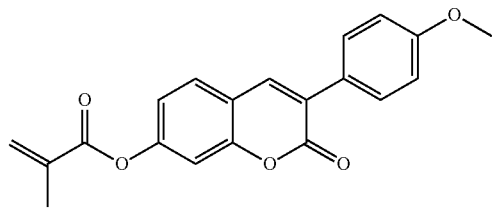 [SMILES: C=C(C)C(=O)Oc1ccc2cc(-c3ccc(OC)cc3)c(=O)oc2c1]
RM-18
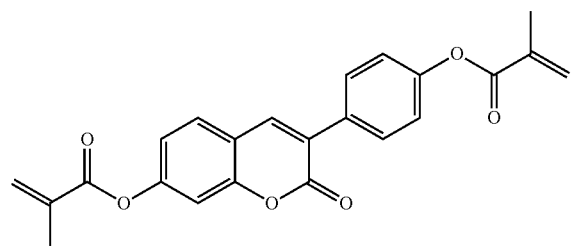 [SMILES: C=C(C)C(=O)Oc1ccc(-c2cc3ccc(OC(=O)C(=C)C)cc3oc2=O)cc1]
RM-19
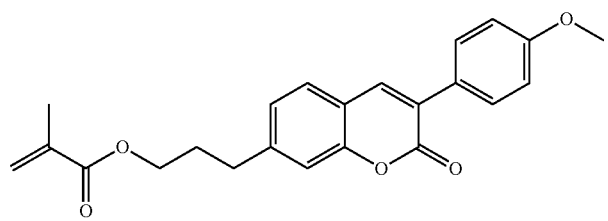 [SMILES: C=C(C)C(=O)OCCCc1ccc2cc(-c3ccc(OC)cc3)c(=O)oc2c1]
RM-20
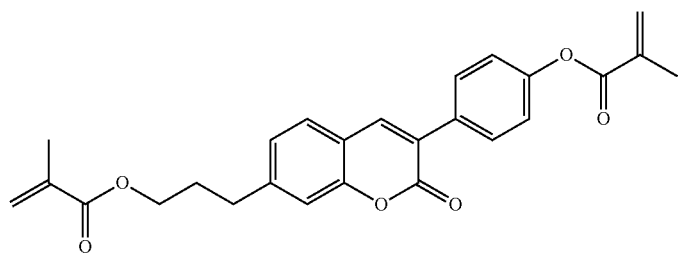 [SMILES: C=C(C)C(=O)OCCCc1ccc2cc(-c3ccc(OC(=O)C(=C)C)cc3)c(=O)oc2c1]
RM-21
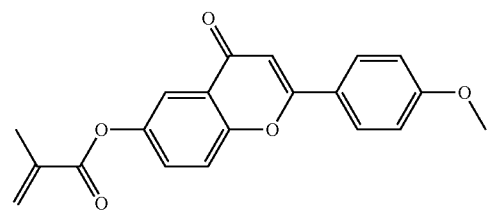 [SMILES: C=C(C)C(=O)Oc1ccc2oc(-c3ccc(OC)cc3)cc(=O)c2c1]
RM-22
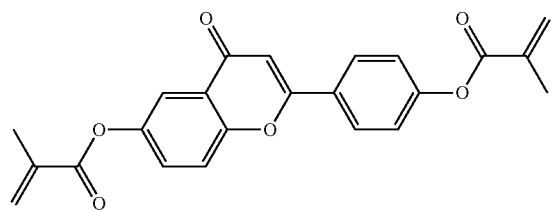 [SMILES: C=C(C)C(=O)Oc1ccc(-c2cc(=O)c3cc(OC(=O)C(=C)C)ccc3o2)cc1]
RM-23

TABLE D-continued
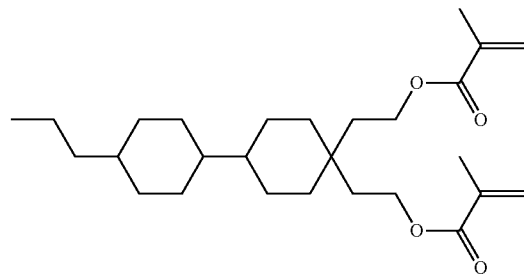 [SMILES: C=C(C)C(=O)OCCC1(CCOC(=O)C(=C)C)CCC(C2CCC(CCC)CC2)CC1]
RM-24
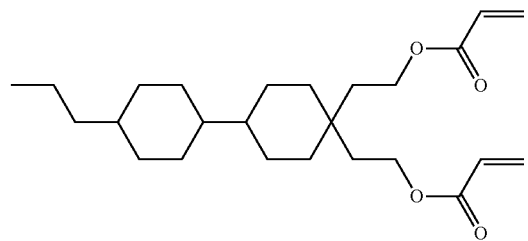 [SMILES: C=CC(=O)OCCC1(CCOC(=O)C=C)CCC(C2CCC(CCC)CC2)CC1]
RM-25
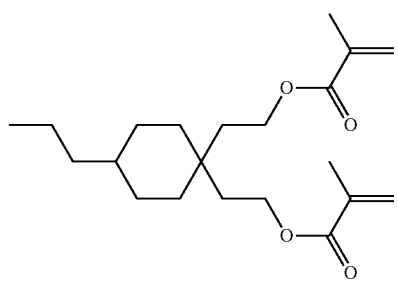 [SMILES: C=C(C)C(=O)OCCC1(CCOC(=O)C(=C)C)CCC(CCC)CC1]
RM-26
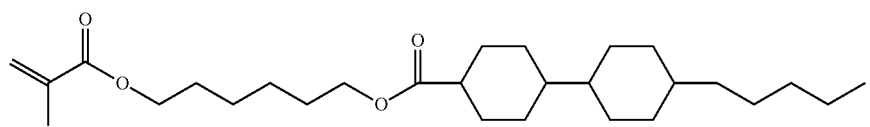 [SMILES: C=C(C)C(=O)OCCCCCCOC(=O)C1CCC(C2CCC(CCCCC)CC2)CC1]
RM-27
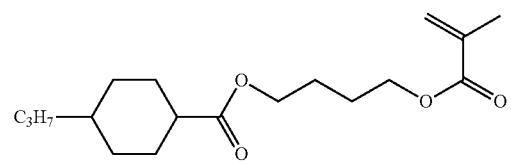
RM-28
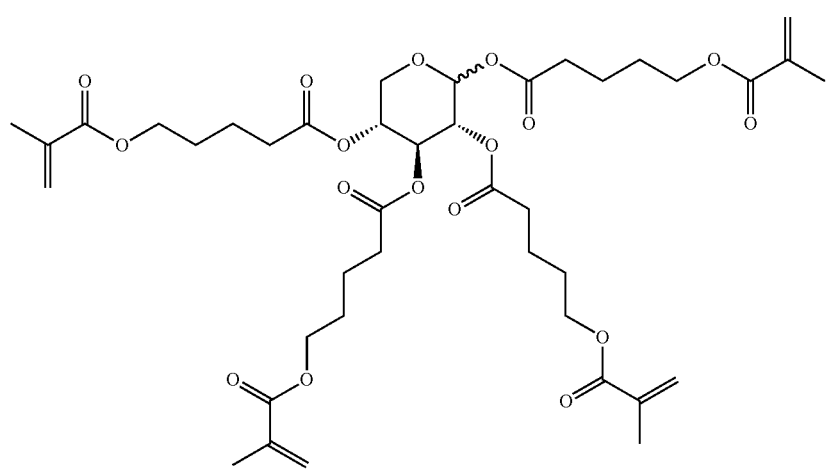 [SMILES: C=C(C)C(=O)OCCCCC(=O)OC1OC[C@@H](OC(=O)CCCCOC(=O)C(=C)C)[C@H](OC(=O)CCCCOC(=O)C(=C)C)[C@H]1OC(=O)CCCCOC(=O)C(=C)C]
RM-29

TABLE D-continued

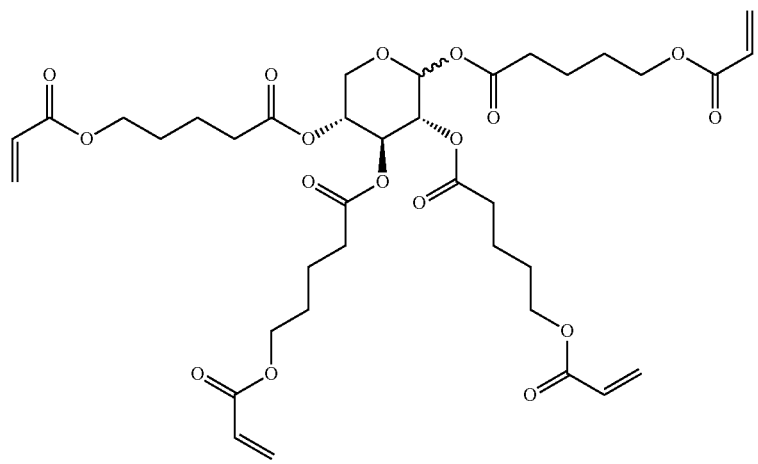 [SMILES: C=CC(=O)OCCCCC(=O)OC1OC[C@@H](OC(=O)CCCCOC(=O)C=C)[C@H](OC(=O)CCCCOC(=O)C=C)[C@H]1OC(=O)CCCCOC(=O)C=C]

RM-30

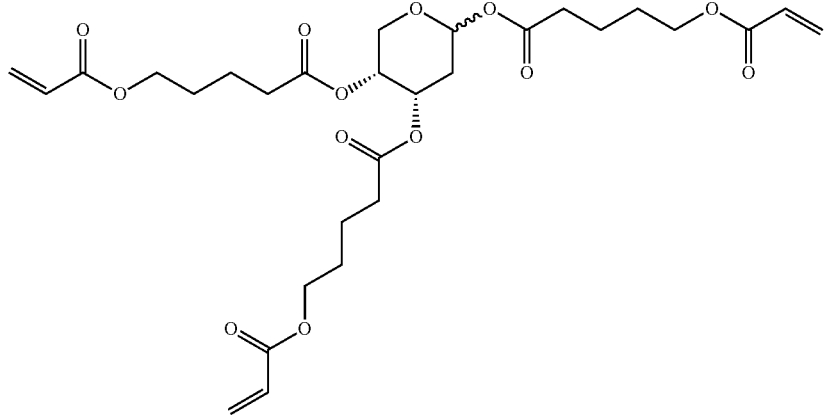 [SMILES: C=CC(=O)OCCCCC(=O)OC1C[C@H](OC(=O)CCCCOC(=O)C=C)[C@H](OC(=O)CCCCOC(=O)C=C)CO1]

RM-31

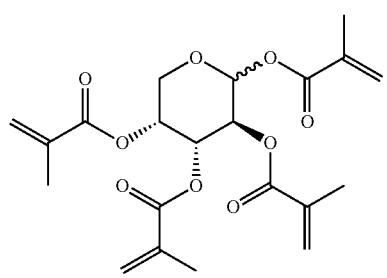 [SMILES: C=C(C)C(=O)OC1OC[C@@H](OC(=O)C(=C)C)[C@@H](OC(=O)C(=C)C)[C@@H]1OC(=O)C(=C)C]

RM-32

Table D shows illustrative compounds which can be used in the LC media in accordance with the present invention, preferably as reactive mesogenic compounds.

In a preferred embodiment of the present invention, the mesogenic media comprise one or more compounds selected from the group of the compounds from Table D.

In addition, the following abbreviations and symbols are used:

$V_0$ threshold voltage, capacitive [V] at 20° C.,
$n_e$ extraordinary refractive index at 20° C. and 589 nm,
$n_o$ ordinary refractive index at 20° C. and 589 nm,
$\Delta n$ optical anisotropy at 20° C. and 589 nm,
$\epsilon_\perp$ dielectric permittivity perpendicular to the director at 20° C. and 1 kHz,
$\epsilon_\parallel$ dielectric permittivity parallel to the director at 20° C. and 1 kHz,
$\Delta\epsilon$ dielectric anisotropy at 20° C. and 1 kHz,
cl.p., T(N,I) clearing point [° C.],
$\gamma_1$ rotational viscosity at 20° C. [mPa·s],
$K_1$ elastic constant, "splay" deformation at 20° C. [pN],
$K_2$ elastic constant, "twist" deformation at 20° C. [pN],
$K_3$ elastic constant, "bend" deformation at 20° C. [pN].

Unless explicitly noted otherwise, all concentrations in the present application are quoted in percent by weight and relate to the corresponding mixture as a whole, i.e. the LC medium comprising all solid or liquid-crystalline components, without solvents.

Unless explicitly noted otherwise, all temperature values indicated in the present application, such as, for example, for the melting point T(C,N), the transition from the smectic (S) to the nematic (N) phase T(S,N) and the clearing point T(N,I), are quoted in degrees Celsius (° C.). M.p. denotes melting point, cl.p.=clearing point. Furthermore, C=crystalline state, N=nematic phase, S=smectic phase and I=isotropic phase. The data between these symbols represent the transition temperatures.

All physical properties are and have been determined in accordance with "Merck Liquid Crystals, Physical Properties of Liquid Crystals", Status November 1997, Merck KGaA, Germany, and apply for a temperature of 20° C., and Δn is determined at 589 nm and Δ∈ at 1 kHz, unless explicitly indicated otherwise in each case.

The term "threshold voltage" for the present invention relates to the capacitive threshold ($V_0$), also known as the Freedericks threshold, unless explicitly indicated otherwise. In the examples, the optical threshold may also, as generally usual, be quoted for 10% relative contrast ($C1_0$).

The display used for measurement of the capacitive threshold voltage consists of two plane-parallel glass outer plates at a separation of 20 µm, each of which has on the inside an electrode layer and an unrubbed polyimide alignment layer on top, which effect a homeotropic edge alignment of the liquid-crystal molecules.

The display or test cell used for measurement of the tilt angles consists of two plane-parallel glass outer plates at a separation of 4 µm, each of which has on the inside an electrode layer and a polyimide alignment layer on top, where the two polyimide layers are rubbed antiparallel to one another and effect a homeotropic edge alignment of the liquid-crystal molecules.

The polymerisable compounds are polymerised in the display or test cell by irradiation with UVA light (usually 365 nm) of defined intensity for a pre-specified time, with a voltage simultaneously being applied to the display (usually 10 V to 30 V alternating current, 1 kHz). In the examples, unless indicated otherwise, a 28 mW/cm² mercury vapour lamp is used, and the intensity is measured using a standard UV meter (model Ushio UNI meter) fitted with a 365 nm band-pass filter.

The tilt angle is determined by crystal rotation experiment (Autronic-Melchers TBA-105). A low value (i.e. a large deviation from the 90° angle) corresponds to a large tilt here.

The VHR value is measured as follows: 0.3% of a polymerisable monomeric compound is added to the LC host mixture, and the resultant mixture is introduced into TN-VHR test cells (rubbed at 90°, TN-polyimide alignment layer, layer thickness d≈6 µm). The HR value is determined after 5 min at 100° C. before and after UV exposure for 2 h (suntest) at 1 V, 60 Hz, 64 µs pulse (measuring instrument: Autronic-Melchers VHRM-105).

In order to investigate the low-temperature stability, also referred to as "LTS", i.e. the stability of the LC mixture to individual components spontaneously crystallising out at low temperatures, bottles containing 1 g of LC/RM mixture are placed in storage at −10° C., and it is regularly checked whether the mixtures have crystallised out.

EXAMPLE 1

4-[4-(2-Methylacryloyloxy)phenylethynyl]benzyl 2-methylacrylate 1.1 4-(4-Hydroxymethylphenylethynyl)phenol

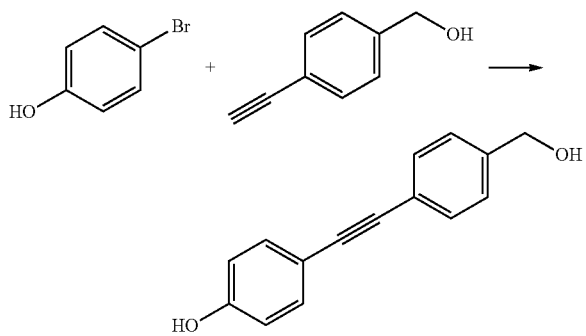

6.50 g (37.6 mmol) of 4-bromophenol and 5.00 g (37.8 mmol) of 4-ethynylbenzyl alcohol are initially introduced in 70 ml of THF and 10 ml of diisopropylamine, and, after addition of 1.50 g (2.14 mmol) of bis(triphenylphosphine)palladium(II) chloride and 0.40 g (2.10 mmol) of copper(I) iodide, the mixture is heated under reflux overnight. After addition of 100 ml of ethyl acetate, the mixture is acidified using 2 M hydrochloric acid, the aqueous phase is extracted three times with ethyl acetate, and the combined org. phases are dried over sodium sulfate. The solvent is removed in vacuo, and the residue is purified by chromatography on silica gel, giving 4-(4-hydroxymethylphenylethynyl)phenol as a colourless solid.

$^1$H-NMR (400 MHz, DMSO-$d_6$)

δ=4.52 ppm (s, 2H, CH$_2$), 5.27 (s, br., 1H, OH), 6.79 (d, J=8.7 Hz, 2H, Ar—H), 7.34 (d, J=8.1 Hz, 2H, Ar—H), 7.36 (d, J=8.7 Hz, 2H, Ar—H), 7.45 (d, J=8.1 Hz, 2H, Ar—H), 9.93 (s, br., 1H, OH).

1.2 4-[4-(2-Methylacryloyloxy)phenylethynyl]benzyl 2-methylacrylate

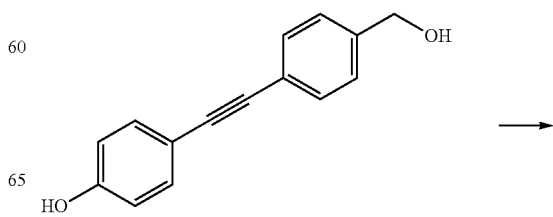

-continued

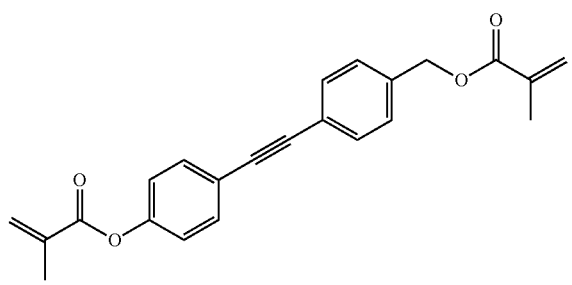

4-(4-Hydroxymethylphenylethynyl)phenol and 2.5 ml of triethylamine are initially introduced in 40 ml of dichloromethane, and a solution of 1.5 g (14 mmol) of acryloyl chloride is added with ice-cooling. After 3 h, the batch is filtered through silica gel, and the solvent is removed in vacuo. Crystallisation of the crude product from ethanol gives 4-[4-(2-methylacryloyloxy)phenylethynyl]benzyl 2-methylacrylate as colourless crystals of m.p. 65° C.

EXAMPLE 2

6-{4-[3-(2-Methylacryloyloxy)propyl]phenylethynyl}naphthalen-2-yl 2-methylacrylate 2.1 2-Triisopropylsilanyloxy-6-trimethylsilanylethynylnaphthalene

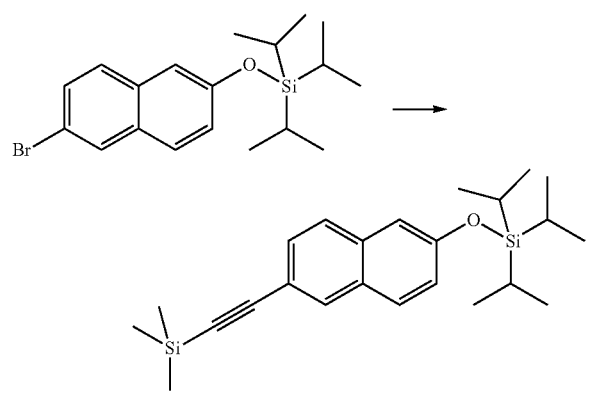

35.0 g (90.4 mmol) of (6-bromonaphthalen-2-yloxy)triisopropylsilane are initially introduced in 120 ml of THF and 70 ml of diisopropylamine, and, after addition of 3.50 g (5.0 mmol) of bis(triphenylphosphine)palladium(II) chloride and 1.0 g (5.3 mmol) of copper(I) iodide, 25.0 g (0.255 mol) of trimethylsilylacetylene in 30 ml of THF are added dropwise at 70° C. The batch is left to stir for 4 h at 70° C. and overnight at room temp., 150 ml of MTB ether are added, and the mixture is washed three times with water, dried over sodium sulfate and evaporated in vacuo. Filtration of the crude product through silica gel with heptane gives 2-triisopropylsilanyloxy-6-trimethylsilanylethynylnaphthalene, which is employed in the next step without further purification.

2.2 (6-Ethynylnaphthalen-2-yloxy)triisopropylsilane

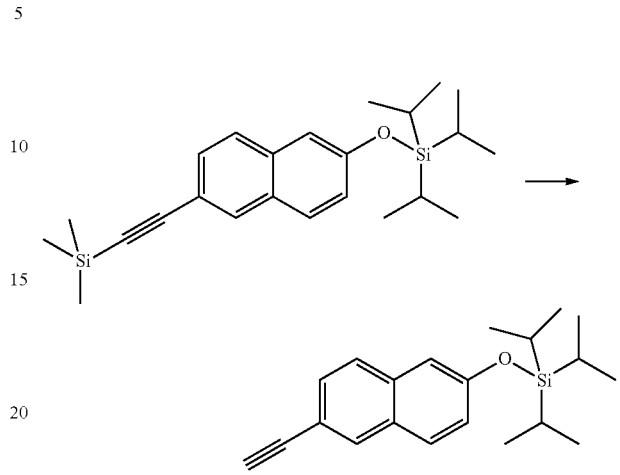

14.5 g (34.7 mmol) of (6-ethynylnaphthalen-2-yloxy)triisopropylsilane are dissolved in 250 ml of hot methanol, and, after addition of 5.2 g (37.6 mmol) of potassium carbonate, the mixture is left to stir for 45 min at room temp. MTB ether and sat. sodium hydrogencarbonate soln. are added to the batch, the org. phase is separated off, and the aqueous phase is extracted three times with MTB ether. The combined org. phases are washed with sat. sodium chloride soln. and dried over sodium sulfate. The solvent is removed in vacuo, and the residue is filtered through silica gel with heptane/toluene (4:1), giving (6-ethynylnaphthalen-2-yloxy)triisopropylsilane as a colourless oil.

2.3 3-[4-(6-Triisopropylsilanyloxynaphthalen-2-yl-ethynyl)phenyl]propan-1-ol

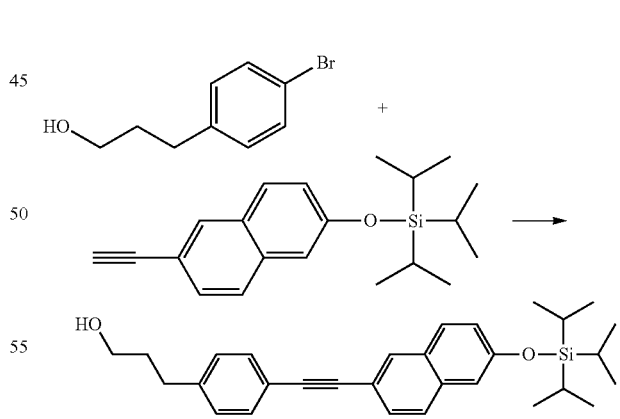

7.0 g (32.5 mmol) of 3-(4-bromophenyl)propan-1-ol are initially introduced in 70 ml of THF and 30 ml of diisopropylamine, and, after addition of 1.0 g (1.4 mmol) of bis(triphenylphosphine)palladium(II) chloride and 0.4 g (2.1 mmol) of copper(I) iodide, 16.4 g (50.5 mmol) of (6-ethynylnaphthalen-2-yloxy)triisopropylsilane in 30 ml of THF are added dropwise at 70° C. The batch is left to stir for 5 h at 70°

C., 200 ml of ethyl acetate are added, and the mixture is washed three times with water. The combined aqueous phases are extracted with ethyl acetate, and the combined org. phases are dried over sodium sulfate and evaporated in vacuo. Chromatography of the crude product on silica gel with firstly toluene and then toluene/ethyl acetate (7:3) gives 2-triisopropylsilanyloxy-6-trimethylsilanylethynylnaphthalene as a brown oil, which is employed in the next step without further purification.

2.4 6-[4-(3-Hydroxypropyl)phenylethynyl]naphthalen-2-ol uct from toluene gives 6-[4-(3-hydroxypropyl)phenylethynyl]naphthalen-2-ol as a colourless solid.

$^1$H-NMR (400 MHz, CDCl$_3$)

δ=1.91 ppm (m$_c$, 2 H, —CH$_2$CH$_2$CH$_2$—), 2.74 (t, J=7.5 Hz, 2H, Ar—CH$_2$—), 3.69 (m$_c$, 2 H, —CH$_2$—OH), 5.18 (s, 1H, OH), 7.12 (m$_c$, 2 H, Ar—H), 7.20 (AB-d, J=8.2 Hz, 2H, Ar—H), 7.49 (AB-d, J=8.2 Hz, 2H, Ar—H), 7.53 (dd, J=8.5 Hz, J=1.6 Hz, 1H, Ar—H), 7.64 (d, J=8.5 Hz, 1H, Ar—H), 7.73 (d, J=8.7 Hz, 1H, Ar—H), 7.97 (d, br., J=0.8 Hz, 1H, Ar—H).

2.5 6-{4-[3-(2-Methylacryloyloxy)propyl]phenylethynyl}naphthalen-2-yl 2-methacrylate

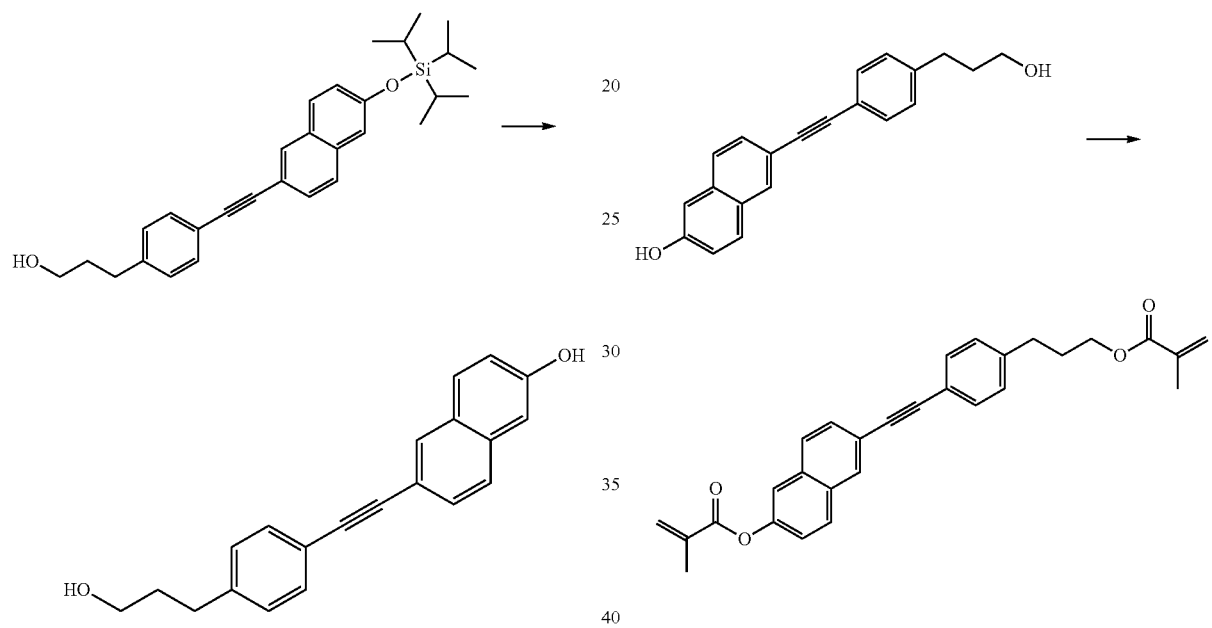

8.0 g (17.4 mmol) of 3-[4-(6-triisopropylsilanyloxynaphthalen-2-ylethynyl)-phenyl]propan-1-ol are dissolved in 100 ml of THF, and 22 ml (22 mmol) of a 1 M solution of tetrabutylammonium fluoride in THF are added with ice-cooling. After 30 min, the cooling is removed, and the batch is left to stir for 1 h at room temp. The batch is added to water, acidified using dil. hydrochloric acid and extracted three times with ethyl acetate. The combined org. phases are dried over sodium sulfate, the solvent is removed in vacuo, and the residue is chromatographed on silica gel with toluene/ethyl acetate/ethanol (60:39:1). Crystallisation of the crude prod- An analogous procedure to Example 1 starting from 6-[4-(3-hydroxypropyl)phenylethynyl]naphthalen-2-ol gives 6-{4-[3-(2-methylacryloyloxy)-propyl]phenylethynyl}naphthalen-2-yl 2-methacrylate as colourless crystals of m.p. 85° C.

EXAMPLE 3

4'-{4-[3-(2-Methylacryloyloxy)propyl]phenylethynyl}biphenyl-4-yl 2-methacrylate

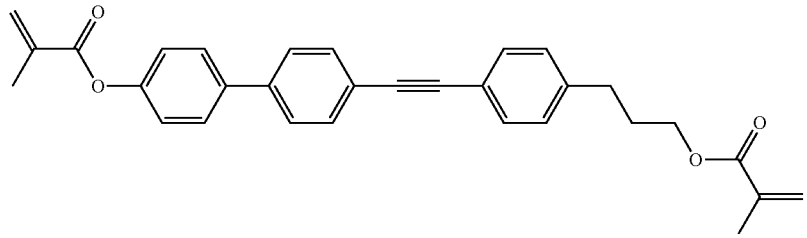 [SMILES: C=C(C)C(=O)OCCCc1ccc(C#Cc2ccc(-c3ccc(OC(=O)C(=C)C)cc3)cc2)cc1]

An analogous procedure to the synthesis process described in Example 2 starting from 4-bromobiphenyl-4-ol gives 4'-{4-[3-(2-methylacryloyloxy)-propyl]phenylethynyl}biphenyl-4-yl 2-methacrylate as colourless crystals of m.p. 123° C.

USE EXAMPLE 1

Nematic LC mixture N1 is formulated as follows:

| | | | |
|---|---|---|---|
| CCH-501 | 9.00% | cl.p. | +70.0 |
| CCH-35 | 14.00% | Δn | 0.0825 |
| PCH-53 | 8.00% | Δε | −3.5 |
| CY-3-O4 | 14.00% | $\epsilon_\parallel$ | 3.5 |
| CY-5-O4 | 13.00% | $K_3/K_1$ | 1.00 |
| CCY-3-O2 | 8.00% | γ | 141 |
| CCY-5-O2 | 8.00% | $V_0$ | 2.06 |
| CCY-2-1 | 9.00% | | |
| CCY-3-1 | 9.00% | | |
| CPY-2-O2 | 8.00% | | |

0.3% of a polymerisable monomeric compound from the examples shown below is added to LC mixture $N^1$, and the resultant mixtures are introduced into VA-e/o test cells (rubbed antiparallel, VA polyimide alignment layer, layer thickness d≈4 μm). The cells are irradiated with UV light having an intensity of 50 mW/cm² for the time indicated with application of a voltage of 24 V (alternating current), causing polymerisation of the monomeric compound. The tilt angle is determined before and after the UV irradiation by a rotational crystal experiment (Autronic-Melchers TBA-105).

In order to determine the polymerisation rate, the residual content of unpolymerised RM (in % by weight) in the test cells is measured after various exposure times using the HPLC method. To this end, each mixture is polymerised in the test cell under the conditions indicated. The mixture is then rinsed out of the test cell using methyl ethyl ketone and measured.

Example 1

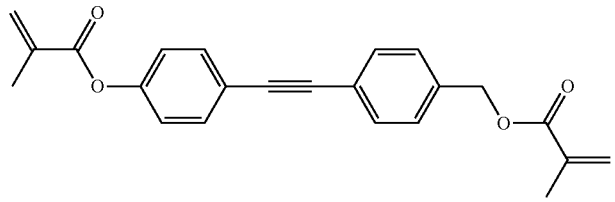

Example 2

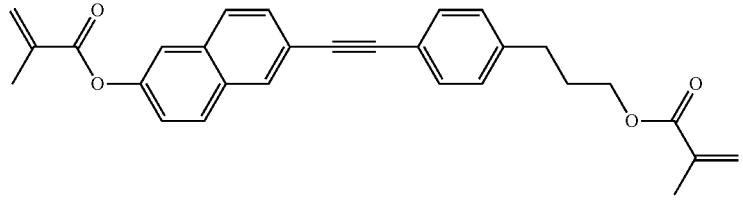

Example 3

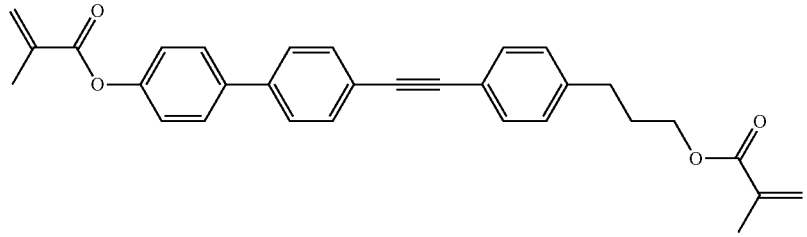

The tilt-angle results and the RM concentrations after various exposure times are shown in Table 1.

TABLE 1

| | | | | | |
|---|---|---|---|---|---|
| | (t = exposure time) | | | | |
| | Ex. 1 | Ex. 2 | Ex. 3 | Ex. 1 | Ex. 2 |
| t/s | Tilt angle/° | | | Residual RM/% | |
| 0 | 88.5 | 87.8 | 88.4 | 0.300 | 0.300 |
| 30 | 88.8 | 83.3 | 85.1 | — | — |
| 60 | 86.7 | 67.7 | 82.8 | — | — |
| 120 | 81.0 | 35.6 | 78.6 | 0.131 | 0.000 |
| 240 | 68.9 | 25.0 | 75.2 | 0.030 | 0.000 |
| 360 | 55.4 | 21.8 | 72.5 | 0.013 | 0.000 |

As can be seen from Table 1, a small tilt angle after polymerisation and a very fast polymerisation rate can be achieved very quickly with the monomers according to the invention from Examples 1, 2 and 3.

The invention claimed is:

1. A liquid crystal medium comprising:
   a polymerizable component A) comprising one or more polymerizable compounds; and
   a liquid-crystalline component B) comprising one or more low-molecular-weight compounds;
   wherein component A) comprises one or more polymerizable compounds of formula I P-(Sp)$_{s1}$-A$^1$-Z$^1$-A$^2$(-Z$^2$-A$^3$)$_m$-(Sp)$_{s2}$-P    I wherein:
   P on each occurrence, identically or differently, denotes a polymerizable group,
   Sp on each occurrence, identically or differently, denotes a spacer group,
   s1, s2 each, independently of one another, denote 0 or 1, wherein one of s1 and s2 is 0 and the other is 1,
   A$^1$, A$^2$, A$^3$ each, independently of one another, denote a 1,4-phenylene, naphthalene-1,4-diyl or naphthalene-2,6-diyl group, where, in addition, one or more CH groups in these groups may be replaced by N, phenanthrene-2,7-diyl, anthracene-2,7-diyl, 9,10-dihydrophenanthrene-2,7-diyl, 9H-fluorene-2,7-diyl, 9,9-dimethylfluorene-2,7-diyl or dibenzofuran-3,7-diyl, and where each of these groups may be unsubstituted or mono- or polysubstituted by L,
   m denotes 0, 1 or 2,
   L on each occurrence, identically or differently, denotes P—, P-Sp-, OH, CH$_2$OH, halogen, —CN, —NO$_2$, —NCO, —NCS, —OCN, —SCN, —C(=O)N(R$^x$)$_2$, —C(=O)Y$^1$, —C(=O)R$^x$, —N(R$^x$)$_2$, optionally substituted silyl or an optionally substituted carbon group or hydrocarbon group,
   R$^x$ denotes P—, P-Sp-, H, halogen, straight-chain, branched or cyclic alkyl having 1 to 25 C atoms, in which, in addition, one or more non-adjacent CH$_2$ groups may be replaced by —O—, —S—, —CO—, —CO—O—, —O—CO—, —O—CO—O— in such a way that O and/or S atoms are not linked directly to one another, and in which, in addition, one or more H atoms may be replaced by F, Cl, P— or P-Sp-,
   Y$^1$ denotes halogen,
   Z$^1$, Z$^2$ each, independently of one another, denote —CO—O—, —OCO—, —CY=CY—, —C≡C— or a single bond, where at least one of the radicals Z$^1$ and Z$^2$ denotes —C≡C—, and
   Y on each occurrence, identically or differently, denotes H or F; and wherein component B) comprises one or more compounds selected from formulae CY and PY:

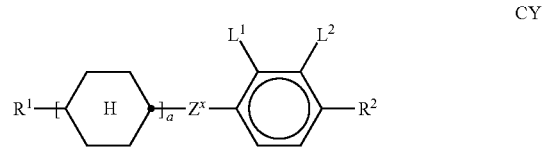

CY

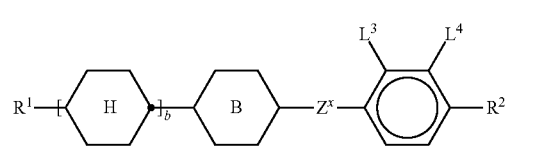

PY wherein:
   a denotes 1 or 2,
   b denotes 0 or 1,

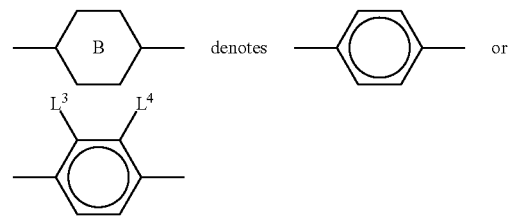

R$^1$ and R$^2$ each, independently of one another, denote alkyl having 1 to 12 C atoms, where, in addition, one or two non-adjacent CH$_2$ groups may be replaced by —O—, —CH=CH—, —CO—, —O—CO— or —CO—O— in such a way that O atoms are not linked directly to one another,
   Z$^x$ denotes —CH=CH—, —CH$_2$O—, —OCH$_2$—, —CF$_2$O—, —OCF$_2$—, —O—, —CH$_2$—, —CH$_2$CH$_2$— or a single bond, and
   L$^{1-4}$ each, independently of one another, denote F, Cl, OCF$_3$, CF$_3$, CH$_3$, CH$_2$F, or CHF$_2$; and
   wherein the proportion of polymerizable compounds of formula I in said medium is 0.05 to 5%.

2. A liquid crystal medium according to claim 1, wherein A$^1$ and A$^2$ each, independently of one another, denote 1,4-phenylene, naphthalene-2,6-diyl, phenanthrene-2,7-diyl or anthracene-2,7-diyl, where all these groups may be unsubstituted or mono- or polysubstituted by L, and L denotes P-Sp-, OH, CH$_2$OH, F, Cl, Br, I, —CN, —NO$_2$, —NCO, —NCS, —OCN, —SCN, —C(=O)N(R$^x$)$_2$, —C(=O)Y$^1$, —C(=O)R$^x$, —N(R$^x$)$_2$, optionally substituted silyl, optionally substituted aryl having 6 to 20 C atoms, straight-chain or branched alkyl or alkoxy having 1 to 25 C atoms, or straight-chain or branched alkenyl, alkynyl, alkylcarbonyl, alkoxycarbonyl, alkylcarbonyloxy or alkoxycarbonyloxy having 2 to 25 C atoms, in which, in addition, one or more H atoms in all these groups may be replaced by F, Cl, P— or P-Sp-.

3. A PS or PSA liquid crystal display comprising a liquid crystal cell having two substrates and two electrodes, where at least one substrate is transparent to light and at least one substrate has one or two electrodes, and a layer, located between the substrates, of a liquid crystal medium comprising a polymerized component, where the liquid crystal medium is obtained by polymerization of a liquid crystal medium comprising:
  a polymerizable component A) comprising one or more polymerizable compounds; and
  a liquid-crystalline component B) comprising one or more low-molecular-weight compounds;
wherein component A) comprises one or more polymerizable compounds of formula I $$P\text{-}(Sp)_{s1}\text{-}A^1\text{-}Z^1\text{-}A^2(\text{-}Z^2\text{-}A^3)_m\text{-}(Sp)_{s2}\text{-}P \qquad I$$

wherein:
  P on each occurrence, identically or differently, denotes a polymerizable group,
  Sp on each occurrence, identically or differently, denotes a spacer group,
  s1, s2 each, independently of one another, denote 0 or 1, wherein one of s1 and s2 is 0 and the other is 1,
  $A^1$, $A^2$, $A^3$ each, independently of one another, denote a 1,4-phenylene, naphthalene-1,4-diyl or naphthalene-2,6-diyl group, where, in addition, one or more CH groups in these groups may be replaced by N, phenanthrene-2,7-diyl, anthracene-2,7-diyl, 9,10-dihydrophenanthrene-2,7-diyl, 9H-fluorene-2,7-diyl, 9,9-dimethylfluorene-2,7-diyl or dibenzofuran-3,7-diyl, and where each of these groups may be unsubstituted or mono- or polysubstituted by L,
  m denotes 0, 1 or 2,
  L on each occurrence, identically or differently, denotes P—, P-Sp-, OH, $CH_2OH$, halogen, —CN, —$NO_2$, —NCO, —NCS, —OCN, —SCN, —C(=O)N($R^x$)$_2$, —C(=O)$Y^1$, —C(=O)$R^x$, —N($R^x$)$_2$, optionally substituted silyl or an optionally substituted carbon group or hydrocarbon group,
  $R^x$ denotes P—, P-Sp-, H, halogen, straight-chain, branched or cyclic alkyl having 1 to 25 C atoms, in which, in addition, one or more non-adjacent $CH_2$ groups may be replaced by —O—, —S—, —CO—, —CO—O—, —O—CO—, —O—CO—O— in such a way that O and/or S atoms are not linked directly to one another, and in which, in addition, one or more H atoms may be replaced by F, Cl, P— or P-Sp-,
  $Y^1$ denotes halogen,
  $Z^1$, $Z^2$ each, independently of one another, denote —CO—O—, —OCO—, —CY=CY—, —C≡C— or a single bond, where at least one of the radicals $Z^1$ and $Z^2$ denotes —C≡C—, and
  Y on each occurrence, identically or differently, denotes H or F; and
wherein component B) comprises one or more compounds selected from formulae CY and PY:

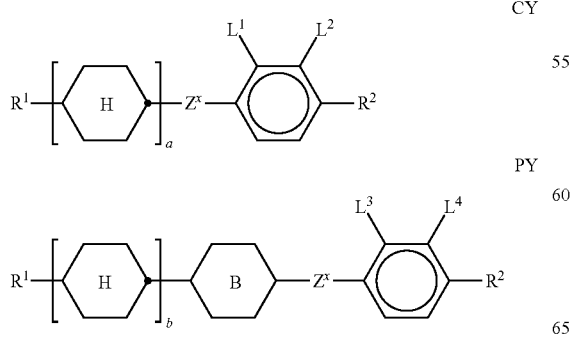

wherein:
  a denotes 1 or 2,
  b denotes 0 or 1,

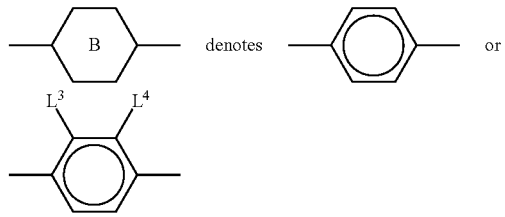

$R^1$ and $R^2$ each, independently of one another, denote alkyl having 1 to 12 C atoms, where, in addition, one or two non-adjacent $CH_2$ groups may be replaced by —O—, —CH=CH—, —CO—, —O—CO— or —CO—O— in such a way that O atoms are not linked directly to one another,
  $Z^x$ denotes —CH=CH—, —$CH_2O$—, —$OCH_2$—, —$CF_2O$—, —$OCF_2$—, —O—, —$CH_2$—, —$CH_2CH_2$— or a single bond, and
  $L^{1-4}$ each, independently of one another, denote F, Cl, $OCF_3$, $CF_3$, $CH_3$, $CH_2F$, or $CHF_2$; and
wherein during said polymerization one or more polymerizable compounds of component A) between the substrates of the liquid crystal cell polymerizes to form said polymerized component.

4. A liquid crystal medium comprising:
  a polymerizable component A) comprising one or more polymerizable compounds; and
  a liquid-crystalline component B) comprising one or more low-molecular-weight compounds;
wherein component A) comprises one or more polymerizable compounds of formula I $$P\text{-}(Sp)_{s1}\text{-}A^1\text{-}Z^1\text{-}A^2(\text{-}Z^2\text{-}A^3)_m\text{-}(Sp)_{s2}\text{-}P \qquad I$$

wherein:
  P on each occurrence, identically or differently, denotes a polymerizable group,
  Sp on each occurrence, identically or differently, denotes a spacer group,
  s1, s2 each, independently of one another, denote 0 or 1, wherein one of s1 and s2 is 0 and the other is 1,
  $A^1$, $A^2$, $A^3$ each, independently of one another, denote a 1,4-phenylene, naphthalene-1,4-diyl or naphthalene-2,6-diyl group, where, in addition, one or more CH groups in these groups may be replaced by N, phenanthrene-2,7-diyl, anthracene-2,7-diyl, 9,10-dihydrophenanthrene-2,7-diyl, 9H-fluorene-2,7-diyl, 9,9-dimethylfluorene-2,7-diyl or dibenzofuran-3,7-diyl, and where each of these groups may be unsubstituted or mono- or polysubstituted by L,
  m denotes 0, 1 or 2,
  L on each occurrence, identically or differently, denotes P—, P-Sp-, OH, $CH_2OH$, halogen, —CN, —$NO_2$, —NCO, —NCS, —OCN, —SCN, —C(=O)N($R^x$)$_2$, —C(=O)$Y^1$, —C(=O)$R^x$, —N($R^x$)$_2$, optionally substituted silyl or an optionally substituted carbon group or hydrocarbon group,
  $R^x$ denotes P—, P-Sp-, H, halogen, straight-chain, branched or cyclic alkyl having 1 to 25 C atoms, in which, in addition, one or more non-adjacent $CH_2$ groups may be replaced by —O—, —S—, —CO—, —CO—O—, —O—CO—, —O—CO—O— in such a way that O and/or S atoms are not linked directly to one another, and in which, in addition, one or more H atoms may be replaced by F, Cl, P— or P-Sp-, $Y^1$ denotes halogen, $Z^1$, $Z^2$ each, independently of one another, denote —CO—O—, —OCO—, —CY=CY—, —C≡C— or a single bond, where at least one of the radicals $Z^1$ and $Z^2$ denotes —C≡C—, and Y on each occurrence, identically or differently, denotes H or F; and wherein component B) comprises one or more compounds selected from formulae CY and PY:

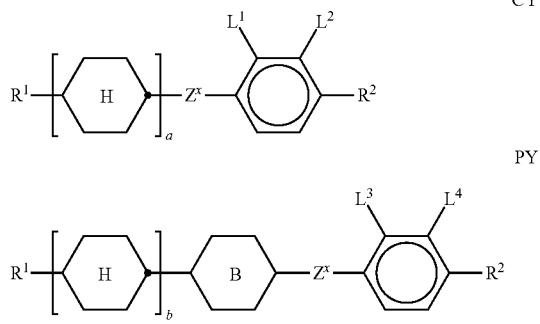

wherein:

a denotes 1 or 2, b denotes 0 or 1,

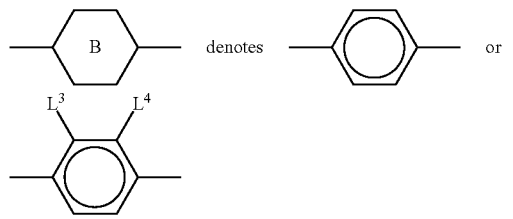

$R^1$ and $R^2$ each, independently of one another, denote alkyl having 1 to 12 C atoms, where, in addition, one or two non-adjacent CH$_2$ groups may be replaced by —O—, —CH=CH—, —CO—, —O—CO— or —CO—O— in such a way that O atoms are not linked directly to one another, $Z^x$ denotes —CH=CH—, —CH$_2$O—, —OCH$_2$—, —CF$_2$O—, —OCF$_2$—, —O—, —CH$_2$—, —CH$_2$CH$_2$— or a single bond, and $L^{1-4}$ each, independently of one another, denote F, Cl, OCF$_3$, CF$_3$, CH$_3$, CH$_2$F, or CHF$_2$; and wherein component B) further comprises one or more compounds of the following formula:

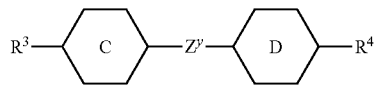

wherein:

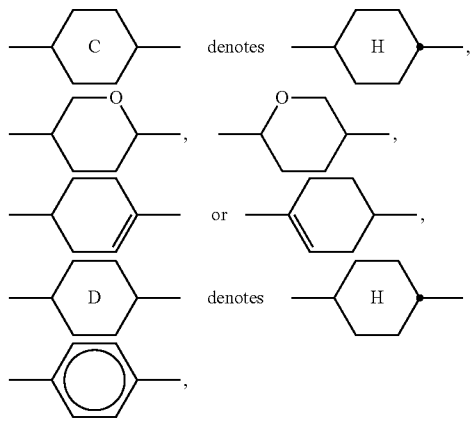

$R^3$ and $R^4$ each, independently of one another, denote alkyl having 1 to 12 C atoms, in which, in addition, one or two non-adjacent CH$_2$ groups may be replaced by —O—, —CH=CH—, —CO—, —O—CO— or —CO—O— in such a way that O atoms are not linked directly to one another, $Z^y$ denotes —CH$_2$CH$_2$—, —CH=CH—, —CF$_2$O—, —OCF$_2$—, —CH$_2$O—, —OCH$_2$—, —COO—, —OCO—, —C$_2$F$_4$—, —CF=CF— or a single bond.

5. A liquid crystal display comprising a medium according to claim 1.

6. A liquid crystal display comprising a liquid crystal medium,
wherein said display is a PSA-VA, PSA-OCB, PSA-IPS, PSA-FFS, PSA-positive-VA or PSA-TN display, and wherein said medium comprises:
a polymerizable component A) comprising one or more polymerizable compounds; and
a liquid-crystalline component B) comprising one or more low-molecular-weight compounds;

wherein component A) comprises one or more polymerizable compounds of formula I $$P-(Sp)_{s1}-A^1-Z^1-A^2(-Z^2-A^3)_m-(Sp)_{s2}-P \qquad I$$

wherein:

P on each occurrence, identically or differently, denotes a polymerizable group, Sp on each occurrence, identically or differently, denotes a spacer group, s1, s2 each, independently of one another, denote 0 or 1, wherein one of s1 and s2 is 0 and the other is 1, $A^1$, $A^2$, $A^3$ each, independently of one another, denote a 1,4-phenylene, naphthalene-1,4-diyl or naphthalene-2,6-diyl group, where, in addition, one or more CH groups in these groups may be replaced by N, phenanthrene-2,7-diyl, anthracene-2,7-diyl, 9,10-dihydrophenanthrene-2,7-diyl, 9H-fluorene-2,7-diyl, 9,9-dimethylfluorene-2,7-diyl or dibenzofuran-3,7-diyl, and where each of these groups may be unsubstituted or mono- or polysubstituted by L, m denotes 0, 1 or 2, L on each occurrence, identically or differently, denotes P—, P-Sp-, OH, CH$_2$OH, halogen, —CN, —NO$_2$, —NCO, —NCS, —OCN, —SCN, —C(=O)N(R$^x$)$_2$, —C(=O)Y$^1$, —C(=O)R$^x$, —N(R$^x$)$_2$, optionally substituted silyl or an optionally substituted carbon group or hydrocarbon group, R$^x$ denotes P—, P-Sp-, H, halogen, straight-chain, branched or cyclic alkyl having 1 to 25 C atoms, in which, in addition, one or more non-adjacent CH$_2$ groups may be replaced by —O—, —S—, —CO—, —CO—O—, —O—CO—, —O—CO—O— in such a way that O and/or S atoms are not linked directly to one another, and in which, in addition, one or more H atoms may be replaced by F, Cl, P— or P-Sp-, Y$^1$ denotes halogen, Z$^1$, Z$^2$ each, independently of one another, denote —CO—O—, —OCO—, —CY=CY—, —C≡C— or a single bond, where at least one of the radicals Z$^1$ and Z$^2$ denotes —C≡C—, and Y on each occurrence, identically or differently, denotes H or F; and wherein component B) comprises one or more compounds selected from formulae CY and PY:

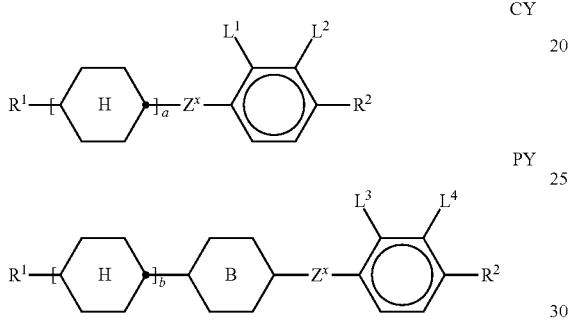

wherein:
a denotes 1 or 2,
b denotes 0 or 1,

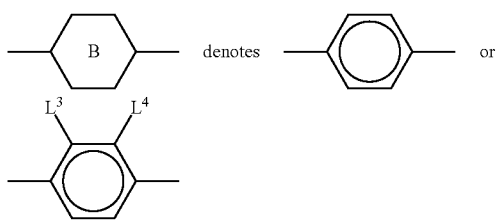

R$^1$ and R$^2$ each, independently of one another, denote alkyl having 1 to 12 C atoms, where, in addition, one or two non-adjacent CH$_2$ groups may be replaced by —O—, —CH=CH—, —CO—, —O—CO— or —CO—O— in such a way that O atoms are not linked directly to one another, Z$^x$ denotes —CH=CH—, —CH$_2$O—, —OCH$_2$—, —CF$_2$O—, —OCF$_2$—, —O—, —CH$_2$—, —CH$_2$CH$_2$— or a single bond, and L$^{1-4}$ each, independently of one another, denote F, Cl, OCF$_3$, CF$_3$, CH$_3$, CH$_2$F, or CHF$_2$.

7. A process for the production of a PS or PSA liquid crystal, said process comprising introducing a liquid crystal medium into a liquid crystal cell having two substrates and two electrodes, where at least one substrate is transparent to light and at least one substrate has one or two electrodes, wherein said medium comprises:
  a polymerizable component A) comprising one or more polymerizable compounds; and
  a liquid-crystalline component B) comprising one or more low-molecular-weight compounds;

wherein component A) comprises one or more polymerizable compounds of formula I

P-(Sp)$_{s1}$-A$^1$-Z$^1$-A$^2$(-Z$^2$-A$^3$)$_m$-(Sp)$_{s2}$-P   I wherein:
P on each occurrence, identically or differently, denotes a polymerizable group,
Sp on each occurrence, identically or differently, denotes a spacer group,
s1, s2 each, independently of one another, denote 0 or 1, wherein one of s1 and s2 is 0 and the other is 1,
A$^1$, A$^2$, A$^3$ each, independently of one another, denote a 1,4-phenylene, naphthalene-1,4-diyl or naphthalene-2,6-diyl group, where, in addition, one or more CH groups in these groups may be replaced by N, phenanthrene-2,7-diyl, anthracene-2,7-diyl, 9,10-dihydrophenanthrene-2,7-diyl, 9H-fluorene-2,7-diyl, 9,9-dimethylfluorene-2,7-diyl or dibenzofuran-3,7-diyl, and where each of these groups may be unsubstituted or mono- or polysubstituted by L,
m denotes 0, 1 or 2,
L on each occurrence, identically or differently, denotes P—, P-Sp-, OH, CH$_2$OH, halogen, —CN, —NO$_2$, —NCO, —NCS, —OCN, —SCN, —C(=O)N(R$^x$)$_2$, —C(=O)Y$^1$, —C(=O)R$^x$, —N(R$^x$)$_2$, optionally substituted silyl or an optionally substituted carbon group or hydrocarbon group,
R$^x$ denotes P—, P-Sp-, H, halogen, straight-chain, branched or cyclic alkyl having 1 to 25 C atoms, in which, in addition, one or more non-adjacent CH$_2$ groups may be replaced by —O—, —S—, —CO—, —CO—O—, —O—CO—, —O—CO—O— in such a way that O and/or S atoms are not linked directly to one another, and in which, in addition, one or more H atoms may be replaced by F, Cl, P— or P-Sp-,
Y$^1$ denotes halogen,
Z$^1$, Z$^2$ each, independently of one another, denote —CO—O—, —OCO—, —CY=CY—, —C≡C— or a single bond, where at least one of the radicals Z$^1$ and Z$^2$ denotes —C≡C—, and
Y on each occurrence, identically or differently, denotes H or F; and
wherein component B) comprises one or more compounds selected from formulae CY and PY:

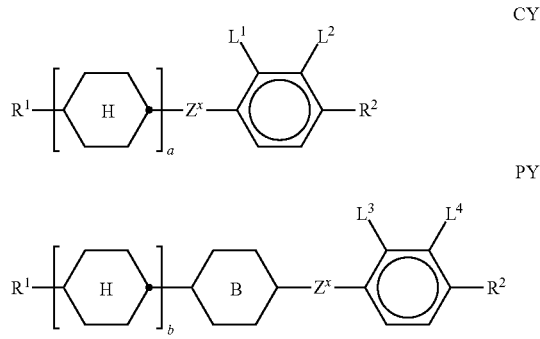

wherein:
a denotes 1 or 2,
b denotes 0 or 1,

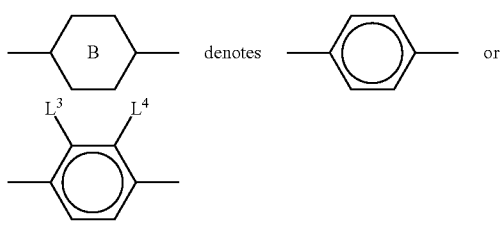

$R^1$ and $R^2$ each, independently of one another, denote alkyl having 1 to 12 C atoms, where, in addition, one or two non-adjacent $CH_2$ groups may be replaced by —O—, —CH=CH—, —CO—, —O—CO— or —CO—O— in such a way that O atoms are not linked directly to one another, $Z^x$ denotes —CH=CH—, —$CH_2$O—, —O$CH_2$—, —$CF_2$O—, —OC$F_2$—, —O—, —$CH_2$—, —$CH_2CH_2$— or a single bond, and $L^{1-4}$ each, independently of one another, denote F, Cl, OC$F_3$, C$F_3$, C$H_3$, C$H_2$F, or CH$F_2$; and polymerizing said one or more polymerizable compounds of component A).

8. A liquid crystal medium comprising:
a polymerizable component A) comprising one or more polymerizable compounds; and
a liquid-crystalline component B) comprising one or more low-molecular-weight compounds;
wherein component A) comprises one or more polymerizable compounds of formula I $$P\text{-}(Sp)_{s1}\text{-}A^1\text{-}Z^1\text{-}A^2(\text{-}Z^2\text{-}A^3)_m\text{-}(Sp)_{s2}\text{-}P \quad \text{I}$$

wherein:
P on each occurrence, identically or differently, denotes a polymerizable group,
Sp on each occurrence, identically or differently, denotes a spacer group,
s1, s2 each, independently of one another, denote 0 or 1, wherein one of s1 and s2 is 0 and the other is 1,
$A^1$, $A^2$, $A^3$ each, independently of one another, denote a 1,4-phenylene, naphthalene-1,4-diyl or naphthalene-2,6-diyl group, where, in addition, one or more CH groups in these groups may be replaced by N, phenanthrene-2,7-diyl, anthracene-2,7-diyl, 9,10-dihydrophenanthrene-2,7-diyl, 9H-fluorene-2,7-diyl, 9,9-dimethylfluorene-2,7-diyl or dibenzofuran-3,7-diyl, and where each of these groups may be unsubstituted or mono- or polysubstituted by L,
m denotes 0, 1 or 2,
L on each occurrence, identically or differently, denotes P—, P-Sp-, OH, CH$_2$OH, halogen, —CN, —NO$_2$, —NCO, —NCS, —OCN, —SCN, —C(=O)N(R$^x$)$_2$, —C(=O)Y$^1$, —C(=O)R$^x$, —N(R$^x$)$_2$, optionally substituted silyl or an optionally substituted carbon group or hydrocarbon group,
$R^x$ denotes P—, P-Sp-, H, halogen, straight-chain, branched or cyclic alkyl having 1 to 25 C atoms, in which, in addition, one or more non-adjacent CH$_2$ groups may be replaced by —O—, —S—, —CO—, —CO—O—, —O—CO—, —O—CO—O— in such a way that O and/or S atoms are not linked directly to one another, and in which, in addition, one or more H atoms may be replaced by F, Cl, P— or P-Sp-,
$Y^1$ denotes halogen, $Z^1$, $Z^2$ each, independently of one another, denote —CO—O—, —OCO—, —CY=CY—, —C≡C— or a single bond, where at least one of the radicals $Z^1$ and $Z^2$ denotes —C≡C—, and
Y on each occurrence, identically or differently, denotes H or F; and
wherein component B) comprises one or more compounds selected from formulae CY and PY:

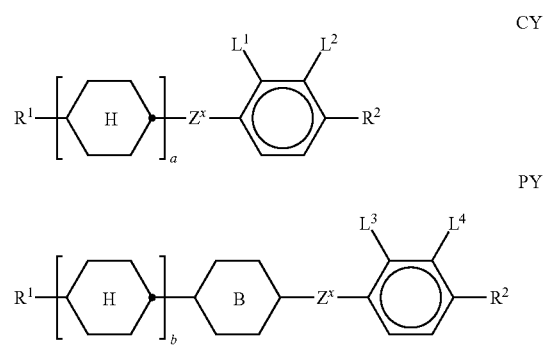

wherein:
a denotes 1 or 2,
b denotes 0 or 1,

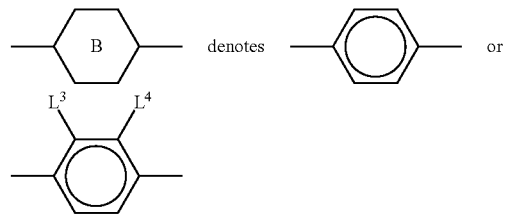

$R^1$ and $R^2$ each, independently of one another, denote alkyl having 1 to 12 C atoms, where, in addition, one or two non-adjacent CH$_2$ groups may be replaced by —O—, —CH=CH—, —CO—, —O—CO— or —CO—O— in such a way that O atoms are not linked directly to one another, $Z^x$ denotes —CH=CH—, —CH$_2$O—, —OCH$_2$—, —CF$_2$O—, —OCF$_2$—, —O—, —CH$_2$—, —CH$_2$CH$_2$— or a single bond, and $L^{1-4}$ each, independently of one another, denote F, Cl, OCF$_3$, CF$_3$, CH$_3$, CH$_2$F, or CHF$_2$;

wherein the proportion of component A) in said medium is <5%.

9. The PS or PSA liquid crystal display according to claim 3, wherein said polymerization is performed by application of an electrical voltage to the electrodes.

10. A liquid crystal medium according to claim 1, wherein $Z^x$ denotes a single bond and/or $Z^y$ denotes a single bond.

11. The process according to claim 7, wherein said polymerization of said polymerizable compounds is performed by application of an electrical voltage to the electrodes.

12. A liquid crystal medium according to claim 1, wherein P, on each occurrence, is selected from CH$_2$=CW$^1$—CO—O—, CH$_2$=CH—O—, (CH$_2$=CH)$_2$CH—O—CO—, (CH$_2$=CH)$_2$CH—O—,

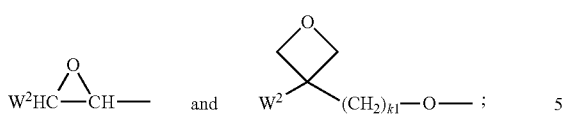

W¹ is H, F, Cl, CN, CF₃, phenyl or alkyl having 1 to 5 C atoms;

W² and W³ each, independently of one another, are H or alkyl having 1 to 5 C atoms;

k₁ is 0 or 1;

Sp is Sp"-X";

Sp" is —(CH₂)$_{p1}$—, —(CH₂CH₂O)$_{q1}$—CH₂CH₂—, —CH₂CH₂—S—CH₂CH₂—, —CH₂CH₂—NH—CH₂CH₂— or —(SiR$^{00}$R$^{000}$—O)$_{p1}$—;

p1 is an integer from 1 to 12;

q1 is an integer from 1 to 3;

X" denotes —O—, —S—, —CO—, —CO—O—, —O—CO—, —O—CO—O—, —CO—N(R$^{00}$)—, —N(R$^{00}$)—CO—, —N(R$^{00}$)—CO—N(R$^{00}$)—, —OCH₂—, —CH₂O—, —SCH₂—, —CH₂S—, —CF₂O—, —OCF₂—, —CF₂S—, —SCF₂—, —CF₂CH₂—, —CH₂CF₂—, —CF₂CF₂—, —CH=N—, —N=CH—, —N=N—, —CH=CR⁰—, —CY²=CY³—, —C≡C—, —CH=CH—CO—O—, —O—CO—CH=CH— or a single bond;

R$^{00}$ and R$^{000}$ each, independently of one another, are H or alkyl having 1 to 12 C atoms; and Y² and Y³ each, independently of one another, are H, F, Cl or CN;

A¹, A², A³ each, independently of one another, are 1,4-phenylene, naphthalene-2,6-diyl, phenanthrene-2,7-diyl or anthracene-2,7-diyl, which in each case is unsubstituted or mono- or polysubstituted by L; and L denotes P—, P-Sp-, OH, CH₂OH, F, Cl, Br, I, —CN, —NO₂, —NCO, —NCS, —OCN, —SCN, —C(=O)N(R$^x$)₂, —C(=O)Y¹, —C(=O)R$^x$, —N(R$^x$)₂, optionally substituted silyl, optionally substituted aryl having 6 to 20 C atoms, straight-chain or branched alkyl or alkoxy having 1 to 25 C atoms, or straight-chain or branched alkenyl, alkynyl, alkylcarbonyl, alkoxycarbonyl, alkylcarbonyloxy or alkoxycarbonyloxy having 2 to 25 in which one or more H atoms may be replaced by F, Cl, P— or P-Sp.

13. A liquid crystal medium according to claim 1, wherein the compounds of formula CY are selected from following sub-formulae:

CY1

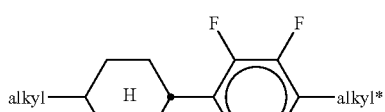

CY2

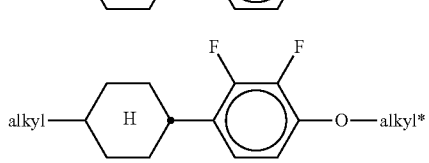

CY3

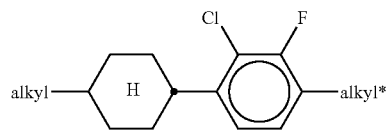

CY4

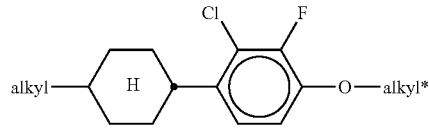

CY5

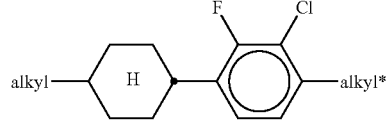

CY6

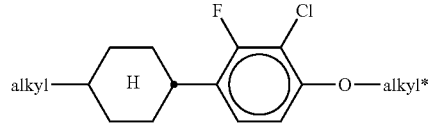

CY7

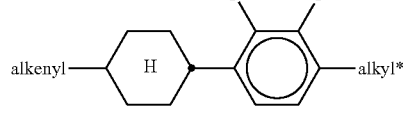

CY8

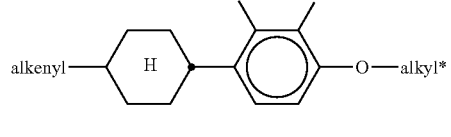

CY9

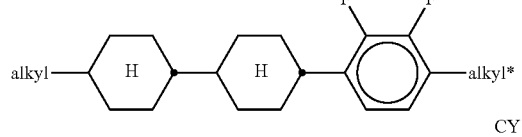

CY10

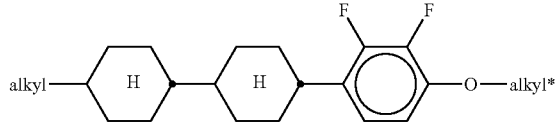

CY11

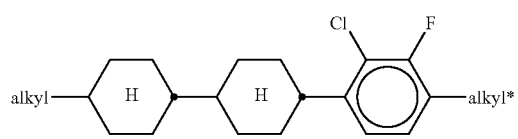

CY12

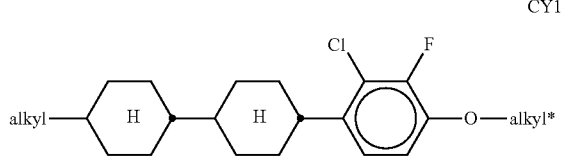

CY13

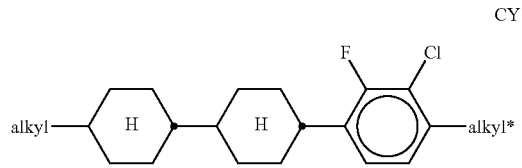

CY14
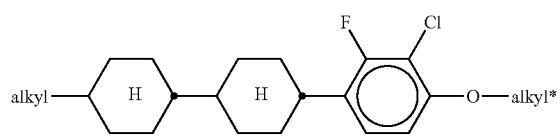
CY15
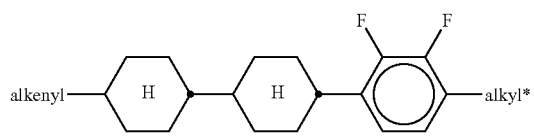
CY16
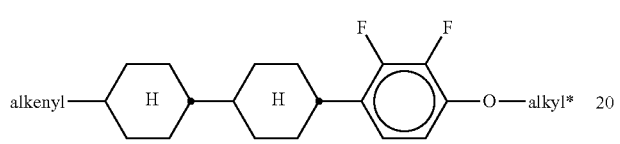
CY17
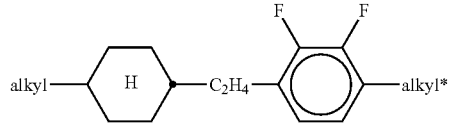
CY18
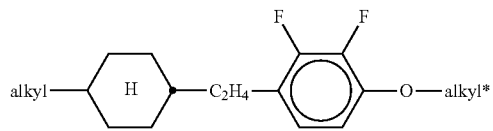
CY19
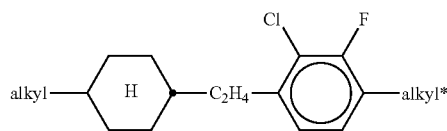
CY20
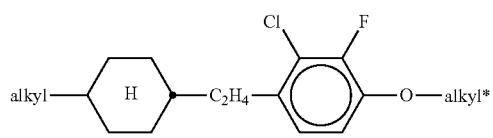
CY21
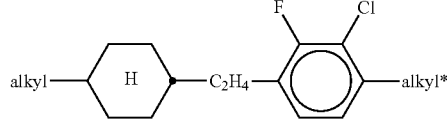
CY22
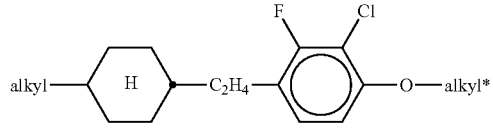
CY23
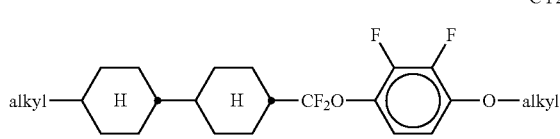
CY24
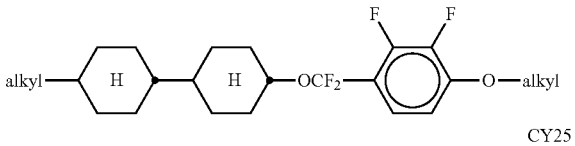
CY25
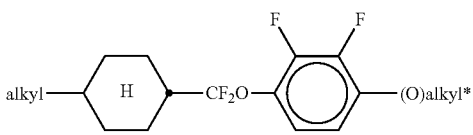
CY25
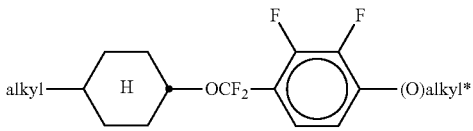
CY26
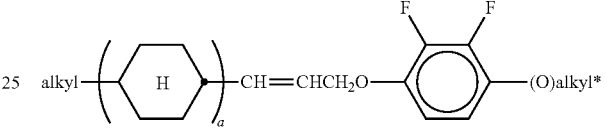
CY27
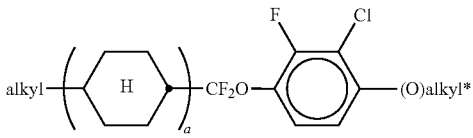
CY28
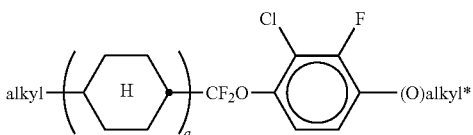
CY29
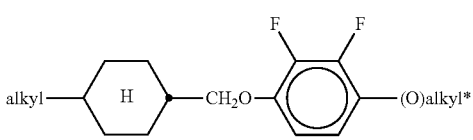
CY30
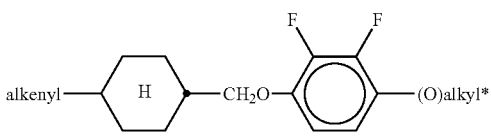
CY31
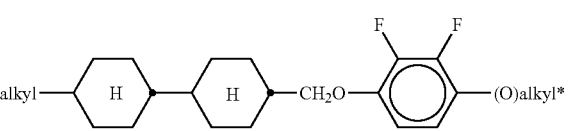
CY32
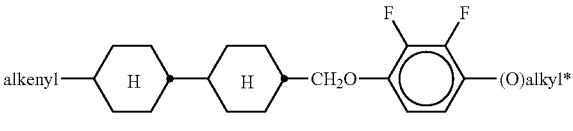

wherein a is 1 or 2, alkyl and alkyl* each, independently of one another, are a straight-chain alkyl radical having 1-6 C atoms, alkenyl denotes a straight-chain alkenyl radical having 2-6 C atoms, and (O) denotes an oxygen atom or a single bond.

14. A liquid crystal medium according to claim 1, wherein the compounds of formula PY are selected from following sub-formulae:

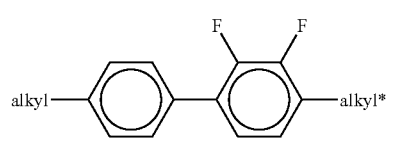
PY1

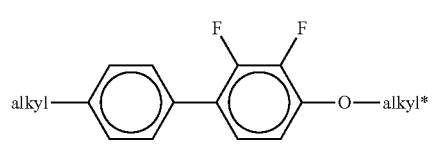
PY2

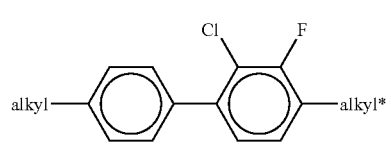
PY3

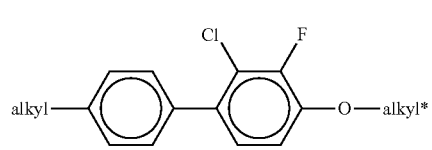
PY4

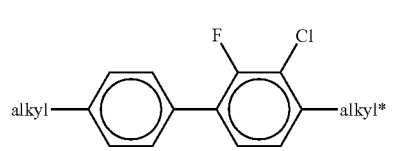
PY5

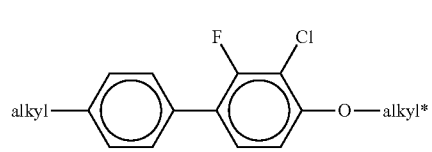
PY6

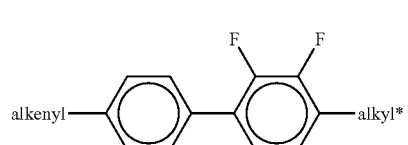
PY7

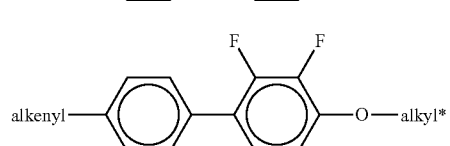
PY8

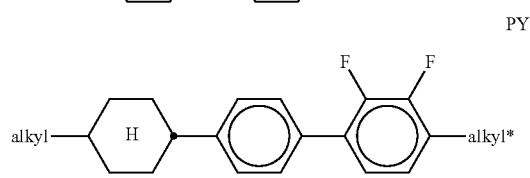
PY9

-continued

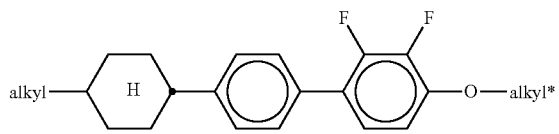
PY10

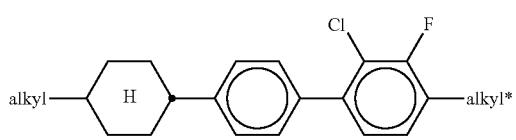
PY11

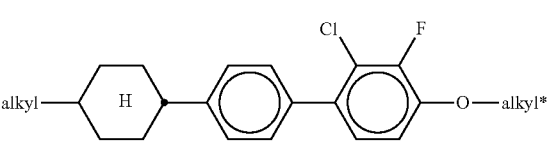
PY12

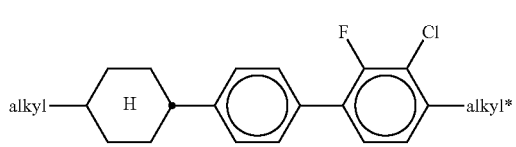
PY13

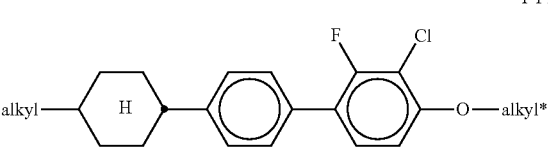
PY14

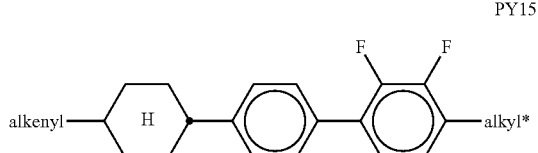
PY15

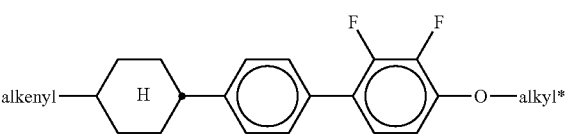
PY16

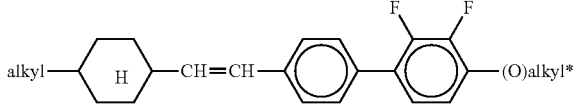
PY17

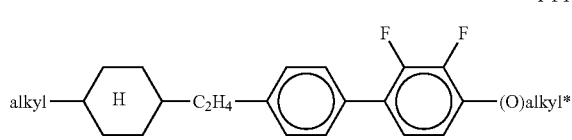
PY18

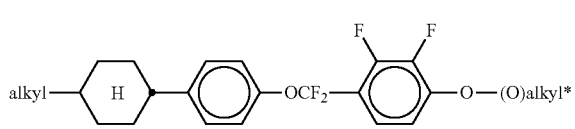
PY19

-continued

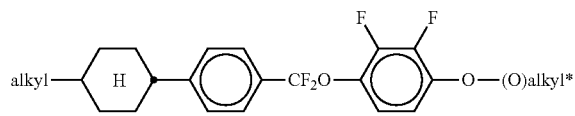
PY20 wherein
- alkyl and alkyl* each, independently of one another, are a straight-chain alkyl radical having 1-6 C atoms,
- alkenyl is a straight-chain alkenyl radical having 2-6 C atoms, and
- (O) denotes an oxygen atom or a single bond.

15. A liquid crystal medium according to claim 13, wherein the compounds of formula PY are selected from following sub-formulae:

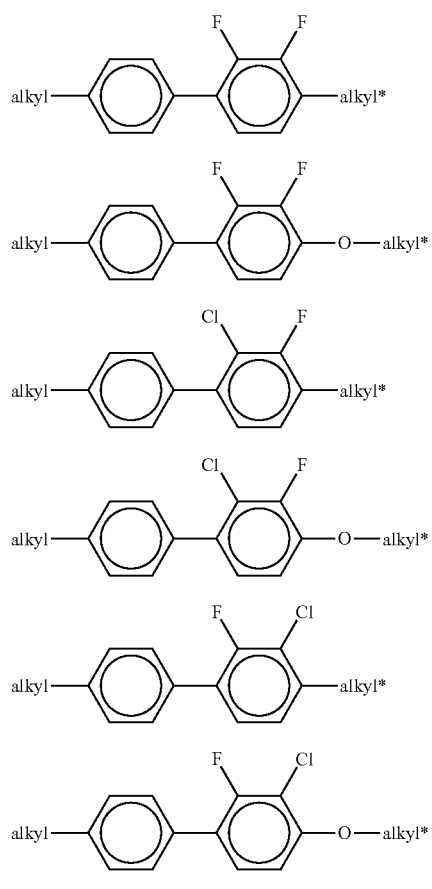

PY1
PY2
PY3
PY4
PY5
PY6
PY7
PY8

-continued

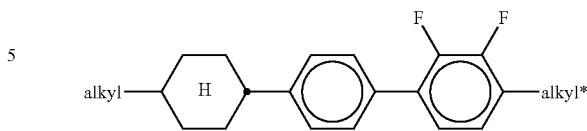
PY9

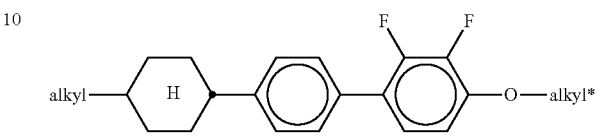
PY10

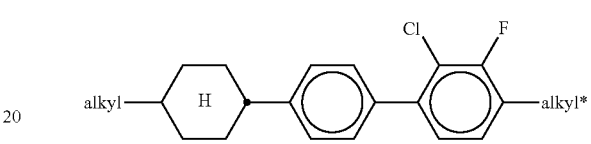
PY11

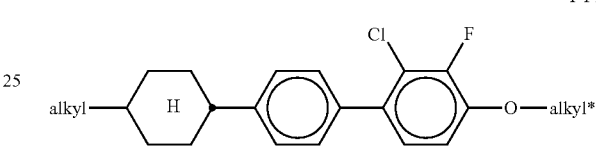
PY12

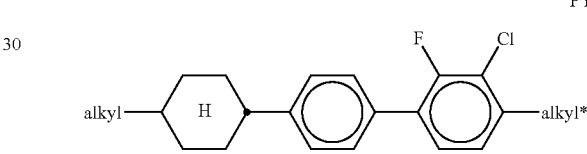
PY13

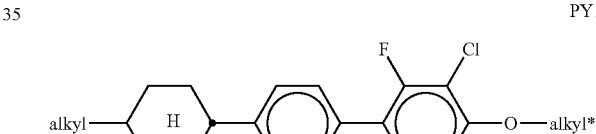
PY14

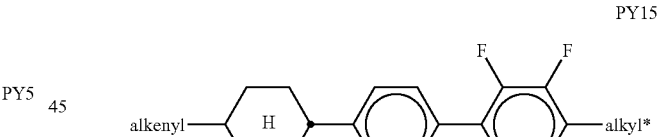
PY15

PY16

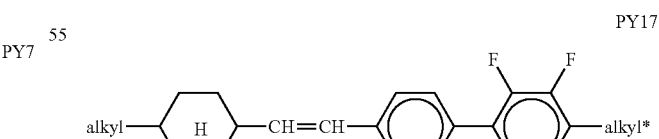
PY17

PY18

PY19

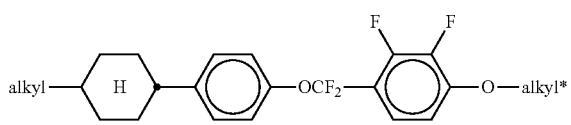

PY20

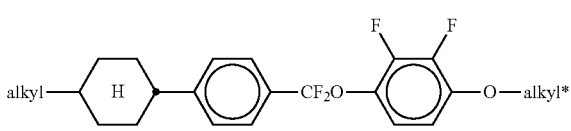

wherein
- alkyl and alkyl* each, independently of one another, are a straight-chain alkyl radical having 1-6 C atoms,
- alkenyl is a straight-chain alkenyl radical having 2-6 C atoms, and
- (O) denotes an oxygen atom or a single bond.

16. A liquid crystal medium according to claim 4, wherein said one or more compounds of formula ZK are selected from the following sub-formulae:

ZY1
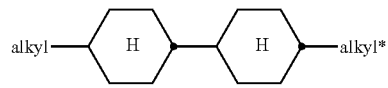

ZY2
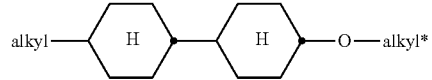

ZY3
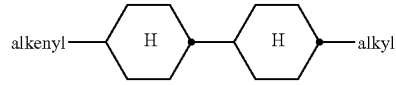

ZY4
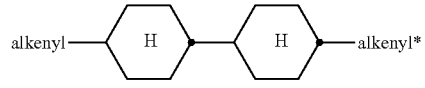

ZY5
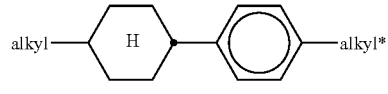

ZY6
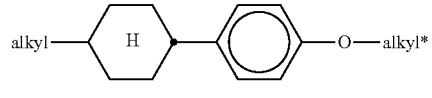

ZY7
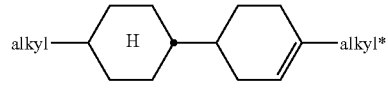

ZY8
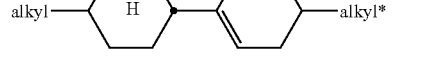

ZY9
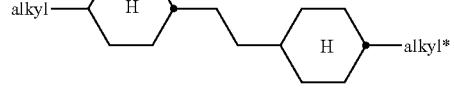

ZY10
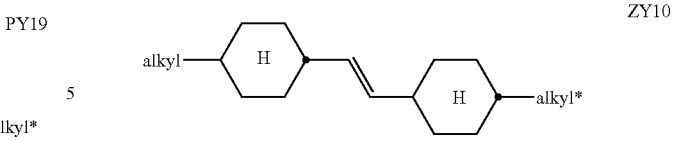

wherein
- alkyl and alkyl* each, independently of one another, are a straight-chain alkyl radical having 1-6 C atoms, and
- alkenyl is a straight-chain alkenyl radical having 2-6 C atoms.

17. A liquid crystal medium according to claim 1, wherein the proportion of polymerizable compounds of formula I is 0.1 to 1%.

18. A liquid crystal medium according to claim 15, wherein said liquid crystal medium contains 1 to 8 compounds of formulae CY1, CY2, PY1 and/or PY2, and the proportion of compounds of formulae CY1, CY2, PY1 and/or PY2 is 5 to 60%.

19. A liquid crystal medium according to claim 15, wherein said liquid crystal medium contains 1 to 8 compounds of formulae CY9, CY10, PY9 and/or PY10, and the proportion of compounds of formulae CY9, CY10, PY9 and/or PY10 is 5 to 60%.

20. A liquid crystal medium according to claim 16, wherein said liquid crystal medium contains 1 to 10 compounds of formulae ZK1, ZK2 and/or ZK6, and the proportion of compounds of formulae ZK1, ZK2 and/or ZK6 is 3 to 25%.

21. A liquid crystal medium according to claim 4, wherein the proportion of compounds of formulae CY, PY and ZK is greater than 70%.

22. A liquid crystal medium according to claim 1, wherein said one or more compounds of formula I are selected from the following sub-formulae:

Ia
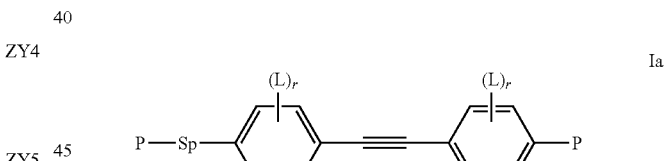

Ib

Ic
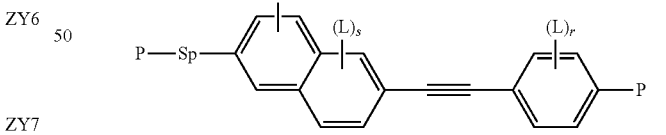

Id
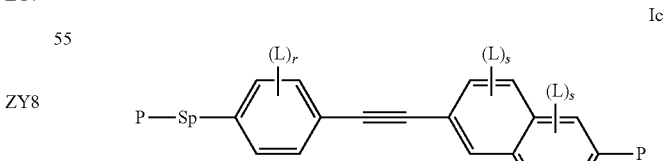

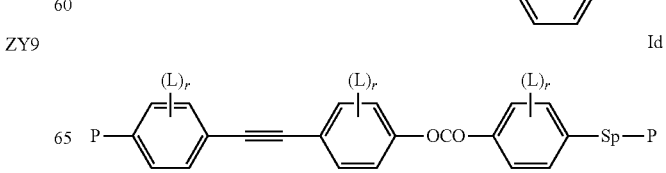

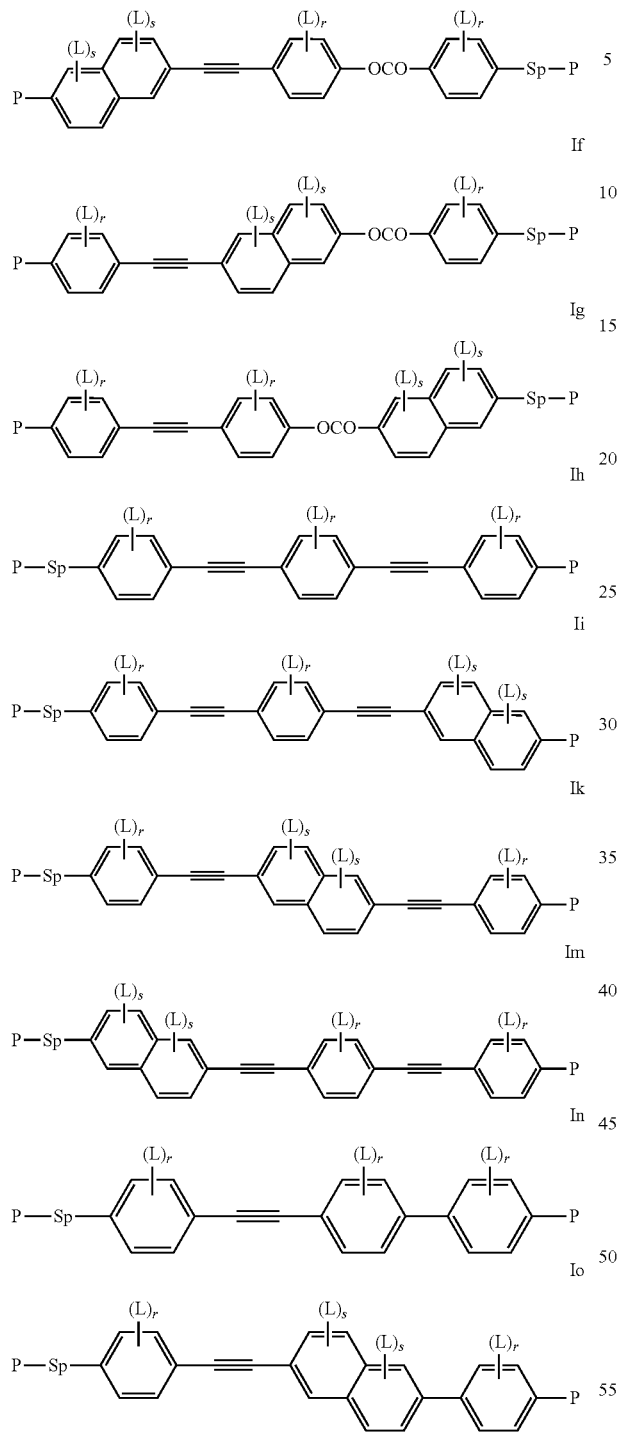
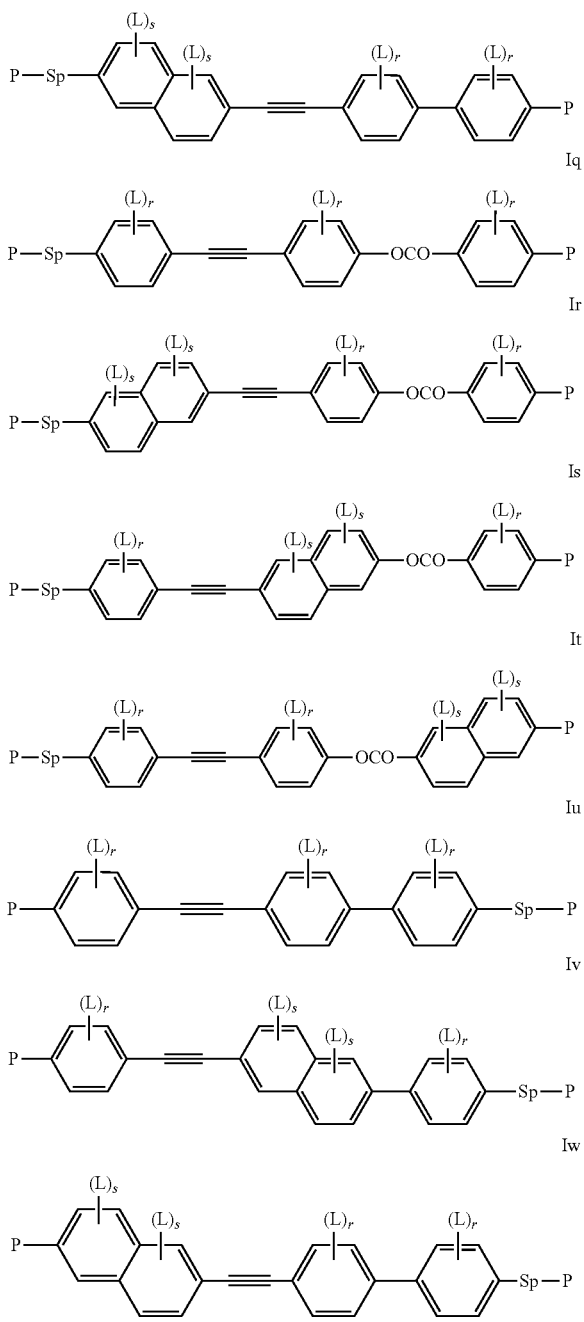
wherein P, Sp and L have the meanings indicated in claim 1, r denotes 0, 1, 2, 3 or 4, and s denotes 0, 1, 2 or 3.
* * * * *